（12）United States Patent
Wang et al.

(10) Patent No.: US 11,020,006 B2
(45) Date of Patent: Jun. 1, 2021

(54) TRANSCRANIAL PHOTOACOUSTIC/THERMOACOUSTIC TOMOGRAPHY BRAIN IMAGING INFORMED BY ADJUNCT IMAGE DATA

(71) Applicant: California Institute of Technology, Pasadena, CA (US)

(72) Inventors: Lihong V. Wang, Arcadia, CA (US); Liming Nie, St. Louis, MO (US); Xin Cai, St. Louis, MO (US); Konstantin Maslov, Pasadena, CA (US); Mark A. Anastasio, St. Louis, MO (US); Chao Huang, St. Louis, MO (US); Robert W. Schoonover, St. Louis, MO (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 1044 days.

(21) Appl. No.: 14/436,581

(22) PCT Filed: Oct. 18, 2013

(86) PCT No.: PCT/US2013/065594
§ 371 (c)(1),
(2) Date: Apr. 17, 2015

(87) PCT Pub. No.: WO2014/063005
PCT Pub. Date: Apr. 24, 2014

(65) Prior Publication Data
US 2015/0245771 A1 Sep. 3, 2015

Related U.S. Application Data

(60) Provisional application No. 61/762,415, filed on Feb. 8, 2013, provisional application No. 61/715,671, filed on Oct. 18, 2012.

(51) Int. Cl.
A61B 5/00 (2006.01)
A61B 5/055 (2006.01)
(Continued)

(52) U.S. Cl.
CPC .......... *A61B 5/0095* (2013.01); *A61B 5/0035* (2013.01); *A61B 5/0042* (2013.01);
(Continued)

(58) Field of Classification Search
CPC ..... A61B 5/0095; A61B 5/055; A61B 5/4839; A61B 5/4848; A61B 5/725; A61B 5/7282;
(Continued)

(56) References Cited

U.S. PATENT DOCUMENTS 4,029,756 A 6/1977 Gaafar
4,127,318 A 11/1978 Determann et al.
(Continued)

FOREIGN PATENT DOCUMENTS

CN 1883379 A 12/2006
EP 0012262 A1 6/1980
(Continued)

OTHER PUBLICATIONS

Aubry J.-F., et al. , "Experimental demonstration of noninvasive transskull adaptive focusing based on prior computed tomography scans," J. Acoust. Soc. Am. 113(1), 84-93 (2003). (Year: 2003).*
(Continued)

*Primary Examiner* — Keith M Raymond
*Assistant Examiner* — Helene Bor
(74) *Attorney, Agent, or Firm* — Sheila Martinez-Lemke; Weaver Austin Villeneuve & Sampson LLP

(57) ABSTRACT

Systems and methods of reconstructing photoacoustic imaging data corresponding to a brain of a subject through a skull of a subject utilizing a reconstruction method that incorpo-
(Continued)

rates a spatial model of one or more acoustic properties of the brain and skull of the subject derived from an adjunct imaging dataset.

20 Claims, 19 Drawing Sheets

(51) Int. Cl.
  *A61B 6/03* (2006.01)
  *A61M 31/00* (2006.01)
  *A61B 6/00* (2006.01)
  *G01N 29/24* (2006.01)

(52) U.S. Cl.
  CPC .......... *A61B 5/055* (2013.01); *A61B 5/4839* (2013.01); *A61B 5/4848* (2013.01); *A61B 5/725* (2013.01); *A61B 5/7282* (2013.01); *A61B 6/032* (2013.01); *A61M 31/005* (2013.01); *G01N 29/2418* (2013.01); *A61B 6/501* (2013.01); *A61B 2576/026* (2013.01)

(58) Field of Classification Search
  CPC ... A61B 6/032; A61B 6/501; A61B 2576/026; A61B 5/0042; A61B 5/0035; A61M 31/005; G01N 29/2418
  See application file for complete search history.

(56) References Cited

U.S. PATENT DOCUMENTS

| | | |
|---|---|---|
| 4,255,971 A | 3/1981 | Rosencwaig |
| 4,267,732 A | 5/1981 | Quate |
| 4,284,324 A | 8/1981 | Huignard et al. |
| 4,375,818 A | 3/1983 | Suwaki et al. |
| 4,385,634 A | 5/1983 | Bowen |
| 4,430,897 A | 2/1984 | Quate |
| 4,430,987 A | 2/1984 | Heller |
| 4,462,255 A | 7/1984 | Guess et al. |
| 4,468,136 A | 8/1984 | Murphy et al. |
| 4,489,727 A | 12/1984 | Matsuo et al. |
| 4,546,771 A | 10/1985 | Eggleton et al. |
| 4,596,254 A | 6/1986 | Adrian et al. |
| 4,687,304 A | 8/1987 | Piller et al. |
| 4,740,081 A | 4/1988 | Martens et al. |
| 4,802,461 A | 2/1989 | Cho |
| 4,802,487 A | 2/1989 | Martin et al. |
| 4,809,703 A | 3/1989 | Ishikawa et al. |
| 4,850,363 A | 7/1989 | Yanagawa |
| 4,860,758 A | 8/1989 | Yanagawa et al. |
| 4,869,256 A | 9/1989 | Kanno et al. |
| 4,872,758 A | 10/1989 | Miyazaki et al. |
| 4,921,333 A | 5/1990 | Brody et al. |
| 4,929,951 A | 5/1990 | Small |
| 4,995,396 A | 2/1991 | Inaba et al. |
| 5,070,455 A | 12/1991 | Singer et al. |
| 5,083,549 A | 1/1992 | Cho et al. |
| 5,107,844 A | 4/1992 | Kami et al. |
| 5,115,814 A | 5/1992 | Griffith et al. |
| 5,125,410 A | 6/1992 | Misono et al. |
| 5,140,463 A | 8/1992 | Yoo et al. |
| 5,170,793 A | 12/1992 | Takano et al. |
| 5,194,723 A * | 3/1993 | Cates .............. G01N 29/2418 219/121.62 |
| 5,207,672 A | 5/1993 | Roth et al. |
| 5,227,912 A | 7/1993 | Ho et al. |
| 5,305,759 A | 4/1994 | Kaneko et al. |
| 5,321,501 A | 6/1994 | Swanson et al. |
| 5,329,817 A | 7/1994 | Garlick et al. |
| 5,331,466 A | 7/1994 | Van Saarloos |
| 5,345,938 A | 9/1994 | Nishiki et al. |
| 5,373,845 A | 12/1994 | Gardiner et al. |
| 5,414,623 A | 5/1995 | Lu et al. |
| 5,445,155 A | 8/1995 | Sieben |
| 5,465,722 A | 11/1995 | Fort et al. |
| 5,546,187 A | 8/1996 | Pepper et al. |
| 5,546,947 A | 8/1996 | Yagami et al. |
| 5,546,948 A | 8/1996 | Hamm et al. |
| 5,606,975 A | 3/1997 | Liang et al. |
| 5,615,675 A | 4/1997 | O'Donnell et al. |
| 5,635,784 A | 6/1997 | Seale |
| 5,651,366 A | 7/1997 | Liang et al. |
| 5,713,356 A | 2/1998 | Kruger |
| 5,718,231 A | 2/1998 | Dewhurst et al. |
| 5,781,294 A | 7/1998 | Nakato et al. |
| 5,836,872 A | 11/1998 | Kenet et al. |
| 5,840,023 A | 11/1998 | Oraevsky et al. |
| 5,860,934 A | 1/1999 | Sarvazyan |
| 5,913,234 A | 6/1999 | Julliard et al. |
| 5,971,998 A | 10/1999 | Russell et al. |
| 5,977,538 A | 11/1999 | Unger et al. |
| 5,991,697 A | 11/1999 | Nelson et al. |
| 6,055,097 A | 4/2000 | Lanni et al. |
| 6,102,857 A | 8/2000 | Kruger |
| 6,104,942 A | 8/2000 | Kruger |
| 6,108,576 A | 8/2000 | Alfano et al. |
| 6,111,645 A | 8/2000 | Tearney et al. |
| 6,134,003 A | 10/2000 | Tearney et al. |
| 6,216,025 B1 | 4/2001 | Kruger |
| 6,233,055 B1 | 5/2001 | Mandella et al. |
| 6,282,011 B1 | 8/2001 | Tearney et al. |
| 6,292,682 B1 | 9/2001 | Kruger |
| 6,309,352 B1 | 10/2001 | Oraevsky et al. |
| 6,341,036 B1 | 1/2002 | Tearney et al. |
| 6,379,325 B1 | 4/2002 | William et al. |
| 6,405,069 B1 | 6/2002 | Oraevsky et al. |
| 6,413,228 B1 | 7/2002 | Hung et al. |
| 6,421,164 B2 | 7/2002 | Tearney et al. |
| 6,432,067 B1 | 8/2002 | Martin et al. |
| 6,466,806 B1 | 10/2002 | Geva et al. |
| 6,485,413 B1 | 11/2002 | Boppart et al. |
| 6,490,470 B1 | 12/2002 | Kruger |
| 6,498,942 B1 | 12/2002 | Esenaliev et al. |
| 6,498,945 B1 | 12/2002 | Alfheim et al. |
| 6,501,551 B1 | 12/2002 | Tearney et al. |
| 6,545,264 B1 | 4/2003 | Stern |
| 6,564,087 B1 | 5/2003 | Pitris et al. |
| 6,567,688 B1 | 5/2003 | Wang |
| 6,590,830 B1 | 7/2003 | Garlick et al. |
| 6,626,834 B2 | 9/2003 | Dunnie et al. |
| 6,628,404 B1 | 9/2003 | Kelley et al. |
| 6,633,774 B2 | 10/2003 | Kruger |
| 6,654,630 B2 | 11/2003 | Zuluaga et al. |
| 6,658,279 B2 | 12/2003 | Swanson et al. |
| 6,694,173 B1 | 2/2004 | Bende et al. |
| 6,701,181 B2 | 3/2004 | Tang et al. |
| 6,751,490 B2 | 6/2004 | Esenaliev et al. |
| 6,764,450 B2 | 7/2004 | Yock |
| 6,831,781 B2 | 12/2004 | Tearney et al. |
| 6,833,540 B2 | 12/2004 | MacKenzie et al. |
| 6,839,496 B1 | 1/2005 | Mills et al. |
| 6,846,288 B2 | 1/2005 | Nagar et al. |
| 6,853,446 B1 | 2/2005 | Almogy et al. |
| 6,877,894 B2 | 4/2005 | Vona et al. |
| 6,937,886 B2 | 8/2005 | Zavislan |
| 6,956,650 B2 | 10/2005 | Boas et al. |
| 7,072,045 B2 | 7/2006 | Chen et al. |
| 7,198,778 B2 | 4/2007 | Achilefu et al. |
| 7,231,243 B2 | 6/2007 | Tearney et al. |
| 7,245,789 B2 | 7/2007 | Bates et al. |
| 7,266,407 B2 | 9/2007 | Li et al. |
| 7,322,972 B2 | 1/2008 | Viator et al. |
| 7,357,029 B2 | 4/2008 | Falk |
| 7,382,949 B2 | 6/2008 | Bouma et al. |
| 7,541,602 B2 | 6/2009 | Metzger et al. |
| 7,610,080 B1 | 10/2009 | Winchester, Jr. et al. |
| 7,917,312 B2 | 3/2011 | Wang et al. |
| 8,016,419 B2 | 9/2011 | Zhang et al. |
| 8,025,406 B2 | 9/2011 | Zhang et al. |
| 8,143,605 B2 | 3/2012 | Metzger et al. |
| 8,397,573 B2 | 3/2013 | Kobayashi |
| 8,416,421 B2 | 4/2013 | Wang et al. |
| 8,454,512 B2 | 6/2013 | Wang et al. |

(56) References Cited

U.S. PATENT DOCUMENTS

| | | | |
|---|---|---|---|
| 8,891,088 B2 | 11/2014 | Goldschmidt et al. | |
| 8,997,572 B2 | 4/2015 | Wang et al. | |
| 9,220,415 B2 | 12/2015 | Mandelis et al. | |
| 9,234,841 B2 | 1/2016 | Wang et al. | |
| 9,335,605 B2 | 5/2016 | Wang et al. | |
| 9,528,966 B2 | 12/2016 | Wang et al. | |
| 9,618,445 B2 | 4/2017 | Sun et al. | |
| 10,359,400 B2 | 7/2019 | Wang et al. | |
| 10,433,733 B2 | 10/2019 | Wang et al. | |
| 10,448,850 B2 | 10/2019 | Wang et al. | |
| 2001/0052979 A1 | 12/2001 | Treado et al. | |
| 2002/0093637 A1 | 7/2002 | Yuan et al. | |
| 2002/0173780 A1* | 11/2002 | Altshuler | A61B 18/203 606/9 |
| 2002/0176092 A1 | 11/2002 | Deck | |
| 2003/0097066 A1 | 5/2003 | Shelby et al. | |
| 2003/0160957 A1 | 8/2003 | Oldham et al. | |
| 2003/0160967 A1 | 8/2003 | Houston et al. | |
| 2004/0030255 A1* | 2/2004 | Alfano | A61B 5/0073 600/476 |
| 2004/0039379 A1 | 2/2004 | Viator et al. | |
| 2004/0082070 A1 | 4/2004 | Jones et al. | |
| 2004/0254474 A1 | 12/2004 | Seibel et al. | |
| 2005/0015002 A1 | 1/2005 | Dixon et al. | |
| 2005/0028482 A1* | 2/2005 | Cable | A61B 5/0059 52/749.1 |
| 2005/0143664 A1 | 6/2005 | Chen et al. | |
| 2005/0154313 A1 | 7/2005 | Desilets et al. | |
| 2005/0168749 A1 | 8/2005 | Ye et al. | |
| 2005/0217381 A1 | 10/2005 | Falk | |
| 2005/0234315 A1 | 10/2005 | Mayevsky et al. | |
| 2005/0277824 A1* | 12/2005 | Aubry | A61B 8/00 600/407 |
| 2006/0055936 A1 | 3/2006 | Yun et al. | |
| 2006/0058614 A1 | 3/2006 | Tsujita | |
| 2006/0122516 A1 | 6/2006 | Schmidt et al. | |
| 2006/0181791 A1 | 8/2006 | Van Beek et al. | |
| 2006/0184042 A1 | 8/2006 | Wang et al. | |
| 2006/0235299 A1 | 10/2006 | Martinelli | |
| 2006/0247510 A1 | 11/2006 | Wiemker et al. | |
| 2006/0264717 A1 | 11/2006 | Pesach et al. | |
| 2007/0088206 A1 | 4/2007 | Peyman et al. | |
| 2007/0093702 A1 | 4/2007 | Yu et al. | |
| 2007/0213590 A1 | 9/2007 | Squicciarini | |
| 2007/0213618 A1 | 9/2007 | Li et al. | |
| 2007/0213693 A1 | 9/2007 | Plunkett | |
| 2007/0282200 A1 | 12/2007 | Johnson et al. | |
| 2007/0299341 A1 | 12/2007 | Wang et al. | |
| 2008/0029711 A1 | 2/2008 | Viellerobe et al. | |
| 2008/0037367 A1 | 2/2008 | Gross et al. | |
| 2008/0088838 A1 | 4/2008 | Raicu et al. | |
| 2008/0123083 A1 | 5/2008 | Wang et al. | |
| 2008/0173093 A1 | 7/2008 | Wang et al. | |
| 2008/0230717 A1 | 9/2008 | Ashkenazi et al. | |
| 2009/0051900 A1 | 2/2009 | Moon et al. | |
| 2009/0054763 A1 | 2/2009 | Wang et al. | |
| 2009/0088631 A1 | 4/2009 | Dietz et al. | |
| 2009/0116518 A1 | 5/2009 | Patel et al. | |
| 2009/0138215 A1 | 5/2009 | Wang et al. | |
| 2009/0185191 A1 | 7/2009 | Boppart et al. | |
| 2009/0227997 A1 | 9/2009 | Wang et al. | |
| 2010/0079768 A1 | 4/2010 | Wang et al. | |
| 2010/0134793 A1 | 6/2010 | Krishnamachari et al. | |
| 2010/0245766 A1 | 9/2010 | Zhang et al. | |
| 2010/0245769 A1 | 9/2010 | Zhang et al. | |
| 2010/0245770 A1 | 9/2010 | Zhang et al. | |
| 2010/0249562 A1 | 9/2010 | Zhang et al. | |
| 2010/0268042 A1 | 10/2010 | Wang et al. | |
| 2010/0285518 A1 | 11/2010 | Viator et al. | |
| 2010/0309466 A1 | 12/2010 | Lucassen et al. | |
| 2010/0322497 A1 | 12/2010 | Dempsey et al. | |
| 2011/0071402 A1 | 3/2011 | Masumura | |
| 2011/0122416 A1 | 5/2011 | Yang et al. | |
| 2011/0201914 A1 | 8/2011 | Wang et al. | |
| 2011/0251515 A1 | 10/2011 | Leuthardt et al. | |
| 2011/0275890 A1 | 11/2011 | Wang et al. | |
| 2011/0282181 A1 | 11/2011 | Wang et al. | |
| 2011/0282192 A1 | 11/2011 | Axelrod et al. | |
| 2012/0070817 A1 | 3/2012 | Wang et al. | |
| 2012/0074294 A1 | 3/2012 | Streuber et al. | |
| 2012/0118052 A1 | 5/2012 | O Donnell et al. | |
| 2012/0204648 A1 | 8/2012 | Wang et al. | |
| 2012/0275262 A1 | 11/2012 | Song et al. | |
| 2012/0307250 A1 | 12/2012 | Wang | |
| 2013/0199299 A1 | 8/2013 | Wang et al. | |
| 2013/0218002 A1* | 8/2013 | Kiraly | G01R 33/4814 600/411 |
| 2013/0245406 A1 | 9/2013 | Wang et al. | |
| 2014/0009808 A1 | 1/2014 | Wang et al. | |
| 2014/0142404 A1 | 5/2014 | Wang et al. | |
| 2014/0356897 A1 | 12/2014 | Wang et al. | |
| 2015/0005613 A1* | 1/2015 | Kim | G01N 29/0654 600/407 |
| 2015/0185187 A1 | 7/2015 | Wang et al. | |
| 2015/0272444 A1 | 10/2015 | Maslov et al. | |
| 2015/0272446 A1 | 10/2015 | Wang et al. | |
| 2015/0316510 A1 | 11/2015 | Fukushima et al. | |
| 2016/0081558 A1 | 3/2016 | Wang et al. | |
| 2016/0235305 A1 | 8/2016 | Wang et al. | |
| 2016/0242651 A1 | 8/2016 | Wang et al. | |
| 2016/0249812 A1 | 9/2016 | Wang et al. | |
| 2016/0262628 A1 | 9/2016 | Wang et al. | |
| 2016/0305914 A1 | 10/2016 | Wang et al. | |
| 2016/0310083 A1 | 10/2016 | Wang et al. | |
| 2016/0345886 A1 | 12/2016 | Wang et al. | |
| 2017/0065182 A1 | 3/2017 | Wang et al. | |
| 2017/0105636 A1 | 4/2017 | Wang et al. | |
| 2017/0367586 A9 | 12/2017 | Wang et al. | |
| 2018/0020920 A1 | 1/2018 | Ermilov et al. | |
| 2018/0132728 A1 | 5/2018 | Wang et al. | |
| 2019/0008444 A1 | 1/2019 | Wang et al. | |
| 2019/0125583 A1 | 5/2019 | Wang et al. | |
| 2019/0227038 A1 | 7/2019 | Wang et al. | |
| 2019/0307334 A1 | 10/2019 | Wang et al. | |
| 2020/0056986 A1 | 2/2020 | Wang et al. | |
| 2020/0073103 A1 | 3/2020 | Wang et al. | |
| 2020/0268253 A1 | 8/2020 | Wang et al. | |
| 2020/0275846 A1 | 9/2020 | Wang et al. | |
| 2020/0397523 A1 | 12/2020 | Gao et al. | |

FOREIGN PATENT DOCUMENTS

| | | |
|---|---|---|
| EP | 0919180 A1 | 6/1999 |
| EP | 1493380 A1 | 1/2005 |
| JP | 05-126725 A | 5/1993 |
| JP | 2000/292416 A | 10/2000 |
| JP | 2009/068977 A | 4/2009 |
| JP | 2010/017426 A | 1/2010 |
| JP | 2010/040161 A | 2/2010 |
| JP | 2012/143384 A | 8/2012 |
| JP | 2014124242 A | 7/2014 |
| JP | 2014/224806 A | 12/2014 |
| JP | 2016-101260 A | 6/2016 |
| JP | 6086718 B2 | 3/2017 |
| KR | 100946550 B1 | 3/2010 |
| KR | 2017-0006470 A | 1/2017 |
| WO | WO2006/111929 A1 | 10/2006 |
| WO | WO2007/088709 A1 | 8/2007 |
| WO | WO2007/148239 A2 | 12/2007 |
| WO | WO2008/062354 A1 | 5/2008 |
| WO | WO2008/100386 A2 | 8/2008 |
| WO | WO2009/055705 A2 | 4/2009 |
| WO | WO2010/048258 A1 | 4/2010 |
| WO | WO2010/080991 A2 | 7/2010 |
| WO | WO2011/060101 A2 | 5/2011 |
| WO | WO2011/091360 A2 | 7/2011 |
| WO | WO2011/127428 A2 | 10/2011 |
| WO | WO2012/035472 A1 | 3/2012 |
| WO | WO2013/086293 A1 | 6/2013 |
| WO | WO2015/118881 A1 | 8/2015 |
| WO | WO2018/102446 A2 | 6/2018 |
| WO | WO2018/209046 A1 | 11/2018 |

(56) References Cited

FOREIGN PATENT DOCUMENTS

OTHER PUBLICATIONS

Treeby B. E., Zhang E. Z., Cox B. T., "Photoacoustic tomography in absorbing acoustic media using time reversal," Inverse Probl. 26(11), (2010) (Year: 2010).*
Huang et al., "Aberration correction for transcranial photoacoustic tomography of primates employing adjunct image Journal of Biomedical Optics 17(6):066016-1 to 066016-8, Jun. 2012. data".
International Search Report dated Mar. 27, 2014 for International Application No. PCT/US2013/065594 (4 pages).
Written Opinion dated Mar. 27, 2014 for International Application No. PCT/US2013/065594 (6 pages).
Office Action from related U.S. Appl. No. 11/625,099, dated Nov. 1, 2010.
Final Office Action from related U.S. Appl. No. 11/625,099, dated Apr. 20, 2010.
Office Action from related U.S. Appl. No. 12/254,643, dated Aug. 6, 2010.
Notice of Allowance from related U.S. Appl. No. 12/254,643, dated Nov. 22, 2010.
Office Action from related U.S. Appl. No. 12/568,069, dated Dec. 21, 2012.
Office Action from related U.S. Appl. No. 12/568,069, dated Mar. 29, 2012.
Final Office Action from related U.S. Appl. No. 12/568,069, dated Sep. 18, 2012.
Notice of Allowance from related U.S. Appl. No. 12/568,069, dated Feb. 22, 2013.
Office Action from related U.S. Appl. No. 12/739,589, dated Jul. 19, 2012.
Notice of Allowance from related U.S. Appl. No. 12/739,589, dated Feb. 5, 2013.
Office Action from related U.S. Appl. No. 13/125,522, dated Jan. 22, 2013.
Final Office Action from related U.S. Appl. No. 13/125,522, dated May 23, 2013.
Office Action from related U.S. Appl. No. 13/125,522, dated Jul. 17, 2014.
Final Office Action from related U.S. Appl. No. 13/125,522, dated Oct. 29, 2014.
Office Action dated Aug. 26, 2015 issued in U.S. Appl. No. 13/125,522.
Final Office Action dated Mar. 3, 2016 issued in U.S. Appl. No. 13/125,522.
Notice of Allowance dated Sep. 19, 2016 issued in U.S. Appl. No. 13/125,522.
Office Action from related U.S. Appl. No. 13/143,832, dated Apr. 18, 2014.
Office Action from related U.S. Appl. No. 13/450,793, dated Jun. 5, 2013.
Final Office Action from related U.S. Appl. No. 13/450,793, dated Nov. 22, 2013.
Office Action from related U.S. Appl. No. 13/450,793, dated Mar. 24, 2014.
Office Action from related U.S. Appl. No. 13/450,793, dated Aug. 1, 2014.
Office Action from related U.S. Appl. No. 13/574,994, dated Mar. 17, 2014.
Final Office Action from related U.S. Appl. No. 13/574,994, dated Aug. 26, 2014.
Notice of Allowance dated Nov. 17, 2015 from U.S. Appl. No. 13/574,994.
Office Action dated Jan. 20, 2015, from U.S. Appl. No. 14/026,577.
Final Office Action dated Sep. 30, 2015, from U.S. Appl. No. 14/026,577.
Notice of Allowance dated Jan. 5, 2016, from U.S. Appl. No. 14/026,577.
Office Action dated Nov. 13, 2017, from U.S. Appl. No. 15/148,685.
Final Office Action dated Sep. 24, 2018, from U.S. Appl. No. 15/148,685.
Notice of Allowance dated May 16, 2019, from U.S. Appl. No. 15/148,685.
Office Action from related U.S. Appl. No. 13/637,897, dated Aug. 1, 2014.
Office Action from related U.S. Appl. No. 14/164,117, dated Dec. 11, 2015.
Office Action dated Dec. 13, 2019 issued in U.S. Appl. No. 15/037,468.
Notice of Allowance dated Mar. 23, 2020 issued in U.S. Appl. No. 15/037,468.
Office Action dated Jun. 20, 2014 issued in U.S. Appl. No. 13/369,558.
Notice of Allowance dated Jul. 29, 2014 issued in U.S. Appl. No. 13/369,558.
Notice of Allowance dated Dec. 5, 2014 issued in U.S. Appl. No. 13/369,558.
Office Action dated Apr. 21, 2017 issued in U.S. Appl. No. 14/639,676.
Final Office Action dated Nov. 15, 2017 issued in U.S. Appl. No. 14/639,676.
Office Action dated May 31, 2018 issued in U.S. Appl. No. 14/639,676.
Notice of Allowance dated Dec. 12, 2018 issued in U.S. Appl. No. 14/639,676.
Office Action dated Feb. 28, 2020 issued in U.S. Appl. No. 16/372,597.
Office Action dated Aug. 19, 2019 issued in U.S. Appl. No. 16/372,597.
The International Search Report and The Written Opinion of the International Searching Authority, or the Declaration, for PCT/US2009/061435, dated Mar. 29, 2010, 6 pages.
The International Search Report and the Written Opinion of the International Searching Authority, dated Sep. 22, 2011, from related application No. PCT/US2011/022253, 6 pgs.
International Search Report of International Application No. PCT/US2014/066437, dated Feb. 26, 2015, 3 pages.
Partial European Search Report issued for European Application No. 17159220.7, dated Aug. 23, 2017 (9 pages).
International Search Report and Written Opinion dated Apr. 22, 2009, from Application No. PCT/US2008/081167 (7 pages).
International Search Report and Written Opinion from Application Serial No. PCT/US2010/020488, dated Aug. 31, 2010 (10 pages).
International Search Report and Written Opinion from Application Serial No. PCT/US2011/031823, dated Dec. 26, 2011 (8 pages).
International Search Report and Written Opinion from Application Serial No. PCT1US2012/068403, dated Mar. 19, 2013 (10 pages).
Extended European Search Report from European Application Serial No. 08842292.8, dated Dec. 17, 2013 (8 pages).
Final Office Action from related Japanese Patent Application No. JP 2010531281, dated Mar. 11, 2014, (5 pages).
International Search Report and Written Opinion dated Dec. 2, 2019, issued in Application No. PCT/US2019/046574.
International Search Report and Written Opinion dated Dec. 23, 2019, issued in Application No. PCT/US2019/049594.
International Search Report dated Aug. 9, 2018 issued in Application No. PCT/US2018/032007.
Written Opinion of the International Searching Authority dated Aug. 9, 2018 issued in Application No. PCT/US2018/032007.
International Preliminary Report on Patentability dated Nov. 12, 2019 issued in PCT/US2018/032007.
Abdelmohsen, et al., "Micro- and nano-motors for biomedical applications," J. Mater. Chem. B 2, (2014) pp. 2395-2408.
Al, et al., "Spectral-domain optical coherence tomography: Removal of autocorrelation using an optical switch," Applied Physics Letters, (Mar. 15, 2006), 88(11): pp. 111115-1-111115-3. <doi:10.1063/1.2186520>.
Allen, et al. "Pulsed Near-Infrared Laser Diode Excitation System for Biomedical Photoacoustic Imaging," Optics Letters, Optical Society of America, USA., vol. 31, No. 23, Dec. 1, 2006, pp. 3462-3464.
Alomair, et al., "In vivo high angular resolution diffusion-weighted imaging of mouse brain at 16.4 Tesla," PloS One 10, Jun. 25, 2015, e0130133, pp. 1-17.

(56) References Cited

OTHER PUBLICATIONS

Baheiraei, et al., "Investigation of magnesium incorporation within gelatin/calcium phosphate nanocomposite scaffold for bone tissue engineering," Int. J. Appl. Ceram. Technol. 12, (2015) pp. 245-253.
Baker, M. J. et al., "Using Fourier transform IR spectroscopy to analyze biological materials," Nat. Protoc. 9, 1771-1791 (2014).
Bansil, et al., "The biology of mucus: Composition, synthesis and organization" Adv. Drug Deliv. Rev. 124, (2018) pp. 3-15.
Beaven, G. H. & Holiday, E. R., "Ultraviolet absorption spectra of proteins and amino acids," Adv. Protein Chem 7, 319-386 (1952).
Bell, A.G., "On the Production and Reproduction of Sound by Light," American Journal of Sciences, Oct. 1880, pp. 305-324, Third Series, vol. XX, USA.
Bellinger, et al., "Oral, ultra-long-lasting drug delivery: Application toward malaria elimination goals" Sci Transl. Med. 8(365), Nov. 16, 2016, 365ra157, pp. 1-25. <doi:10.1126/scitranslmed.aag2374>.
Bioucas-Dias, J.M. and Figueiredo, M.A.T. "A new TwIST: two-step iterative shrinkage/thresholding algorithms for image restoration," IEEE Trans. Image Process. 16, 2992-3004 (Dec. 2007).
Brenner, et al., "Computed Tomography—An Increasing Source of Radiation Exposure" N. Engl. J. Med 357;22, Nov. 29, 2007, pp. 2277-2284.
Calasso et al., "Photoacoustic Point Source," Physical Review Letters, vol. 86, No. 16, Apr. 16, 2001, pp. 3550-3553.
Cannata et al., "Development of a 35-MHz Piezo-Composite Ultrasound Array for Medical Imaging," IEE Transactions on Ultrasonics, Ferroelectrics, and Frequency Control, 53(1): pp. 224-236 (2006).
Celli, J. P., et al., "Helicobacter pylori moves through mucus by reducing mucin viscoelasticity," Proc. Natl. Acad. Sci. U. S. A. 106, (2009) pp. 14321-14326.
Chan, et al., "New opportunities in micro- and macro-attenuated total reflection infrared spectroscopic imaging: spatial resolution and sampling versatility," Appl. Spectrosc. 57, 381-389 (2003).
Cheng, J.-X. Et al., "Vibrational spectroscopic imaging ofliving systems: an emerging platform for biology and medicine," Science, vol. 350 aaa8870, No. 6264, Nov. 27, 2015, pp. 1054-1063.
Cheong, et al., "A review of the optical properties of biological tissues," IEEE J. Quantum Electronics, 26(12): pp. 2166-2185 (1980).
Chourasia, et al., "Design and Development of Multiparticulate System for Targeted Drug Delivery to Colon," Drug Delivery, 11:3, (2004) pp. 201-207.
Cox, B., Beard, P., "Photoacoustic tomography with a single detector in a reverberant cavity" J. Acoust. Soc. Am. 125, 1426 (Mar. 2009).
Cui, Y., et al. "Transferring-conjugated magnetic silica PLGA nanoparticles loaded with doxorubicin and paclitaxel for brain glioma treatment," Biomaterials 34, (2013) pp. 8511-8520.
De Boer, et al., "Improved signal-to-noise ratio in spectral-domain compared with time-domain optical coherence tomography" Optics Letters, vol. 28, No. 21, Nov. 1, 2003, pp. 2067-2069.
D'Andrea, et al., "Time-resolved optical imaging through turbid media using a fast data acquisition system based on a gated CCD camera" Journal of Physics D: Applied Physics, vol. 36, No. 14, Jul. 1, 2003, pp. 1675-1681.
Danielli, et al., "Label-free photoacoustic nanoscopy," Journal of Biomedical Optics, vol. 19, No. 8, Aug. 2014, pp. 086006-1-086006-10.
Dazzi, A. et al., "AFM-IR: technology and applications in nanoscale infrared spectroscopy and chemical imaging," Chem. Rev. 117, 5146-5173 (2017).
Dazzi, A., et al., "Local infrared microspectroscopy with subwavelength spatial resolution with an atomic force microscope tip used as a photothermal sensor," Optics Letters, vol. 30, No. 18, Sep. 15, 2005, pp. 2388-2390.
De Avila, et al., "Micromotor-enabled active drug delivery for in vivo treatment of stomach infection" Nat. Commun. 8: 272, (2017) pp. 1-9.

De Zerda, et al., "Family of enhanced photoacoustic imaging agents for high-sensitivity and multiplexing studies in living mice," ACS Nano 6(6), Jun. 26, 2012, pp. 4694-4701.
Diebold, et al., "Photoacoustic Monopole Radiation in One, Two and Three Dimensions," Physical Review Letters, Figs. 1 and 2, vol. 67, No. 24, Dec. 9, 1991 , pp. 3384-3387.
Diebold, et al., "Photoacoustic Signature of Particulate Matter: Optical Production of 9 Acoustic Monopole Radiation," Science New Series, Oct. 5, 1990, pp. 101-104, vol. 250, No. 4977, pp. 101-104.
Diem, M. et al., "Molecular pathology via IR and Raman spectral imaging." Journal of Biophotonics, vol. 6, No. 11-12 (2013) pp. 855-886. <doi:10.1002/jbio.201300131>.
Diem, M., et al., "A decade of vibrational micro-spectroscopy of human cells and tissue (1994-2004)†," Analyst, Oct. 2004, vol. 129, No. 10, pp. 880-885. <doi:10.1039/b408952a>.
Draeger, C., Fink, M., "One-channel time reversal of elastic waves in a chaotic 2D-silicon cavity," Phys. Rev. Lett. 79, 407-410 (Jul. 21, 1997).
Dunn, et al., "Transport-based image reconstruction in turbid media with small source-detector separations," Optics Letters, vol. 25, No. 24, Dec. 15, 2000, pp. 1777-1779.
Eghtedari, et al., "High Sensitivity of In Vivo Detection of Gold Nanorods Using a Laser Optoacoustic Imaging System," Nano Letters, vol. 7, No. 7, 2007, pp. 1914-1918.
Ermilov et al., "Laser optoacoustic imaging system for detection of breast cancer," Journal of Biomedical Optics, vol. 14 No. 2, pp. 24007-024007-14 (2009).
Erpelding et al., "Sentinel Lymph Nodes in the Rat: Noninvasive Photoacoustic and US Imaging with a Clinical US System," Radiology, 256(1): 102-110 (2010).
Evans, et al., "Coherent Anti-Stokes Raman Scattering Microscopy: Chemical Imaging for Biology and Medicine," Annual Review of Analytical Chemistry 1, (2008), pp. 883-909.
Fan, et al., "Development of a Laser Photothermoacoustic Frequency-Swept System for Subsurface Imaging: Theory and Experiment," J. Acoust. Soc. Am., vol. 116 (6), Dec. 2004, pp. 3523-3533.
Fan, et al., "Sub-Cellular Resolution Delivery of a Cytokine via Precisely Manipulated Nanowires" Nat. Nanotechnol. 5(7), Jul. 2010, 545-551. <doi:10.1038/nnano.2010.104>.
Fang, et al., "Photoacoustic Doppler effect from flowing small light-absorbing particles," Physical Review Letters 99(18) 184501-(1-4) (Nov. 2, 2007).
Fercher, et al., "Measurement of Intraocular Distances by Backscattering Spectral Interferometry," Optics Communications, 1995, vol. 117, pp. 43-48.
Fernandez, D. C., Bhargava, R., Hewitt, S. M. & Levin, I. W., "Infrared spectroscopic imaging for histopathologic recognition," Nat. Biotechnol. 23, 469-474 (2005).
Foster, et al., "Advances in ultrasound biomicroscopy" Ultrasound in Medicine & Biology, vol. 26, No. 1, Jan. 2000, pp. 1-27.
Fujita, K., et al., "Confocal multipoint multiphoton excitation microscope with microlens and pinhole arrays," Opt. Comm. 174, 7-12 (Jan. 15, 2000).
Furstenberg, et. al., "Chemical Imaging using Infrared Photothermal Microspectroscopy," In Proceedings of SPIE Defense, Security, and Sensing (eds Druy, M.A. & Crocombe, R. A.) 837411 (SPIE, 2012).
Gaihre, et al., "Gelatin-coated magnetic iron oxide nanoparticles as carrier system: Drug loading and in vitro drug release study," Int. J. Pharm. 365, (2009) pp. 180-189.
Gao, et al., "Single-shot compressed ultrafast photography at one hundred billion frames per second," Nature 516(7529) 74-77 (Dec. 4, 2014).
Gao, et al., "A review of snapshot multidimensional optical imaging: measuring photon tags in parallel" Phys Rep. 616, Feb. 29, 2016, pp. 1-37. <doi:10.1016/j.physrep.2015.12.004>.
Gao, et al., "Artificial micromotors in the mouse's stomach: A step toward in vivo use of synthetic motors,"ACS Nano 9, (2015) pp. 117-123.
Gibson, et al., "Recent advances in diffuse optical imaging" Physics in Medicine and Biology 50, 2005, pp. R1-R43, Inslilule of Physics Publishing, UK.

(56) References Cited

OTHER PUBLICATIONS

Gong, L. et al., "Breaking the diffraction limit by saturation in stimulated-Raman-scattering microscopy: A theoretical study," Phys. Rev. A 90, 13818 (2014).

Griffiths, P., "Fourier transform infrared spectrometry," Science 21, 297-302 (1983).

Guggenheim, et al., "Ultrasensitive planoconcave optical microresonators for ultrasound sensing", Nat. Photon. 11, 714-721 (2017).

Guittet C, et al., "In vivo high-frequency ultrasonic characterization of human dermis" IEEE Transactions on Bio-medical Engineering. Jun. 1999;46(6):740-746. <doi:10.1109/10.764950>.

Guo, et al., "Calibration-free absolute quantification of optical absorption coefficients using acoustic spectra in three-dimensional photoacoustic microscopy of biological tissue" Opt Lett. 2010 ; 35(12): 2067-2069. <doi:10.1364/OL.35.002067>.

Guo, et al., "CsxWO3 nanorods coated with polyelectrolyte multilayers as a multifunctional nanomaterial for bimodal imaging-guided photothermal/photodynamic cancer treatment," Adv. Mater. 29, 1604157 (2017).

Haas, J. et al., "Advances in Mid-Infrared Spectroscopy for Chemical Analysis," Annu. Rev. Anal. Chem. 9 (2016) pp. 45-68.

Hai, et al., "Near-infrared optical-resolution photoacoustic microscopy", Opt. Lett. 39, 5192-5195 (Sep. 1, 2014).

Hai, et al., "High-throughput, label-free, single-cell photoacoustic microscopy of intratumoral metabolic heterogeneity," Nature Biomedical Engineering 3(5) 381-391 (May 2019).

Hebden et al., "Enhanced time-resolved imaging with a diffusion model of photon transport" Optics Letters, vol. 19, No. 5, 1994, pp. 311-313.

Hee, et al., "Femtosecond transillumination tomography in thick tissues" Optics Letters, vol. 18, No. 13, 1993, pp. 1107-1109.

Hillman, et al., "Laminar optical tomography: demonstration of millimeter-scale depth-resolved imaging in turbid media," Optics Letters, vol. 29, No. 14, Jul. 15, 2004, pp. 1650-1652.

Hoelen, et al., "Three Dimensional Photoacoustic Imaging of Blood Vessels in Tissue" Optics Letters, 1998, pp. 648-650, vol. 23, No. 8, Optical Society of America, USA.

Hong, et al., "Simple Method to Produce Janus Colloidal Particles in Large Quantity" Langmuir 22, (2006) pp. 9495-9499.

Hu, C., et al., "Soft Micro- and Nanorobotics," Annu. Rev. Control. Robot. Auton. Syst. 1, (2018) pp. 53-75.

Hu, W., et al., "Small-scale soft-bodied robot with multimodal locomotion," Nature 554, 81-85, (2018).

Hu, S. et al., "Three-dimensional optical-resolution photoacoustic microscopy," Journal of Visualized Experiments 51 (2011).

Hu, S., et al., "Label-free Photoacoustic Ophthalmic Angiography" Optics Letters, 35(1), Jan. 1, 2010, pp. 1-3.

Huang, et al., "Optical Coherence Tomography," Science, New Series, vol. 254, No. 5035, Nov. 22, 1991 , pp. 1178-1181.

Huber, et al., "Three-Dimensional and C-Mode 6 OCT Imaging with a Compact, Frequency Swept Laser Source at 1300 nn" Optics Express, vol. 13, No. 26, Dec. 26, 2005, pp. 10523-10526.

Imai, T. et al., "High-throughput ultraviolet photoacoustic microscopy with multifocal excitation," Journal of Biomedical Optics 23(3), 036007 (Mar. 15, 2018).

Ing, R. K., Quieffin, N., Catheline, S., Fink, M., "In solid localization of finger impacts using acoustic time-reversal process," Appl. Phys. Lett. 87, 204104 (Nov. 14, 2004).

Ji, M. et al., "Detection of human brain tumor infiltration with quantitative stimulated Raman scattering microscopy," Sci. Transl. Med 7, 309ra163 (2015).

Ji, T. et al. "Preparation, Characterization, and Application of Au-Shell/Polystyrene Beads and Au-hell/Magnetic Beads" Adv. Mater. 13(16), Aug. 2001, pp. 1253-1256.

Karamata, et al., "Multiple Scattering in Optical Coherence Tomography I Investigation and Modeling" Journal of Optical Society of America, vol. 22, No. 7 (2005) pp. 1369-1379.

Karamata, et al., "Multiple scattering in optical coherence tomography. II. Experimental and theoretical investigation of cross talk in wide-field optical coherence tomography" J. Opt. Soc. Am. A/vol. 22, No. 7/Jul. 2005, pp. 1380-1388.

Kim, C. et al., "In vivo molecular photoacoustic tomography of melanomas targeted by bio-conjugated gold nanocages" ACS Nano, 2010; 4(8), pp. 4559-4564. <doi:10.1021/nn100736c>.

Kirch, J., et al., "Optical tweezers reveal relationship between microstructure and nanoparticle penetration of pulmonary mucus," Proc. Natl. Acad. Sci. 109, (2012) pp. 18355-18360.

Knoll, B. & Keilmann, F., "Near-field probing of vibrational absorption for chemical microscopy," Nature 399, 134-137 (1999).

Kole, M. R., et al., "Discrete frequency infrared microspectroscopy and imaging with a tunable quantum cascade laser," Anal. Chem. 84, 10366-10372 (2012).

Kolkman, et al., "In Vivo Photoacoustic Imaging of Blood Vessels Using an Extreme-Narrow Aperture Sensor" IEEE Journal of Selected Topics in Quantum Electronics, vol. 9, No. 2, Mar./Apr. 2003, pp. 343-346.

Koziolek, et al., "Navigating the human gastrointestinal tract for oral drug delivery: Uncharted waters and new frontiers," Adv. Drug Delivery Rev. 101, (2016) pp. 75-88.

Kruger et al., "Photoacoustic Ultrasound (PAUS)-Reconstruction Tomography" Med. Phys., Oct. 1995, vol. 22 (10) Am. Assoc. Phys. Med., USA, pp. 1605-1609.

Kruger, et al., "Thermoacoustic computed tomography—technical considerations" Medical Physics, 26(9): 1832-1837 (1999).

Kruger et al., "Thermoacoustic computed tomography using a conventional linear transducer array," Medical Physics, 30(5): 856-860 (2003).

Kruger, et al., "Thermoacoustic Molecular Imaging of Small Animals," Molecular Imaging, 2(2): 113-123 (2003).

Kruger, et al., "Thermoacoustic CT: imaging principles," Proc. SPIE 3916, (2000) pp. 150-160.

Kruger, et al., "Breast Cancer in Vivo: Contrast Enhancement with Thermoacoustic CT at 434 MHz-Feasibility Study," Radiology, 216(1): 279-283 (2000).

Ku and Wang, "Scanning thermoacoustic tomography in biological tissue." Medical physics 27.5 (2000): 1195-1202.

Ku and Wang, "Scanning microwave-induced thermoacoustic tomography: Signal, resolution, and contrast," Medical Physics, 28(1): 4-10 (2001).

Ku, G. et al., "Multiple-bandwidth photoacoustic tomography," Physics in Medicine & Biology, 49(7): 1329-1338 (2004).

Ku and Wang, "Deeply penetrating photoacoustic tomography in biological tissues enhanced with an optical contrast agent," Optics Letters, 30(5): 507-509 (2005).

Ku, et al., "Imaging of tumor angiogenesis in rat brains in vivo by photoacoustic tomography," Applied Optics, 44(5): 770-775 (2005).

Ku, et al., "Thermoacoustic and Photoacoustic Tomography of Thick Biological Tissues Toward Breast Imaging," Technology in Cancer Research & Treatment, 4(5): 559-566 (2005).

Kunitz, M., "Crystalline desoxyribonuclease; isolation and general properties; spectrophotometric method for the measurement of desoxyribonuclease activity," The Journal General Physiology, vol. 33, Mar. 20, 1950, pp. 349-362. <URL:http://doi.org./10.1085/jgp.33.4.349>.

Lai, S. et al., "Mucus-penetrating nanoparticles for drug and gene delivery to mucosal tissues," Adv. Drug Deliv. Rev. 61(2), Feb. 27, 2009, pp. 158-171. <doi:10.1016/j.addr.2008.11.002>.

Lai, P. et al., "Photoacoustically guided wavefront shaping for enhanced optical focusing in scattering media," Nature Photonics 9 126-132 (Jan. 19, 2015).

Lai, P. et al., "Dependence of optical scattering from Intralipid in gelatin-gel based tissue-mimicking phantoms on mixing temperature and time" Journal of Biomedical Optics, vol. 19, No. 3, Mar. 2014, pp. 035002-1-035602-6.

Larina, et al., Real-time optoacoustic monitoring of temperature in tissues: Journal of Physics D: Applied Physics, vol. 38, (2005) pp. 2633-2639.

Lasch, et al., "FT-IR spectroscopic investigations of single cells on the subcellular level," Vibr. Spectrosc. 28, 147-157 (2002).

Laser Institute of America, "American National Standard for the safe use of lasers," American National Standard Institute (ANSI Z136.1-2007 Revision of ANSI Z136.1-2000).

(56) References Cited

OTHER PUBLICATIONS

Leal, et al., "Physicochemical properties of mucus and their impact on transmucosal drug delivery," Int. J. Pharm. 532, (2017) pp. 555-572.
Lewis, E. N. et al., "Fourier transform spectroscopic imaging using an infrared focal-Plane array detector," Anal. Chem. 67, 3377-3381 (1995).
Leitgeb, et al., "Performance of fourier domain vs. time domain optical coherence tomography," Optical Express, vol. 11, No. 8, Apr. 21, 2003, pp. 889-894.
Li, et al., "An Enteric Micromotor Can Selectively Position and Spontaneously Propel in the Gastrointestinal Tract," ACS Nano. 10(10), Oct. 25, 2016, pp. 9536-9542. <doi:10.1021/acsnano.6b04795>.
Li, et al., "Autonomous Collision-Free Navigation of Microvehicles in Complex and Dynamically Changing Environments" ACS Nano, 11, (2017) pp. 9268-9275.
Li, G., et al., "Reflection-mode multifocal optical-resolution photoacoustic microscopy," J. Biomed. Opt. 18, 030501 (Feb. 12, 2013).
Li, L., et al., "Small near-infrared photochromic protein for photoacoustic multi-contrast imaging and detection of protein interactions in vivo," Nature Communications 9(1) 2734 (Jul. 16, 2018).
Li, et al., "Single-impulse panoramic photoacoustic computed tomography of small-animal whole-body dynamics at high spatiotemporal resolution," Nat Biomed Eng. 1(5) May 2017, pp. 1-11. <doi:10.1038/s41551-017-0071>.
Li, L.., et al., "Simultaneous Molecular and Hypoxia Imaging of Brain Tumors in Vivo Using Spectroscopic Photoacoustic Tomography," Proceedings of the IEEE, 96(3): 481-489 (2008).
Li, J. et al., "Micro/Nanorobots for Biomedicine: Delivery, Surgery, Sensing, and Detoxification" Sci Robot, 2(4), Mar. 15, 2017, pp. 1-20. <doi:10.1126/scirobotics.aam6431>.
Li, Y. et al., "Multifocal photoacoustic microscopy through an ergodic relay (Conference Presentation)", Proc. SPIE 10878, Photons Plus Ultrasound: Imaging and Sensing 2019, 108781C, presented Feb. 4, 2019, published Mar. 4, 2019, https://doi.org/10.1117/12.2513502.
Li, et al., "Optical Coherence Computed Tomography," Applied Physics Letters, vol. 91, American Institute of Physics, 2007, pp. 141107-1-141107-3.
Li, et al., "Snapshot photoacoustic topography through an ergodic relay for high-throughput imaging of optical absorption," Nature Photonics, Jan. 20, 2020. <URL:https://doi.org/10.1038/s41566-019-0576-2>.
Li, Z., et al., "Super-resolution far-field infrared imaging by photothermal heterodyne imaging," The Journal of Physical Chemistry B, vol. 121 (2017) pp. 8838-8846.
Li, Z., et al., "Super-resolution imaging with mid-IR photothermal microscopy on the single particle level," In Proceedings of SPIE Physical Chemistry of Interfaces and Nano-materials XIV, vol. 9549, Aug. 20, 2015, pp. 9549121-954912-8.
Liang, et al., "Single-shot real-time femtosecond imaging of temporal focusing," Light-Science & Applications 7(1) 42 (Aug. 8, 2018).
Liang, et al., "Single-shot real-time video recording of a photonic Mach cone induced by a scattered light pulse," Science Advances 3(1) e1601814 (Jan. 20, 2017).
Liang, et al., "Single-shot ultrafast optical imaging," Optica 5(9) 1113-1127 (Sep. 2018).
Lin, et al., "Single-breath-hold photoacoustic computed tomography of the breast," Nature Communications 9(1) 2352 (Jun. 15, 2018).
Liu, et al., "Optical focusing deep inside dynamic scattering media with near-infrared time-reversed ultrasonically encoded (TRUE) light," Nature Communications 6 5409 (Jan. 5, 2015).
Liu, et al., "Label-free cell nuclear imaging by Grüneisen relaxation photoacoustic microscopy" Opt Lett. Feb. 15, 2018; 43(4), (2018) pp. 947-950.
Lovell, et al., "Porphysome nanovesicles generated by porphyrin bilayers for use as multimodal biophotonic contrast agents," Nature Materials 10(4) 324-32 (Mar. 20, 2011).
Lu, F., et al., "Tip-enhanced infrared nanospectroscopy via molecular expansion force detection," Nat. Photon. 8, 307-312 (2014).
Lu, F.-K. et al., "Label-free DNA imaging in vivo with stimulated Raman scattering microscopy," Proc. Natl Acad Sci. USA 112, 11624-11629 (2015).
Ma, et al., "Time-reversed adapted-perturbation (TRAP) optical focusing onto dynamic objects inside scattering media," Nature Photonics 8(12) 931-936 (Nov. 2, 2014).
Manohar, et al., "Initial results of in vivo non-invasive cancer imaging in the human breast using near-infrared photoacoustics," Optics Express, 15(19): 12277-12285 (2007).
Maslov, et al., "In vivo dark-field reflection-mode photoacoustic microscopy," Optics Letters 30(6), Mar. 15, 2005, pp. 625-627.
Maslov, et al., "Photoacoustic Imaging of biological tissue with Intensity-Modulated Continuous-Wave Laser" Journal of Biomedical Optics, 2008, pp. 024006 1-5, vol. 13(2), SPIE, USA.
Medina-Sanchez, et al., "Medical microbots need better imaging and control," Nature 545, (2017) pp. 406-408.
Michaelian, Kirk H. Photoacoustic IR spectroscopy: instrumentation, applications and data analysis. Pub: John Wiley & Sons; Dec. 1, 2010. <Preface Only>.
Miller, et al., "Synchrotron-based biological microspectroscopy: From the mid-infrared through the far-infrared regimes," Journal of Biological Physics 29, 219-230 (2003).
Mishra et al., "Development and comparison of the DTM, the DOM and the FVM formulations for the short-pulse laser transport through a participating medium" International Journal of Heat and Mass Transfer, vol. 49 (2006) pp. 1820-1832.
Montaldo, et al., "Building three-dimensional images using time-reversal chaotic cavity", IEEE Trans. Ultrason. Ferroelectr. Freq. Control 52, pp. 1489-1497 (2005).
Morgner et al., "Spectroscopic optical coherence tomography," Optics Letters, vol. 25, No. 2, Jan. 15, 2000, pp. 111-113.
Murray et al., "High-Sensitivity Laser-Based Acoustic Microscopy Using a Modulated Excitation Source," Applied Physics Letters, vol. 85, No. 14, American Institute of Physics, USA., Oct. 4, 2004, pp. 2974-2976.
Nakajima, et al., "Three-dimensional analysis and classification of arteries in the skin and subcutaneous adipofascial tissue by computer graphics imaging," Plastic and Reconstructive Surgery, 102(3): 748-760 (1998).
Nasiriavanaki, et al., "High-resolution photoacoustic tomography of resting-state functional connectivity in the mouse brain," Proceedings of the National Academy of Sciences 111(1) 21-26 (Jan. 7, 2014).
Nasse, M. J. et al., "High-resolution Fourier-transform infrared chemical imaging with multiple synchrotron beams," Nat. Methods 8, 413-416 (2011).
Nelson et al., "Imaging Glioblastoma Multiforme," The Cancer Journal vol. 9, No. 2, Mar./Apr. 2003, pp. 134-145.
Niederhauser et al., "Combined Ultrasound and Optoacoustic System for Real-Time High-Contrast Vascular imaging in Vivo," IEEE Transactions on MedicalImaging, 24(4): 436-440 (2005).
Nowak, D. et al., "Nanoscale chemical imaging by photoinduced force microscopy," Sci. Adv. 2, Mar. 25, 2016, e1501571, pp. 1-9.
Ntziachristos, V., "Going deeper than microscopy: the optical imaging frontier in biology" Nature Methods vol. 7, No. 8, Aug. 2010, pp. 603-614.
Oraevsky et al., "Optoacoustic Tomography," Biomedical Photonics Handbook, 2003, chapter 34: pp. 931-964, CRC Press LLC, USA.
Oraevsky et al., "Ultimate Sensitivity of Time-Resolved Opto-Acoustic Detection," Biomedical Optoacoustics, 2000, pp. 228-239, vol. 3916, SPIE, USA.
Oraevsky et al., "Laser Optoacoustic Tomography of Layered Tissues: Signal Processing" Proceedings of SPIE, 2979: 59-70 (1997).
Oraevsky et al.,, "Laser opto-acoustic imaging of the breast: Detection of cancer angiogenesis" Proceedings of SPIE, 3597: 352-363 (1999).

(56) References Cited

OTHER PUBLICATIONS

Patel, et al., "Pulsed optoacoustic spectroscopy of condensed matter," Rev. Mod. Phys., vol. 53 (1981) pp. 517-550.
Paxton, et al., "Catalytic nanomotors: Autonomous movement of striped nanorods," J. Am. Chem. Soc. 126, 13424-13431 (2004).
Petrov, et al., "Optoacoustic, Noninvasive, Real-Time, Continuous Monitoring of Cerebral Blood Oxygenation: An In Vivo Study in Sheep" Anesthesiology, vol. 102, No. 1, Jan. 2005, pp. 69-75.
Potter, et al., "Capillary diameter and geometry in cardiac and skeletal muscle studied by means of corrosion casts" Microvascular Research, 25(1): 68-84 (1983).
Prati, et al., "New advances in the application of FTIR microscopy and spectroscopy for the characterization of artistic materials," Accounts of Chemical Research, vol. 43, (2010) pp. 792-801.
Prevedel, et al., "Simultaneous whole-animal 3D imaging of neuronal activity using light-field microscopy," Nat. Methods 11, 727-730 (Jul. 2014).
Quickenden, et al., "The ultraviolet absorption spectrum ofliquid water," J Chem. Phys. 72, 4416-4428 (1980).
Razansky, et al., "Multispectral opto-acoustic tomography of deep-seated fluorescent proteins in vivo," Nature Photonics 3, (2009) pp. 412-417.
Robert et al., "Fabrication of Focused Poly (Vinylidene Fluoride-Trifluoroethylene) P19 (VDF-TrFE) Copolymer 40-50 MHz Ultrasound Transducers on Curved Surfaces," Journal of Applied Physics, vol. 96, No. 1. Jul. 1, 2004, pp. 252-256.
Rockley, M.G., "Fourier-transformed infrared photoacoustic spectroscopy of polystyrene film," Chem. Phys. Lett. 68, 455-456 (1979).
Rosenblum, et al., "Progress and challenges towards targeted delivery of cancer therapeutics" Nat. Commun. 9, (2018) 1410, pp. 1-12.
Saager et al., "Direct characterization and removal of interfering absorption trends in two-layer turbid media" J. Opt. Soc. Am. A, vol. 22, No. 9, Sep. 2005, pp. 1874-1882.
Sanchez, et al., "Chemically powered micro- and nanomotors," Angew. Chem. Int. Ed. 54, (2015) pp. 1414-1444.
Sakadzic, et al., "Correlation transfer and diffusion of ultrasound-modulated multiply scattered light," Physical Review Letters 96(16) 163902—(1-4) (Apr. 28, 2006).
Savateeva, et al., "Noninvasive detection and staging or oral cancer in vivo with confocal opto-acoustic tomography" Biomedical Optoacoustics, vol. 3916, International Society for Optics and Photonics 2000, pp. 55-66.
Schambach, et al., "Application of micro-CT in small animal imaging" Methods, vol. 50, No. 1, Jan. 2010, pp. 2-13.
Schmidt, et al., "A 32-Channel Time Resolved Instrument for Medical Optical Tomography" Review of Scientific Instruments, vol. 71, No. 1, Jan. 2000, pp. 256-265.
Schroeter, et al., "Spontaneous slow hemodynamic oscillations are impaired in cerebral microangiopathy," Journal of Cerebral Blood Flow & Metabolism (2005) 25, pp. 1675-1684.
Servant, et al., "Controlled In Vivo Swimming of a Swarm of Bacteria-Like Microrobotic Flagella" Advanced Materials 27, (2015) pp. 2981-2988.
Sezer, et al., "Review of magnesium-based biomaterials and their applications," J. Magnesium Alloys 6, (2018) pp. 23-43.
Sethuraman et al., "Development of a combined intravascular ultrasound and photoacoustic imaging system" Proceedings of SPIE, 6086: 60860F.1-60860F.10 (2006).
Sethuraman et al., "Intravascular photoacoustic imaging of atherosclerotic plaques: Ex vivo study using a rabbit model of atherosclerosis" Proceedings of SPIE, 6437: 643729.1-643729.9 (2007).
Shah, J. et al, "Photoacoustic imaging and temperature measurement for photothermal cancer therapy," Journal of Biomedical Optics, vol. 13, No. 3, (May/Jun. 2008) pp. 034024-1-034024-9.
Sheth, et al., "Columnar Specificity of Microvascular Oxygenation and Volume Responses: Implications for Functional Brain Mapping," The Journal of Neuroscience, vol. 24, No. 3, Jan. 21, 2004, pp. 634-641.
Shi, J., et al., "High-resolution, high-contrast mid-infrared imaging of fresh biological samples with ultraviolet-localized photoacoustic microscopy," Nature Photonics 13 609-615 (May 2019).
Shmueli, et al., "Low Frequency Fluctuations in the Cardiac Rate as a Source of Variance in the Resting-State fMRI BOLD Signal," Neuroimage, vol. 38, No. 2, Nov. 1 2007, pp. 306-320.
Silva, et al., "Toward Label-Free Super-Resolution Microscopy," ACS Photon. 3, 79-86 (2016).
Sim, et al., "In vivo Microscopic Photoacoustic Spectroscopy for Non-Invasive Glucose Monitoring Invulnerable to Skin Secretion Products," Sci. Rep. 8, 1059 (2018).
Siphanto et al., "Imaging of Small Vessels Using Photoacoustics: an in Vivo Study," Lasers in Surgery and Medicince, vol. 35, Wiley-Liss, Inc., Netherlands, Dec. 20, 2004, pp. 354-362.
Sitti, M., "Miniature soft robots-road to the clinic," Nat. Rev. Mater, 3, (2018) pp. 74-75.
Smith, et al., "Beyond C, H, O, and Ni analysis of the elemental composition of U.S. FDA approved drug architectures," J. Med. Chem. 57, pp. 9764-9773 (2014).
Sommer, A. J., et al., "Attenuated total internal reflection infrared mapping microspectroscopy using an imaging microscope," Appl. Spectrosc. 55, 252-256 (2001).
Song, et al., "Fast 3-D dark-field reflection-mode photoacoustic microscopy in vivo with a 30-MHz ultrasound linear array" Journal of Biomedical Optics, 13(5): 054028.1-054028.5 (2008).
Song et al., "Multi-focal optical-resolution photoacoustic microscopy in vivo." NIH Public Access Author Manuscript, May 13, 2011. pp. 1-7.
Song, et al., "Section-illumination photoacoustic microscopy for dynamic 3D imaging of microcirculation in vivo" Optics Letters, 35(9): 1482-1484 (2010).
Soppimath, et al., "Microspheres as floating drug-delivery systems to increase gastric retention of drugs" Drug Metab. Rev. 33, (2001) pp. 149-160.
Steinbrink, et al., "Illuminating the BOLD signal: combined fMRI-fNIRS studies" Magnetic Resonance Imaging, vol. 24, No. 4, May 2006, pp. 495-505.
Stern, MD., "In vivo evaluation of microcirculation by coherent light scattering," Nature, 254(5495): 56-58 (1975).
Tay, et al., "Magnetic Particle Imaging Guided Heating In Vivo using Gradient Fields for Arbitrary Localization of Magnetic Hyperthermia Therapy" ACS Nano. 12(4), Apr. 24, 2018, pp. 3699-3713. <doi:10.1021/acsnano.8b00893>.
Tam, A. C., "Applications of photoacoustic sensing techniques," Reviews of Modern Physics, vol. 58, No. 2, Apr. 1986, pp. 381-431.
Tearney, et al., "Scanning single-mode fiber optic catheter-endoscope for optical coherence tomography" Optics Letters, 21(7): 543-545 (1996).
Tran, et al., "In vivo endoscopic optical coherence tomography by use of a rotational microelectromechanical system probe" Optics Letters, 29(11): 1236-1238(2004).
Tu, et al., "Self-propelled supramolecular nanomotors with temperature-responsive speed regulation," Nat. Chem. 9, 480 (2016).
Van Essen, et al., "An Integrated Software Suite for Surface-based Analyses of Cerebral Cortex" Journal of the American Medical Informatics Association, vol. 8, No. 5, Sep./Oct. 2001, pp. 443-459.
Velasco, E., "Ultrafast Camera Takes 1 Trillion Frames Per Second of Transparent Objects and Phenomena" [Webpage] Caltech, California Institute of Technology, Jan. 17, 2020, pp. 1-2. <URL:https://www.eurekalert.org/pub_releases/2020-01/ciot-uct012120.php>.
Viator et al., "Design testing of an endoscopic photoacoustic probe for determination of treatment depth after photodynamic therapy" Proceedings of SPIE in Biomedical Optoacoustics II, 4256: 16-27 (2001).
Vilela, et al., "Medical imaging for the tracking of micromotors," ACS Nano 12, (2018) pp. 1220-1227.
Wang, et al., "Ballistic 2-D Imaging Through Scattering Walls Using an Ultrafast Oplical Kerr Gale," Science, vol. 253, Aug. 16, 1991, pp. 769-771.
Wang, et al., "Biomedical Optics, Principles and Imaging," Wiley-Interscience, A John Wiley & Sons, Inc., (2007) p. 7.
Wang, et al., "Fabrication of micro/nanoscale motors" Chem. Rev. 115, (2015) pp. 8704-8735.

(56) References Cited

OTHER PUBLICATIONS

Wang, L. et al., "Grueneisen relaxation photoacoustic microscopy," Physical Review Letters 113 174301 (Oct. 24, 2014).
Wang, L. V & Yao, J., "A practical guide to photoacoustic tomography in the life sciences," Nat. Methods 13, 627-638 (Jul. 28, 2016).
Wang, L. V., "Multiscale photoacoustic microscopy and computed tomography," Nat. Photon. 3, 503-509 (Aug. 29, 2009).
Wang, L. V.; "Mechanisms of ultrasonic modulation of multiply scattered coherent light: an analytic model," Physical Review Letters 87(4) 043903—(1-4) (Jul. 23, 2001).
Wang, L. V.; "Prospects of photoacoustic tomography," Medical Physics 35(12), Nov. 19, 2008, pp. 5758-5767.
Wang, L., et al., "Single-cell label-free photoacoustic flowoxigraphy in vivo," Proceedings of the National Academy of Sciences 110(15) 5759-5764 (Apr. 9, 2013).
Wang, L., et al., "Ultrasonically encoded photoacoustic flowgraphy in biological tissue," Physical Review Letters 111(20), 204301 (Nov. 15, 2013).
Wang, L.V., Hu, S. "Photoacoustic Tomography: in vivo imaging from organelles to organs," Science 335, 1458-1462 (Mar. 23, 2012).
Wang, X. D., et al., "Noninvasive laser-induced photoacoustic tomography for structural and functional in vivo imaging of the brain," Nature Biotechnology 21(7) 803-806 (Jul. 2003).
Wang, et al., "MCML—Monte Carlo modeling of light transport in multi-layered tissues" Computer Methods and Programs in Biomedicine, vol. 47, No. 2, Jul. 1995, pp. 131-146.
Wang et al., "Three-dimensional laser-induced photoacoustic tomography of mouse brain with the skin and skull intact," Optics Letters, 28(19): 1739-1741 (2003).
Wang et al., "Noninvasive photoacoustic angiography of animal brains in vivo with near-infrared light and an optical contrast agent" Optics Letters, 29(7): 730-732 (2004).
Wang, et al., "Intravascular Photoacoustic Imaging" IEEE J Quantum Electronics, 16(3): 588-599 (2010).
Wang, et al., "Nano/microscale motors: biomedical opportunities and challenges," ACS Nano 6, (2012) pp. 5745-5751.
Wetzel, et al., "Imaging molecular chemistry with infrared microscopy," Science, New Series, vol. 285, No. 5431, Aug. 20, 1999, pp. 1224-1225.
Wong, T. et al., "Fast label-free multilayered histology-like imaging of human breast cancer by photoacoustic microscopy," Sci. Adv. 3, 1602168 (May 17, 2017).
Wong, T. et al., "Label-free automated three-dimensional imaging of whole organ by microtomy-assisted photoacoustic microscopy," Nat. Comm. 8, (Nov. 9, 2017).
Wu, Z., et al., "A microrobotic system guided by photoacoustic computed tomography for targeted navigation in intestines in vivo," Science Robotics 4(32) eaax0613 (Jul. 24, 2019).
Wu, D., et al., "In vivo Mapping of Macroscopic Neuronal Projections in the Mouse Hippocampus using High-resolution Diffusion MRI," Neuroimage 125, Jan. 15, 2016, pp. 84-93.
Xia, J., et al., "Photoacoustic tomography: principles and advances," Electromagn. Waves 147, 1 (2014; available in PMC Jan. 30, 2015).
Xia, J., et al., "Wide-field two-dimensional multifocal optical-resolution photoacoustic-computed microscopy," Opt. Lett. 38(24), Dec. 15, 2013, pp. 5236-5239.
Xu, et al., "Photoacoustic Imaging in Biomedicine," Review of Scientific Instruments, American Institute of Physics, vol. 77 (2006) pp. 041101 1-22.
Xu, et al., "Rhesus monkey brain imaging through intact skull with thermoacoustic tomography," IEEE Trans. Ultrason. Ferroelectr. Freq. Control, vol. 53, No. 3, Mar. 2006, pp. 542-548.
Xu, M. H.; Wang, L. V.; "Time-domain reconstruction for thermoacoustic tomography in a spherical geometry," IEEE Transactions on Medical Imaging 21(7) 814-822 (Jul. 2002).
Xu, M. H.; Wang, L. V.; "Universal back-projection algorithm for photoacoustic computed tomography," Physical Review E 71(1) 016706-(1-7) (Jan. 19, 2005).

Xu, S., et al., "Thermal expansion of confined water," Langmuir 25, 5076-5083 (2009).
Xu, X. et al., "Time-reversed ultrasonically encoded optical focusing into scattering media," Nature Photonics 5(3) 154-157 (Jan. 16, 2011).
Xu, Y.; Wang, L. V.; "Time reversal and its application to tomography with diffracting sources," Physical Review Letters 92(3) 033902—(1-4) (Jan. 23, 2004).
Xu et al.. "Time Reversal Ultrasound Modulated Optical Tomography Using a BSO Phase Conjugate Mirror," poster presented at SIPE Conference 7177 on Jan. 26, 2009, 1 page.
Yadlowsky, et al., "Multiple scattering in optical coherence microscopy" Applied Optics, vol. 34, No. 25 (1995) pp. 5699-5707. <doi.org/10.1364/AO.34.005699>.
Yan, et al., "Multifunctional biohybrid magnetite microrobots for imaging-guided therapy" Yan et al., Sci. Robot. 2, eaaq1155, Nov. 22, 2017, pp. 1-14.
Yang, "Optical coherence and Doppler tomography for monitoring tissue changes induced by laser thermal therapy—An in vivo feasibility study" Review of Scientific Instruments , vol. 74, No. 1, Jan. 2003, p. 437-440.
Yang, J. M. et al., "Simultaneous functional photoacoustic and ultrasonic endoscopy of internal organs in vivo," Nature Medicine 18(8) 1297-1303 (Aug. 2012).
Yang, J., et al., "Motionless volumetric photoacoustic microscopy with spatially invariant resolution," Nature Communications 8(1) 780 (Oct. 3, 2017).
Yang, et al., "Novel biomedical imaging that combines intravascular ultrasound (IVUS) and optical coherence tomography (OCT)" IEEE International Ultrasonics Symposium, Beijing, China, Nov. 2-5, 2008, pp. 1769-1772.
Yang, et al., "Time-reversed ultrasonically encoded optical focusing using two ultrasonic transducers for improved ultrasonic axial resolution" Journal of Biomedical Optics 18(11), 110502 (Nov. 2013) pp. 110502-1-110502-4.
Yang, et al., "The grand challenges of science robotics," Science Robotics 3, Jan. 31, 2018, eaar7650, pp. 1-14.
Yao, et al., "Monte Carlo simulation of an optical coherence tomography signal in homogeneous turbid media" Phys. Med. Biol. 44(9), Jul. 8, 1999, pp. 2307-2320.
Yao, et al., "Absolute photoacoustic thermometry in deep tissue," Opt. Lett. 38, 5228-5231 (2013).
Yao, et al., "In vivo label-free photoacoustic microscopy of cell nuclei by excitation of DNA and RNA," Opt. Lett. 35, 4139-4141 (2010).
Yao, et al., "Optimal ultraviolet wavelength for in vivo photoacoustic imaging of cell nuclei," J Biomed. Opt. 17, 056004 (2012).
Yao, et al., "Photoimprint photoacoustic microscopy for three-dimensional label-free sub-diffraction imaging," Physical Review Letters 112(1) 014302 (Jan. 10, 2014).
Yao, L. et al., "Multiscale photoacoustic tomography using reversibly switchable bacterial phytochrome as near-infrared photochromic probe," Nature Methods 13(1) 67-73 (Jan. 2016).
Yao, L. et al., "High-speed label-free functional photoacoustic microscopy of mouse brain in action," Nat. Methods 12(5), 407-410 (May 12, 2015).
Yao, L. et al., "Photoacoustic microscopy: superdepth, superresolution, and superb contrast", IEEE Pulse 6, 34-7 (May 13, 2015).
Yaqoob, et al., "Methods and application areas of endoscopic optical coherence tomography" Journal of Biomedical Optics, 11(6): 063001.1-063001.19 (2006).
Yavuz, M. S., et al., "Gold nanocages covered by smart polymers for controlled release with near-infrared light," Nature Materials 8(12) 935-939 (Nov. 1, 2009).
Yin, et al., "Agarose particle-templated porous bacterial cellulose and its application in cartilage growth in vitro" Acta Biomater. 12, Jan. 2015, pp. 129-138. <doi:10.1016/j.actbio.2014.10.019>.
Yodh et al., "Functional Imaging with Diffusing Light" Biomedical Photonics Handbook, 2003, Ch. 21 , pp. 45, CRC Press, Boca Raton.
Yodh, et al. "Spectroscopy and Imaging with Diffusing Light" Physics Today 48(3), Mar. 1995, pp. 34-40.

(56) References Cited

OTHER PUBLICATIONS

Zeff, et al., "Retinotopic mapping of adult human visual cortex with high-density diffuse optical tomography" PNAS, vol. 104, No. 29, Jul. 17, 2007, pp. 12169-12174.
Zemp, et al., "Realtime photoacoustic microscopy in vivo with a 30MHZ ultrasonic array transducer" Optics Express, 16(11): 7915-7928 (2008).
Zhang, C., et al., "Coherent Raman scattering microscopy in biology and medicine," Annu. Rev. Biomed. Eng. 17, 415-445 (2015).
Zhang, D. et al., "Depth-resolved mid-infrared photothermal imaging of living cells and organisms with submicrometer spatial resolution," Sci. Adv. 2, e1600521 (2016).
Zhang, H. F. et al., "Functional photoacoustic microscopy for high-resolution and noninvasive in vivo imaging," Nature Biotechnology 24(7) 848-851 (Jul. 2006).
Zhang, H. F. et al., "In vivo imaging of subcutaneous structures using functional photoacoustic microscopy," Nature Protocols 2(4) 797-804 (Apr. 5, 2007).
Zhang, et al., "Intrinsic Functional Relations Between Human Cerebral Cortex and Thalamus" Journal of Neurophysiology, vol. 100, No. 4, Oct. 2008, pp. 1740-1748.
Zharov, et al., "In vivo photoacoustic flow cytometry for monitor of circulating single cancer cells and contrast agents," Optics Letters, 31(24): 3623-3625 (2006).
Zou, et al., "BOLD responses to visual stimulation in survivors of childhood cancer" NeuroImage, vol. 24, No. 1, Jan. 1, 2005, pp. 61-69.
U.S. Appl. No. 16/946,496, filed Jun. 24, 2020, Gao et al.
U.S. Appl. No. 16/611,939, filed Nov. 8, 2019, Wang et al.
Notice of Allowance dated Oct. 28, 2020 issued in U.S. Appl. No. 15/037,468.
Office Action dated Oct. 8, 2020 issued in U.S. Appl. No. 16/372,597.
International Search Report and Written Opinion dated Aug. 31, 2020, issued in Application No. PCT/US2020/019368.
International Search Report and Written Opinion dated Oct. 14, 2020, issued in Application No. PCT/US2020/07174.
Arridge, et al., "Accelerated high-resolution photoacoustic tomography via compressed sensing," ArXiv Prepr. ArXiv160500133, 2016, pp. 8908-8940.
Cox, et al., "Artifact trapping during time reversal photoacoustic imaging for acoustically heterogeneous media," IEEE Trans. Med. Imaging, vol. 29, No. 2, (2010) pp. 387-396.
Deán-Ben, et al., "Functional optoacoustic neuro-tomography for scalable whole-brain monitoring of calcium indicators," Light Sci. Appl., vol. 5, No. 12, p. e16201, 2016, pp. 1-7.
Deán, et al., "Portable spherical array probe for volumetric real-time optoacoustic imaging at centimeter-scale depths," Opt. Express, vol. 21, No. 23, 2013, pp. 28062-28071.
Deserno, M., "How to generate equidistributed points on the surface of a sphere," Polym. Ed, p. 99, 2004, p. 1.
Han, Y. et al., "Three-dimensional optoacoustic reconstruction using fast sparse representation," Opt. Lett., vol. 42, No. 5, (2017) pp. 979-982.
Han, et al., "Optoacoustic image reconstruction and system analysis for finite-aperture detectors under the wavelet-packet framework," J. Biomed. Opt., vol. 21, No. 1, Jan. 2016, pp. 016002-1-016002-9.
Huang, et al., "Full-wave iterative image reconstruction in photoacoustic tomography with acoustically inhomogeneous media," IEEE Trans. Med. Imaging, vol. 32, No. 6, Jun. 2013, pp. 1097-1110.
Karshalev, E. et al., "Micromotor Pills as a Dynamic Oral Delivery Platform" American Chemical Society Nano, 2018, vol. 12, No. 8, pp. 8397-8405 <DOI: 10.1021/acsnano.8b03760>.
R. A. Kruger, et al., "Dedicated 3D photoacoustic breast imaging," Med. Phys., vol. 40, No. 11, 2013, pp. 113301-1-113301-8.
Kuppusami, S. et al., "Parylene Coatings in Medical Devices and Implants: A Review" Universal Journal of Biomedical Engineering, 2015, vol. 3, No. 2, pp. 9-14 <DOI: 10.13189/ujbe.2015.030201>.
Li, J. et al., "Micromotors Spontaneously Neutralize Gastric Acid for pH-Responsive Payload Release" Angewandte Chemie International Edition, vol. 56, No. 8, 2017 pp. 2156-2161. <DOI: 10.1002/anie.201611774>.
Maslov, et al., "Optical-resolution photoacoustic microscropy for in vivo imaging of single capillaries," Optical Letters, 33(9): 929-931 (2008).
Matthews, et al., "Parameterized Joint Reconstruction of the Initial Pressure and Sound Speed Distributions for Photoacoustic Computed Tomography," Siam J. Imaging Sci., vol. 11, No. 2, (2018) pp. 1560-1588.
Matsumoto, et al., "Label-free photoacoustic imaging of human palmar vessels: a structural morphological analysis," Sci. Rep., vol. 8, No. 1, (2018) p. 786.
Mitsuhashi, et al., "A forward-adjoint operator pair based on the elastic wave equation for use in transcranial photoacoustic computed tomography," Siam J. Imaging Sci., vol. 10, No. 4, 2017, pp. 2022-2048.
Mitsuhashi, et al., "Investigation of the far-field approximation for modeling a transducer's spatial impulse response in photoacoustic computed tomography," Photoacoustics, vol. 2, No. 1, 2014, pp. 21-32.
Ogunlade, et al., "In vivo three-dimensional photoacoustic imaging of the renal vasculature in preclinical rodent models," Am. J. Physiol.-Ren. Physiol., vol. 314, No. 6, (2018) pp. F1145-F1153.
Pramanik, M., "Improving tangential resolution with a modified delayand-sum reconstruction algorithm in photoacoustic and thermoacoustic tomography," JOSA A, vol. 31, No. 3, (2014) pp. 621-627.
Scholte, et al., "On spatial sampling and aliasing in acoustic imaging" 12th Intern. congress on sound and vibration, Lisbon, Portugal (2005) pp. 1-8.
Schoeder, et al., "Optoacoustic image reconstruction: the full inverse problem with variable bases," Proc. R. Soc. A, vol. 474, No. 2219, (2018) pp. 1-20.
Treeby, et al., "k-Wave: Matlab toolbox for the simulation and reconstruction of photoacoustic wave fields," J. Biomed. Opt., vol. 15, No. 2, Mar./Apr. 2010, pp. 021314.
Treeby, et al., "Advanced photoacoustic image reconstruction using the k-Wave toolbox," in Photons Plus Ultrasound: Imaging and Sensing 2016, 2016, vol. 9708, p. 97082P.
Tzoumas, et al., "Eigenspectra optoacoustic tomography achieves quantitative blood oxygenation imaging deep in tissues," Nat. Commun., vol. 7, 2016, pp. 1-10.
Wang et al., "Biomedical optics: principles and imaging," Section 12.5; Photoacoustic Tomography, John Wiley & Sons (2012) pp. 288-290.
Wang, B. et al., "Recent progress on micro- and nano-robots: towards in vivo tracking and localization" Quantitative Imaging in Medicine and Surgery, 2018, vol. 8, No. 5, pp. 461-479. <DOI: 10.21037/qims.2018.06.07>.
Wang, K. et al., "Investigation of iterative image reconstruction in three-dimensional optoacoustic tomography," Phys. Med. Biol., vol. 57, No. 17, 2012, pp. 5399-5423.
Xu, et al., "Exact frequency-domain reconstruction for thermoacoustic tomography-II: Cylindrical geometry," IEEE Trans. Med. Imaging, vol. 21, No. 7, (2002) pp. 829-833.
Yang, J.M., et al., "Focusing light inside live tissue using reversibly switchable bacterial phytochrome as a genetically encoded photochromic guide star" Science Advances 5(12) (2019) pp. 1-9.
Zhou, et al., "Tutorial on photoacoustic tomography," J. Biomed. Opt., vol. 21, No. 6, Jun. 2016, pp. 061007-1-061007-14.
U.S. Appl. No. 17/090,752, filed Nov. 5, 2020, Wang et al.

* cited by examiner

TRANSCRANIAL PHOTOACOUSTIC/THERMOACOUSTIC TOMOGRAPHY BRAIN IMAGING INFORMED BY ADJUNCT IMAGE DATA

RELATED APPLICATIONS

This application is a National Stage of International Application No. PCT/US2013/065594, filed on Oct. 18, 2013, which claims to the benefit of U.S. Provisional Application 61/762,415, filed on Feb. 8, 2013, and to U.S. Provisional Application 61/715,671, filed on Oct. 18, 2012, of which all contents are hereby incorporated herein in their entirety.

GOVERNMENTAL RIGHTS IN THE INVENTION

This invention was made with government support under Grant Nos. EB010049, EB009715, CA134539, EB000712, CA136398, and EB008085 awarded by the National Institutes of Health. The government has certain rights in the invention.

FIELD OF THE INVENTION

The invention generally relates to systems and methods for transcranial photoacoustic imaging of the brain using adjunct image data.

BACKGROUND OF THE INVENTION

Existing high-resolution human brain imaging modalities such as X-ray computed tomography (CT) and magnetic resonance imaging (MRI) are expensive and employ bulky and generally non-portable imaging equipment. Moreover, X-ray CT employs ionizing radiation and is therefore undesirable for use with patients who require frequent monitoring of brain diseases or injuries. Alternatively, ultrasonography is an established portable pediatric brain imaging modality, but its image quality degrades severely when employed after the closure of the fontanels and therefore is not effective for imaging adults. The development of thermoacoustic tomography (TAT) and photoacoustic tomography (PAT) brain imaging methods may circumvent these limitations and may potentially provide a powerful new brain imaging modality that would fill an important void left by existing techniques.

Transcranial brain imaging may benefit significantly by the application of advanced PAT imaging methods. Photoacoustic tomography is a hybrid ultrasound-mediated biophotonic imaging modality that combines the high contrast of optical imaging with the high spatial resolution of ultrasound imaging. It relies on the thermoelastic effect for generating acoustic pressure waves under specific thermal and stress confinement conditions. When the excitation laser is replaced by a microwave illumination source, the technique is named thermoacoustic tomography (TAT). The photoacoustic (PA) signals recorded in PAT experience only a one-way transmission through the skull. Accordingly, they are generally less attenuated and aberrated than the echo data recorded in transcranial ultrasound imaging, which are distorted by the effects of a two-way transmission through the skull. In addition, PAT based on endogenous hemoglobin contrast is particularly suitable for imaging the blood vessels of the cerebral cortex. Multi-wavelength PAT may be used to compute oxygen saturation of hemoglobin and to monitor functional activities of the human cerebral cortex. Moreover, much of the broadband PA signal energy resides at frequencies less than 1 MHz, and these relatively low-frequencies interact less strongly with skull bone than do higher frequency ultrasound beams that are typically employed in pure ultrasound imaging.

Flat pressure transducers, which are used typically for pressure measurements associated with macroscopic regions of interest, generally function over a relatively small field-of-view (FOV) with acceptable sensitivity; thus PAT and TAT of the cerebral cortex in large animals using existing methods may be limited in one aspect by existing instrumentation. The transducer's sensitivity is typically traded off against the transducer's detecting angle, which influences the instrument's field of view; large-aperture detectors may achieve better sensitivity at the expense of FOV, whereas small point detectors may measure over a larger FOV while compromising the detection sensitivity. Negative lens transducers offer enhanced FOV characteristics, but introduce attenuation and reverberation of ultrasonic waves, which decrease the instrument's sensitivity and degrade reconstruction accuracy; negative-lens transducers are typically not considered suitable for robust animal imaging.

A major technical challenge in PAT/TAT brain imaging is reduction of image distortion associated with the surrounding skull. Transcranial PAT studies have revealed structure and hemodynamic responses in small animals and anatomical structure in human infant brains. Because the skulls in those studies were relatively thin (about 1 mm), they did not significantly aberrate the PA signals and conventional back-projection methods were employed for image reconstruction. However, PA signals may be significantly aberrated by thicker skulls. To render PAT an effective modality for use with transcranial imaging in large primates, including humans, it is necessary to develop image reconstruction methodologies that may accurately compensate for skull-induced aberrations of the recorded PA signals.

A previous image reconstruction method sought to compensate for PA signal aberration associated with acoustic wave reflection and refraction within the skull. In this method, the skull was assumed to be acoustically homogeneous. Accordingly, the method did not explicitly account for scattering effects that arose from heterogeneities in the skull. As a result of the simplified skull model employed, only modest improvements in image quality were observed as compared to use of a standard back-projection-based reconstruction method.

Therefore, there remains an important need for the development of improved image reconstruction methodologies for transcranial PAT/TAT that are based upon more accurate models of the skull's heterogeneous acoustic properties and may effectively compensate for skull-induced image distortions.

SUMMARY OF THE INVENTION

The present invention generally relates to methods and systems of in vivo imaging of a brain situated within a skull of a subject.

In one aspect, a method of imaging a brain situated within a skull of a subject is provided. The method includes obtaining an adjunct image dataset corresponding to a region of interest comprising the skull of the subject. analyzing the adjunct image dataset to obtain a spatial model of one or more acoustic properties of the region of interest, obtaining one or more photoacoustic imaging signals corresponding to the brain of the subject through the skull of the subject at a skull spatial position, registering the spatial model with the skull spatial position to establish an imaging model, and reconstructing a photoacoustic image of the subject's brain by implementing an image construction method using the imaging model and the one or more photoacoustic signals.

In this aspect, the adjunct image dataset may be obtained using a device chosen from an X-ray CT scanning device and an MRI device. The adjunct image dataset may include a spatial map of porosity and the one or more acoustic properties comprise a speed of sound and an ambient density. The image reconstruction method may be chosen from a time-reversal reconstruction method and an iterative reconstruction method.

In this aspect, the time-reversal reconstruction method may include solving discretized forms of acoustic equations describing the propagation of an acoustic wavefield though a heterogeneous medium subject to one or more initial conditions corresponding to an initial photoacoustically generated wavefield within the medium and an initial acoustic particle velocity of zero throughout the medium to obtain the photoacoustic image corresponding to a spatial distribution of an initial acoustic wavefield; the initial acoustic wavefield may be proportional to an absorbed optical energy density. The discretized forms of the acoustic equations may solved using a numerical algorithm chosen from a real-space finite-element method, a real-space finite-difference method, and a k-space pseudospectral method.

Also in this aspect, the iterative reconstruction method may include iteratively solving a discretized imaging model that includes a system matrix to obtain the photoacoustic image corresponding to a spatial distribution of an initial acoustic wavefield; the initial acoustic wavefield may be proportional to an absorbed optical energy density. The iterative reconstruction method may solve the discretized imaging model using an optimization relation. The optimization relation may be a total variation-regularized penalized least-squares cost function.

Additionally in this aspect, the method may further include generating a second photoacoustic image and subjecting the photoacoustic image and the second photoacoustic image to a differential imaging method that includes subtracting the second photoacoustic image from the photoacoustic image to obtain a differential image. The differential image may subjected to a high-pass filter. The photoacoustic image may correspond to the brain and the skull of the subject at a first condition and the second photoacoustic image may correspond to the brain and the skull of the subject at a second condition. The first condition may include an untreated baseline condition and the second condition may include a condition after a treatment. The treatment may be chosen from: a change in an endogenous contrast agent, an introduction of an exogenous contrast agent, a therapeutic treatment, and a performance of a cognitive task.

In another aspect, a photon recycling device is provided that includes a solid cylindrical body with a first end and a second end; a concave curved surface at the second end having a vertex within the cylindrical body; an opening at about the center of the first end of the cylindrical body connecting first end and the vertex of the parabolic surface; and at least one concave lens located within the opening. The at least one concave lens may include a plano-concave lens and a bi-concave lens. The curved surface may be an elliptic paraboloid.

BRIEF DESCRIPTION OF THE DRAWINGS

The following figures illustrate various aspects of the disclosure.

FIG. 6A is an image of the exposed reference object reconstructed using a back-projection method. FIG. 6B is an image of the reference object situated within a skull that was reconstructed using a back-projection method. FIG. 6C is an image of the reference object situated within a skull that was reconstructed using a time-reversal method.

FIG. 10A is a PAT image of the $sO_2$ variation within the two tubes within region marked in FIG. 10C obtained without skull covering. FIG. 10B is a PAT image of the $sO_2$ variation within the two tubes within the region marked in FIG. 10C obtained with skull covering.

FIGS. 27A and 27E are PAT images of a human skull obtained with and without a photon recycling device, respectively. FIGS. 27B and 27F are PAT images of a triangular graphite target obtained through the top area of a whole adult human skull with and without a photon recycling device, respectively. Each image shown in FIGS. 27A-27B and FIGS. 27E-27F were acquired five times to calculate the signal-to-noise ratio (SNR), and the average of the five images are shown in each respective figure. FIG. 27C is a differential image obtained from FIG. 27A and FIG. 27B. FIG. 27G is a differential image obtained from FIG. 27E and FIG. 27F. FIGS. 27D and 27G are standard deviation maps derived from the five differential images that were averaged to obtain FIG. 27C and FIG. 27G, respectively.

Corresponding reference characters and labels indicate corresponding elements among the views of the drawings. The headings used in the figures should not be interpreted to limit the scope of the claims.

DETAILED DESCRIPTION

Provided herein is a system and method for transcranial image reconstruction for PAT/TAT brain imaging that may effectively compensate for skull-induced image distortions. By use of information regarding the skull morphology and composition obtained from adjunct imaging data, a subject-specific imaging methodology may account for skull-induced aberrations, blurring, or distortions in the reconstructed PA image. Acoustic information including, but not limited to speed of sound (SOS) and density maps, may be derived from the adjunct imaging data. The image reconstruction method may compensate for skull-induced acoustic aberrations and may further enhance image fidelity in transcranial PAT and TAT brain imaging.

To be consistent with the commonly used terminology, whenever possible, the terms used herein will follow the definitions recommended by the Optical Society of America (OCIS codes).

The term "photoacoustic tomography" or "thermoacoustic tomography" refers to a photoacoustic imaging technology that detects acoustic or pressure waves generated by light absorption in the volume of a material (such as biological tissue). However, the emphasis in this method is on computer-based image reconstruction.

I. Method of Transcranial PAT/TAT Image Reconstruction

Figure 1:
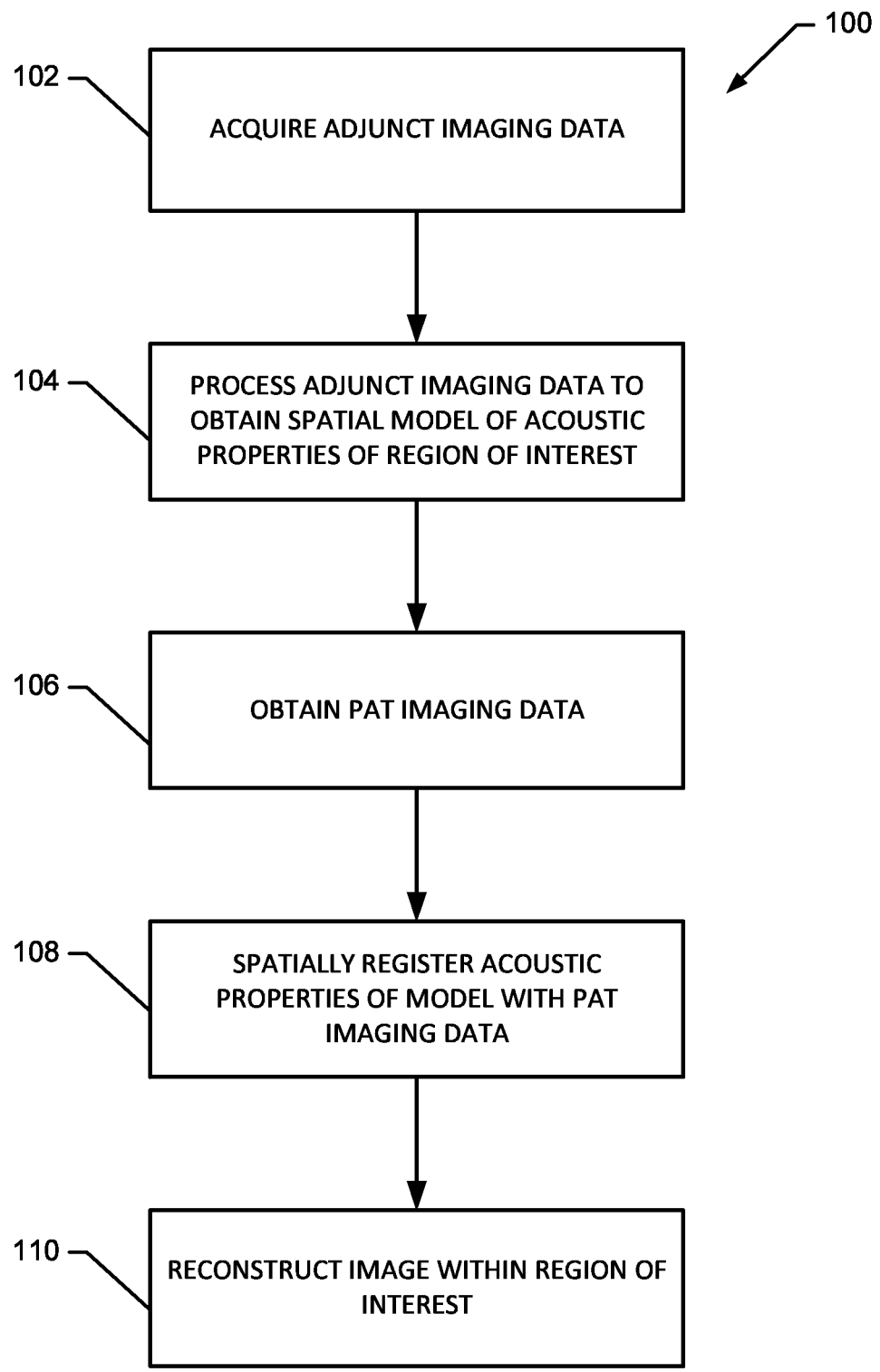
FIG. 1 is a block diagram of a method of obtaining a reconstructed photoacoustic image using adjunct imaging data.
Figure 2:
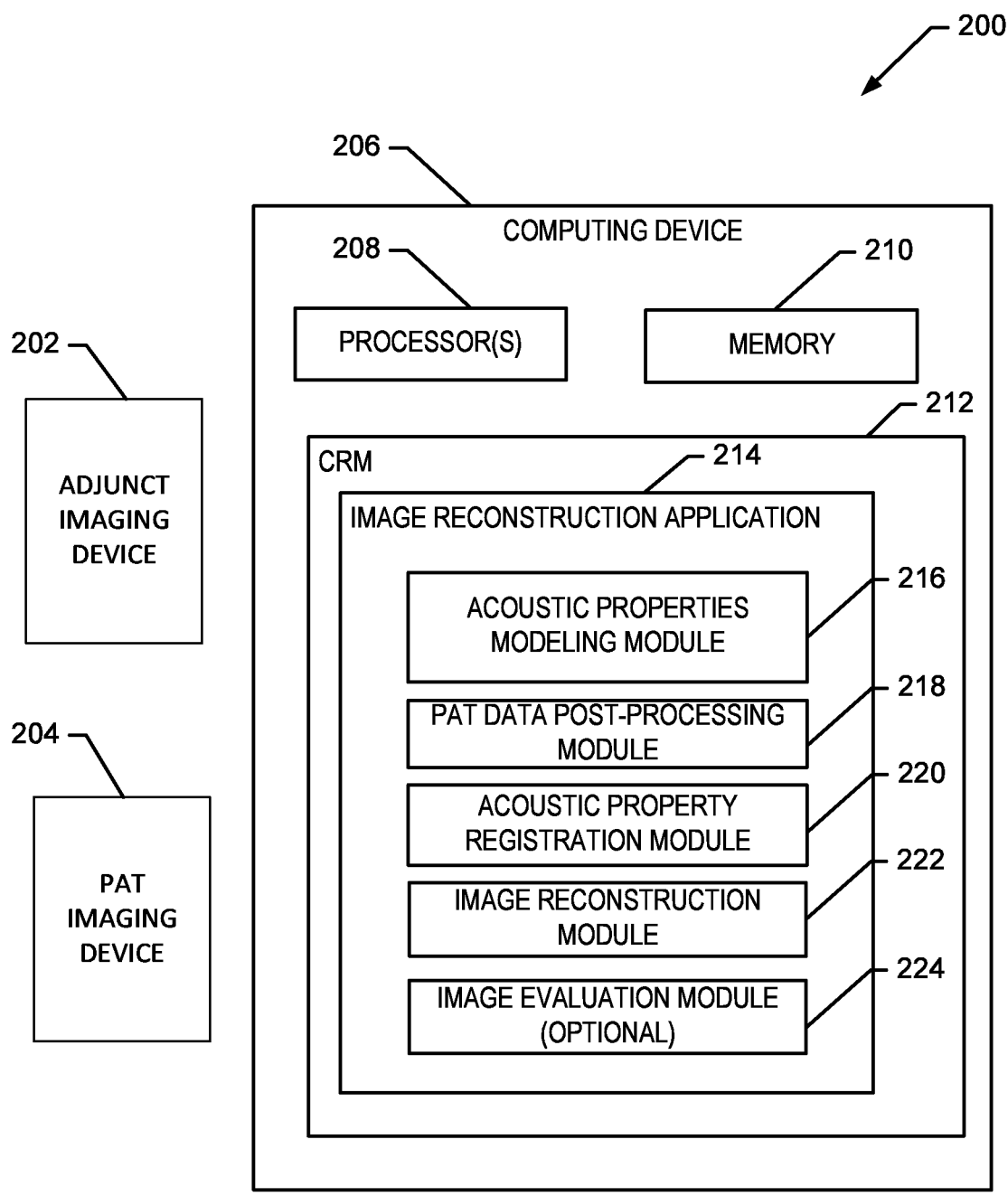
FIG. 2 is a schematic of a photoacoustic system using adjunct imaging data.

In an aspect, the method of transcranial PAT/TAT image reconstruction may include incorporating detailed subject-specific descriptions of the acoustic properties of the skull to mitigate skull-induced blurring and distortions in the reconstructed image. A block diagram illustrating a method 100 in one aspect is provided in FIG. 1. The method 100 includes acquiring an adjunct imaging dataset at step 102, processing the adjunct imaging dataset to define the parameters of a spatial model of one or more acoustic properties of the skull of the subject at step 104, obtaining PAT/TAT imaging data at step 106 at a skull location, spatially registering the one or more acoustic properties of the spatial model with the skull location of the PAT/TAT imaging data at step 108, and reconstructing a photoacoustic image within the region of interest at step 110.

The method of transcranial PAT/TAT image reconstruction 100 may be used to obtain artifact-free structural PA imaging of the brain through the skin and skull of a subject. In an aspect, the method may further include obtaining functional PA imaging of a subject's brain using exogenous and/or endogenous contrast agents.

A. Adjunct Data Acquisition and Processing

Referring again to FIG. 1, the method 100 may include acquiring an adjunct imaging dataset comprising adjunct imaging data at step 102 and processing the acquired adjunct imaging dataset to define the parameters of a spatial model of acoustic properties of the skull at step 104. In an aspect, the adjunct imaging dataset may be acquired from various imaging modalities including, but not limited to X-ray CT, MRI, ultrasound, and any other imaging method known in the art. In one aspect, the adjunct imaging dataset may be acquired by X-ray CT imaging methods. In another aspect, the adjunct imaging dataset may be obtained using fast echo MRI methods. In an additional aspect, the adjunct imaging dataset may be obtained using pulse ultrasound methods. In this additional aspect, the pulse ultrasound data may provide data for the outer boundary of the skull.

Assuming that the skull size and shape does not change, the spatial model of the acoustic properties of the skull, once obtained, may be reused for repeated and/or subsequent PAT imaging studies of that patient in one aspect. In another aspect, the speed-of-sound (SOS) and density maps derived from the adjunct data may be reused similarly. In these aspects, eliminating the need for the acquisition and processing of multiple adjunct datasets provide the capability to safely monitor brain injuries or to conduct other longitudinal studies. The repeated use of reference adjunct data reduces the time and cost expended obtaining multiple adjunct imaging datasets and reduces the exposure to associated hazards such as ionizing radiation used in X-ray CT imaging methods.

The spatial resolution of the adjunct imaging dataset may range between about 0.1 mm and about 0.75 mm. In one aspect, the degree of spatial resolution of the adjunct data may be selected based on the wavelength of the acoustic signals obtained during PA/PT imaging. In one aspect, the spatial resolution of the adjunct imaging may be selected to be of smaller dimension than the wavelength of the acoustic signal propagating through the tissues of the patient. The acoustic wavelength may depend on any one or more of at least several factors including, but not limited to the type of tissue and the type of acoustic wave. Non-limiting examples of types of tissue include: brain tissues such as gray matter, white matter, and blood vessels; skin; and bone. Non-limiting examples of types of acoustic waves include longitudinal acoustic waves and shear acoustic waves. In one aspect, the resolution of the adjunct data may be selected to be of smaller dimension than the smallest acoustic wavelength for any and all combinations of tissue type and type of acoustic wave. The resolution of the adjunct imaging dataset may affect the accuracy of the acoustic properties determined from the adjunct data.

The adjunct imaging dataset may be processed to specify the parameters of an imaging model comprising a spatial model of acoustic properties of a region of interest. The spatially-varying speed of sound (SOS) and mass density distributions of the subject's skull to be imaged may be determined using the adjunct imaging data. In an aspect, a porosity map distribution of the subject's skull may be obtained using methods known in the art including, but not limited to adjunct X-ray CT image data and fast echo MRI data to infer the spatially-variant SOS and density distributions of the skull. A method of acquiring acoustic properties from other additional imaging modalities may be developed from previous methods in the art to facilitate transcranial adaptive acoustic focusing for minimally invasive brain surgery.

In one aspect, adjunct X-ray CT data may be processed to determine the spatially-varying SOS and mass density maps of the skull. The SOS and density maps of the skull may be estimated from a porosity map obtained from the adjunct X-ray CT data using mixture laws in a biphasic medium (bonewater). In one aspect, $H_k$ denotes the value of the $k^{th}$ voxel in the X-ray CT image, which is measured in Hounsfield Units. In this aspect, a voxel-based representation of the porosity map, denoted as $\phi_k$, may be determined from each $H_k$ at each location in the porosity map using Eqn. (I):

$$\Phi_k = 1 - \frac{H_k}{H^{Max}} \qquad \text{Eqn. (I)}$$

where $H^{Max}$ is the maximum value of $H_k$ in the CT image.

In an aspect, $\rho_k$ and $c_k$ may denote voxel-based representations of the skull's mass density and SOS distributions. In this aspect, the density map $\rho_k$ may be estimated from the porosity map using Eqn. (II):

$$\rho_k = \phi_k \rho^w + (1-\phi_k)\rho^s, \qquad \text{Eqn. (II)}$$

where $\rho^w = 1000$ kgm$^3$ is the density of water, and $\rho^s = 2100$ kg/m$^3$ is the density of skull as determined by ultrasound experiments. Without being limited to any particular theory, the elastic modulus of bone is proportional to the apparent density cubed as a first order approximation. In an aspect, the SOS map, $c_k$, may be determined from the porosity map using Eqn. (III):

$$c_k = \phi_k c^w + (1-\phi_k)c^s, \qquad \text{Eqn. (III)}$$

Where $c^w = 1480$ ms is the SOS in water, and $c^s = 2900$ ms is the speed of sound of skull bone as determined by previous ultrasound experiments.

In an aspect, the subject-specific SOS and mass density distributions may then be spatially registered or aligned with the PA imaging data and an image reconstruction method may be used to estimate the spatially-varying initial amplitude of the thermoacoustically-induced pressure signals within the brain of the subject.

B. Obtaining PAT/TAT Imaging Data

Referring again to FIG. 1, the method 100 may further include obtaining PAT and/or TAT imaging data from the subject using any known methods at step 106. As discussed previously herein, acquiring the PAT/TAT imaging data may include illuminating a region of interest with a coherent light/microwave source and detecting the acoustic signal generated from the region of interest in response to this illumination. In various aspects, the PAT/TAT imaging data may be obtained using a PAT/TAT imaging system, described in additional detail herein below.

In one aspect, a PAT imaging system may include a laser and one or more optics elements including, but not limited to, a concave lens to expand the laser pulse and thereby increase the area of illumination over a larger region of interest and/or to reduce regional variation in laser fluence within a cross-sectional area of the laser pulse. In another aspect, the PAT imaging system may further include a signal enhancer including, but not limited to a photon recycler as further described herein below to enhance the degree of illumination within the area of interest without further increasing the laser fluence of the laser pulses produced by the laser.

C. Reconstructing Image

Referring again to FIG. 1, at step 108 the spatial model of acoustic properties of the skull derived from the adjunct imaging dataset at step 104 may be spatially registered with the skull location used to obtain the PAT imaging data to establish an imaging model. The imaging model, which incorporates the spatial model and the PAT imaging data comprising at least one photoacoustic signal obtained in step 102 may be used with an image reconstruction method to reconstruct a photoacoustic image at step 110. In an aspect, the spatial model of the acoustic properties of the skull may be spatially registered with the PAT imaging data to inform image reconstruction of the PAT/TAT imaging data including, but not limited to, mitigating skull-induced aberrations of the measured PA signals.

Figure 3:
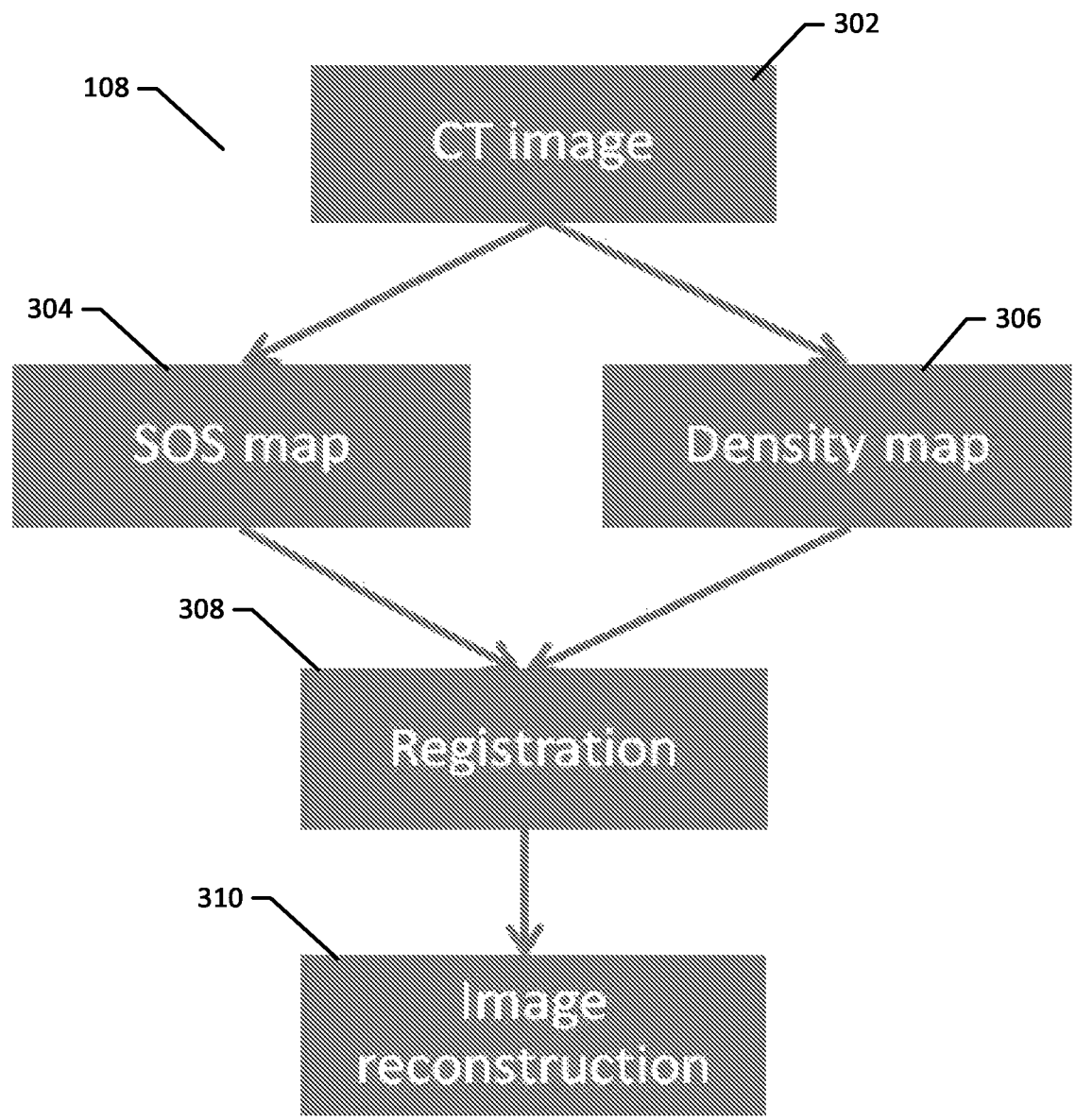
FIG. 3 is a block diagram illustrating the general workflow of the reconstruction methodology in one aspect.

A workflow diagram of step 108 of the method 100 in one aspect is depicted in FIG. 3. In this aspect, the estimated SOS map ($c_k$) 304 and mass density map ($\rho_k$) 306, derived from the adjunct CT image 302, may be spatially registered to the frame of reference of the TAT/PAT imaging data at step 308 so that the acoustic characteristics from the maps may be used within an image reconstruction method for estimation of the spatial distribution of an initial acoustic wavefield within the region of interest of the brain at step 310. Without being limited to any particular theory, the spatial distribution of the initial acoustic wavefield is known to be proportional to the absorbed optical energy density. In an aspect, the frame of reference of the TAT/PAT imaging data may be the skull spatial position during PA imaging.

Referring again to FIG. 1, an image may be reconstructed using an image reconstruction method at step 110. In various aspects, the method of transcranial PAT imaging 100 may include any one of at least several image reconstruction methods, described herein below.

In one aspect, the image reconstruction method may be a time-reversal image reconstruction method. In another aspect, the image reconstruction method may be an iterative reconstruction method. The image reconstruction method in these aspects may produce images with improved fidelity and reduced artifact levels as compared to existing reconstruction method such as back-projection methods.

In an aspect, the image reconstruction method may compensate for refraction and diffraction of the photoacoustic wavefields caused by heterogeneities in the SOS and density distributions of the skull. In this aspect, other confounding effects thought to be secondary may not be incorporated into the image reconstruction method. Non-limiting examples of secondary confounding effects include the effects of acoustic shear waves propagating in the skull and the attenuation of the photoacoustic wave field in the skull. Without being limited to any particular theory, the density and SOS heterogeneities are thought to both have stronger effects and cause more acoustic energy to be reflected back into the skull than do the shear wave mode-conversion or attenuation for acoustic plane-wave components incident on the skull surface at small (about 30 degrees or less) angles from the surface normal.

In another aspect, the image reconstruction method may include the effects of acoustic attenuation and shear wave mode-conversion as well as the effect of density and SOS heterogeneities. Without being limited to a particular theory, these secondary effects may be observed in certain high-spatial resolution components of the imaged object. In an aspect, the effects of shear wave propagation and attenuation both may be strongly dependent on the thickness of the skull. In some aspects, the distortions to the PA signal due to absorption and propagating shear waves may of second-order effect as compared to the distortions due to the variations in the SOS and density.

In various aspects, the image reconstruction methods may be derived from the equations governing the generation and propagation of photoacoustic wavefields; these equations may be provided in a continuous form or in a discretized form as described herein below. The PA signal data and imaging model derived from the adjunct imaging data may be combined and used along with the equations governing the generation and propagation of photoacoustic wavefields in order to obtain a spatial map of $p_0$, the pressure induced within the tissue as a result of laser illumination, based on the acoustic signals measured by the transducers of the PA imaging system.

i. Continuous Formulation of Photoacoustic Wavefield Propagation

In various aspects, the reconstruction methods make use of the equations describing the generation and propagation of a photoacoustic wavefield within an acoustically heterogeneous medium. The continuous form of the photoacoustic wavefield equations are provided herein below.

To obtain PAT imaging data, tissue within the region of interest may be irradiated by a laser pulse at time t=0. In response to the laser pulse, the tissue may generate an induced pressure wavefield p. The function p(r,t) denotes the thermoacoustically-induced pressure wavefield at time t≥0 at a location r.

In various aspects, acoustic absorption may not be negligible. For a wide variety of materials characterized by relatively strong attenuation of acoustic signals including, but not limited to, biological tissues, the acoustic attenuation coefficient may be described by a frequency power law expressed as Eqn. (IV):

$$\alpha(r,f) = \alpha_0(r) f^y \quad \text{Eqn. (IV)}$$

where f is the temporal frequency in MHz, $\alpha_0$ is the frequency-independent attenuation coefficient in dB MHz$^{-y}$ cm$^{-1}$, and y is the power law exponent which may range from about 0.9 to about 2.0 in biological tissues.

Without being limited to any particular theory, assuming a heterogeneous fluid medium in which acoustic losses may be characterized by an acoustic power law as in Eqn. (IV), three coupled equations may be used to describe the forward propagation of p(r,t):

$$\frac{\partial}{\partial t}u(r,t) = -\frac{1}{\rho_0(r)}\nabla p(r,t).$$  Eqn. (V)

$$\frac{\partial}{\partial t}\rho(r,t) = -\nabla \rho_0(r)u(r,t).$$  Eqn. (VI)

$$p(r,t) = c_0(r)^2\left\{1 - \mu(r)\frac{\partial}{\partial t}(-\nabla^2)^{y/2-1} - \eta(r)(-\nabla^2)^{\frac{(y-1)}{2}}\right\}\rho(r,t)$$  Eqn. (VII)

subject to the initial conditions:

$$p_0(r) \equiv p(r,t)|_{t=0} = \Gamma(r)A(r), u(r,t)|_{t=0} = 0.$$  Eqn. (VIII)

Here, A(r) denotes the absorbed optical energy density within the object, $\Gamma(r)$ is the dimensionless Grueneisen parameter, u(r, t) is the acoustic particle velocity, $c_0(r)$ denotes the medium's SOS distribution, and $\rho(r, t)$ and $\rho_0(r)$ describe the distributions of the medium's acoustic and ambient densities, respectively. The object function A(r) and all quantities that describe properties of the medium are assumed to be represented by bounded functions possessing compact supports. The quantities $\mu(r)$ and $\eta(r)$ describe the acoustic absorption and dispersion proportionality coefficients that are defined as:

$$\mu(r) = -2\alpha_0 c_0(r)^{y-1},$$  Eqn. (IX)
$$\eta(r) = 2\alpha_0 c_0(r)^y \tan\left(\frac{\pi y}{2}\right)$$

Acoustic absorption and dispersion may be modeled by the second and third terms in the bracket of Eqn. (VII), which employs two lossy derivative operators based on the fractional Laplacian to separately account for the acoustic absorption and dispersion in a way that is consistent with Eqn. (IV). In one aspect, when acoustic attenuation may be neglected, $\mu(r)=0$ and $\eta(r)=0$, and Eqn. (VII) reduces to:

$$p(r,t) = c_0(t)^2 \rho(r,t)$$  Eqn. (X)

ii. Time-Reversal Image Reconstruction Method

In an aspect, the image reconstruction method may be a time-reversal image reconstruction method. Time-reversal image reconstruction refers to an image reconstruction method based on a numerical propagation model with a time-varying boundary condition corresponding to the measured data in reversed temporal order. For image reconstruction based on time-reversal, $\{\hat{p}(r_m, t\in[0, T])\}_{m=1}^M$ denotes the measured pressure wavefield data, where $r_m$ denotes the location of the $m^{th}$ ultrasonic transducer, M indicates the number of measurement locations, and T denotes the maximum time at which the pressure data is recorded. The PAT image reconstruction obtains an estimate of $p_0(r)$ or, equivalently, A(r), from knowledge of $\{\hat{p}(r_m, t\in[0, T])\}_{m=1}^M$, $c_0(r)$, and $\rho_0(r)$. The time-reversal method may be based on a full-wave solution to the acoustic wave equation for heterogeneous media; therefore it may compensate for the aberration in the photoacoustic signals due to the variations in $c_0(r)$ and $\rho_0(r)$ within the skull.

In an aspect, the time-reversal image reconstruction method may be a k-space pseudospectral image reconstruction method. The k-space pseudospectral time-reversal image reconstruction method may be employed to propagate a photoacoustic wavefield forward in space and time. The k-space reconstruction method may approximate Eqns. (V), (VI), and (X), neglecting terms proportional to $\nabla\rho_0$(r, and may solve discretized versions of the three coupled lossless acoustic equations backward in time with initial and boundary conditions specified as:

$$p(r,t)|_{t=T}=0, u(r,t)|_{t=T}=0, p(r_m,t)=\hat{p}(r_m,t).$$  Eqn. (XI)

In this aspect, the k-space pseudospectral time-reversal image reconstruction method is based on a full-wave solution to the acoustic wave equation for heterogeneous media, and may therefore compensate for scattering due to variations in $c_0(r)$ and $\rho_0(r)$ within the skull. Because the fast Fourier transform (FFT) is used to compute the spatial derivatives in the k-space pseudospectral method, its computational efficiency may be an improvement to other existing methods such as finite-difference time-domain methods. The accuracy of the temporal derivatives in this method may also be refined by use of k-space adjustments.

The acoustic equations may be discretized by specifying the locations of the $N=N_1 N_2 N_3$ vertices of a 3-D Cartesian grid, where $N_1$ denotes the number of vertices along the ith dimension as $r_1, \ldots, r_N$, where each r is an (x,y,z) value of a vertex in the 3-D Cartesian grid. In addition, m$\Delta$t may be used to denote discretized values of the temporal coordinate t, where m is a non-negative integer and $\Delta$t is a positive real number. The sampled values of p(r,t=m$\Delta$t) and $u^i$(r, t=m$\Delta$t), i=1, 2 or 3, corresponding to spatial locations on the 3-D Cartesian grid may be described by the 3-D matrices $P_m$ and $U_m^i$, respectively, where the subscript m indicates that these quantities depend on the temporal sample index m. Unless otherwise indicated, the dimensions of all 3-D matrices will be $N_1 \times N_2 \times N_3$. Lexicographically ordered vector representations of these matrices may be denoted as:

$$u_m^i \equiv (u^i(r_1, m\Delta t), \ldots, u^i(r_N, m\Delta t))^T$$  Eqn. (XII)

$$p_m \equiv (p(r_1, m\Delta t), \ldots, p(r_N, m\Delta t))^T$$  Eqn. (XIII)

The values of the ambient density $\rho_0(r)$ and squared SOS distribution $c_0^2(r)$ from the imaging model derived from the adjunct data as described herein above may be represented as:

$$Q \equiv \text{diag}(\rho_0(r_1), \ldots, \rho_0(r_N))$$  Eqn. (XIV)

$$C \equiv \text{diag}(c_0^2(r_1), \ldots, c_0^2(r_N))$$  Eqn. (XV)

where diag($\alpha_1, \ldots, \alpha_N$) is defined as a diagonal 2-D matrix whose diagonal entries starting in the upper left corner are $\alpha_1, \ldots, \alpha_N$.

In another aspect of the k-space pseudospectral method, the 1-D discrete spatial derivatives of the sampled fields with respect to the ith dimension (i=1, 2, or 3) may be computed in the Fourier domain as:

$$\nabla_i^{Mat} P_m = F^{-1}\{jK^i \cdot \kappa \cdot F\{P_m\}\}$$  Eqn. (XVI)

$$\nabla_i^{Mat} U_m^i = F^{-1}\{jK^i \cdot \kappa \cdot F\{U_m^i\}\}$$  Eqn. (XVII)

where $j=\sqrt{-1}$, the superscript "Mat" indicates that the 1-D discrete derivative operator $\nabla_i^{Mat}$ acts on a 3-D matrix, F and $F^{-1}$ denote the 3-D forward and inverse discrete Fourier transforms (DFTs), and o in Eqns. (XVI) and (XVII) denotes the Hadamard product operator. The elements of the 3-D matrix $K^i$ (i=1, 2, 3) may be written in the form:

$$K^1_{n_1 n_2 n_3} = 2\pi \frac{n_1 - 1}{L_1} \qquad \text{Eqn. (XVIII)}$$

$$K^2_{n_1 n_2 n_3} = 2\pi \frac{n_2 - 1}{L_2} \qquad \text{Eqn. (XIX)}$$

$$K^3_{n_1 n_2 n_3} = 2\pi \frac{n_3 - 1}{L_3} \qquad \text{Eqn. (XX)}$$

where $n_i = 1, \ldots, N_i$ ($i = 1, 2, 3$), and $L_i$ denotes the length of the spatial grid in the ith dimension.

The $\kappa$ term in Eqns. (XVI) and (XVII) denotes a k-space operator given by:

$$\kappa = \sin c((\tfrac{1}{2}) \Delta t c_{min} K) \qquad \text{Eqn. (XXI)}$$

where $\sin c(x) = (\sin(x)/x)$, $c_{min}$ is the minimum value for all of $c_0(r)$, and $K$ is a 3-D matrix defined as:

$$K \equiv \sqrt{\sum_{i=1}^{3} K^i \circ K^i} \qquad \text{Eqn. (XXII)}$$

and the sin c function and square root functions in both of Eqns. (XXI) and (XXII) are element-wise operations.

The operators $\Phi_i^{Mat}$ and $\Psi_i^{Mat}$ may be defined as:

$$\Phi_i^{Mat} P_m \equiv -\Delta t Q^{-1} \nabla_i^{Mat} P_m \qquad \text{Eqn. (XXIII)}$$

$$\Psi_i^{Mat} U_m \equiv -\Delta t Q \nabla_i^{Mat} U_m^i \qquad \text{Eqn. (XXIV)}$$

In an aspect, $\Phi_i$ and $\Psi_i$ may be defined such that $\Phi_i p_m$ and $\Psi_i u_m^i$ are lexicographically ordered vector representations of the matrices $\Phi_i^{Mat} P_m$ and $\Psi_i^{Mat} U_m^i$, respectively. In terms of these quantities, the discretized forms of Eqns. (V), (VI), and (VII) may be expressed as:

$$u_{m+1}^i = u_m^i + \Phi_i p_m \qquad \text{Eqn. (XXV)}$$

$$\rho_{m+1}^i = \rho_m^i + \Psi_i u_{m+1}^i \qquad \text{Eqn. (XXVI)}$$

where $\rho_m^i$ is an N×1 vector whose elements are defined to be zero for m=0, and $$p_{m+1} = C \sum_{i=1}^{3} \{\rho_{m+1}^i + A u_{m+1}^i + B \rho_{m+1}^i\} \qquad \text{Eqn. (XXVIII)}$$

The quantities $Au_{m+1}^i$ and $B\rho_{m+1}^i$ in Eqn. (XXVII) represent the absorption and dispersion terms in Eqn. (VII), and may be defined as lexicographically ordered vector representations of $A^{Mat} U_{m+1}^i$ and $B^{Mat} N_{m+1}^i$, which are defined in analogy to Eqn. (VII) as:

$$A^{Mat} U_{m+1}^i \equiv \mu F^{-1} \left\{ K^{y-2} F \left\{ Q \sum_{i=1}^{3} \nabla_i^{Mat} U_{m+1}^i \right\} \right\} \qquad \text{Eqn. (XXVII)}$$

$$B^{Mat} N_{m+1}^i \equiv \eta F^{-1} \left\{ K^{y-1} F \left\{ \sum_{i=1}^{3} N_{m+1}^i \right\} \right\} \qquad \text{Eqn. (XXIX)}$$

where $N_{m+1}^i$ is the 3-D matrix form of $\rho_m^i$, and $\mu$ and $\eta$ are defined as:

$$\mu = \text{diag}(\mu_0(r_1), \ldots, \mu_0(r_N)) \qquad \text{Eqn. (XXX)}$$

$$\eta = \text{diag}(\eta_0(r_1), \ldots, \eta_0(r_N)) \qquad \text{Eqn. (XXXI)}$$

and $K^{y-2}$ and $K^{y-1}$ are powers of K that may be computed on an element-wise basis.

In an aspect, a time-reversal reconstruction method may include solving the discretized acoustic Eqns. (XXV) (XXVII) subject to initial and boundary conditions similar to those described herein above.

iii. Iterative Image Reconstruction Method

In various aspects, an iterative image reconstruction method based on the exact PA wave equations may be used to reconstruct a PAT image from PA imaging data and an imaging model derived from adjunct imaging data. Starting with the discretized acoustic equations described herein previously, a discretized PA imaging model may be formulated. The initial pressure distribution $p_0$ may be estimated from knowledge of the measured data $\hat{p}$ by iteratively solving the equation derived from this discretized imaging model with an appropriate regularization.

The discretized imaging model may be based on the k-space pseudospectral time-reversal method and may further provide a procedure of implementing the forward and back projection operators associated with the discretized imaging model. In one aspect, the matched forwardback projection operator pair may be employed in an iterative image reconstruction method to minimize a TV-regularized PLS cost function.

In an aspect, the discretized imaging model may neglect transducer characteristics such as the acousto-electrical impulse response (EIR) of the ultrasonic transducers; in this aspect, each transducer may be assumed to be point-like in response. A description of how transducer response characteristics may be incorporated into a developed discretized imaging model is provided in Example 19.

With these assumptions, the measured pressure wavefield data at time $t = m\Delta t$ may be defined as:

$$\hat{p}_m \equiv (p(r_1^d, m\Delta t), \ldots, p(r_L^d, m\Delta t))^T \qquad \text{Eqn. (XXXII)}$$

Where $m = (0, \ldots, M-1)$, M is the total number of time steps and $r_l^d \in \mathbb{R}^3$ ($l = 1, \ldots, L$) denotes the positions of the L ultrasonic transducers that reside outside the support of the object. An estimate of $\rho_0(r)$ or, equivalently, $A(r)$, may be obtained from knowledge of $\hat{p}_m$, $m = 0, \ldots, M-1$, $c_0(r)$, $\rho_0(r)$, $\alpha_0(r)$, and $y$. The acoustic parameters of the medium may be estimated by use of adjunct X-ray CT, ultrasound tomography, or MRI image data and may be assumed to be known in an aspect.

The discretized form of the imaging model for PAT may be expressed generally as:

$$\hat{p} = H p_0 \qquad \text{Eqn. (XXXIII)}$$

where the LM×1 vector $$\hat{p} = \begin{bmatrix} \hat{p}_0 \\ \hat{p}_1 \\ \vdots \\ \hat{p}_{M-1} \end{bmatrix} \qquad \text{Eqn. (XXXIV)}$$

represents the measured pressure data corresponding to all transducer locations and temporal samples, and the N×1 vector $p_0$ is the discrete representation of the sought after initial pressure distribution within the object (i.e., Eqn. (XIII) with m=0). The LM×N matrix H represents the discrete imaging operator, also referred to as the system matrix.

In an aspect, the image reconstruction task is to determine an estimate of $p_0$ from knowledge of the measured data $\hat{p}$.

This may be accomplished by computing an appropriately regularized inversion of Eqn. (XXXIII). In one aspect, the iterative reconstruction method may be implemented by minimizing a penalized least squares cost function; in this one aspect, the action of the operators H and its adjoint $H^\dagger$ may be computed.

The k-space pseudospectral method for numerically solving the photoacoustic wave equation may be used to implement the action of the system matrix H. An explicit matrix representation of H may be employed to determine $H^\dagger$.

Eqns. (XXV)-(XXVII) may be described by a single matrix equation to determine the updated wavefield variables after a time step $\Delta t$ as:

$$v_{m+1} = W v_m \qquad \text{Eqn. (XXXV)}$$

where $v_m = (u_m^1, u_m^2, u_m^3, \rho_m^1, \rho_m^2, \rho_m^3, p_m)^T$ is a $7N \times 1$ vector containing all the wavefield variables at the time step $m\Delta t$. The propagator matrix W is defined as:

$$W \equiv \begin{bmatrix} I_{N\times N} & 0_{N\times N} & 0_{N\times N} & 0_{N\times N} & 0_{N\times N} & 0_{N\times N} & \Phi_1 \\ 0_{N\times N} & I_{N\times N} & 0_{N\times N} & 0_{N\times N} & 0_{N\times N} & 0_{N\times N} & \Phi_2 \\ 0_{N\times N} & 0_{N\times N} & I_{N\times N} & 0_{N\times N} & 0_{N\times N} & 0_{N\times N} & \Phi_3 \\ \Psi_1 & 0_{N\times N} & 0_{N\times N} & I_{N\times N} & 0_{N\times N} & 0_{N\times N} & \Psi_1\Phi_1 \\ 0_{N\times N} & \Psi_2 & 0_{N\times N} & 0_{N\times N} & I_{N\times N} & 0_{N\times N} & \Psi_2\Phi_2 \\ 0_{N\times N} & 0_{N\times N} & \Psi_3 & 0_{N\times N} & 0_{N\times N} & I_{N\times N} & \Psi_3\Phi_3 \\ D_1 & D_2 & D_3 & E & E & E & G \end{bmatrix} \quad \text{Eqn. (XXXVI)}$$

where $D_i \equiv C(A + \Psi_i + B\Psi_i)$ (i=1, 2, 3), $E \equiv C + CB$, $G \equiv C\sum_{i=1}^{3} A\Phi_i + (I+B)\Psi_i\Phi_i$, $I_{N\times N}$ is the N×N identity matrix, and $0_{N\times N}$ is the N×N zero matrix.

The wavefield quantities may be propagated forward in time from t=0 to t=(M-1)Δt as $$\begin{bmatrix} v_0 \\ v_1 \\ \vdots \\ v_{M-1} \end{bmatrix} = T_{M-1} \cdots T_1 \begin{bmatrix} v_0 \\ 0_{7N\times 1} \\ \vdots \\ 0_{7N\times 1} \end{bmatrix} \qquad \text{Eqn. (XXXVII)}$$

where the 7NM×7NM matrices $T_m$ (m=1, . . . , M-1) are defined in terms of W as:

$$T_m \equiv \qquad \text{Eqn. (XXXVIII)}$$

$$\begin{bmatrix} 1_{7N\times 7N} & \cdots & 0_{7N\times 7N} & & \\ \vdots & \ddots & \vdots & 0_{(m+1)7N\times(M-m)7N} & \\ 0_{7N\times 7N} & \cdots & I_{7N\times N} & & \\ 0_{7N\times 7N} & \cdots & W & & \\ 0_{(M-m-1)7N\times m\cdot 7N} & & & 0_{(M-m-1)7N\times(M-m)\cdot 7N} \end{bmatrix}$$

with W residing between the (7N(m−1)+1)th to 7Nmth rows and the (7 Nm+1)th to 7N(m+1)th columns of $T_m$.

From the equation of state in Eqn. (X) and initial conditions (VIII), the vector may be computed from the initial pressure distribution as:

$$\begin{bmatrix} v_0 \\ 0_{7N\times 1} \\ \vdots \\ 0_{7N\times 1} \end{bmatrix} = T_0 p_0 \qquad \text{Eqn. (XXXIX)}$$

where $$T_0 \equiv (\tau, 0_{7N\times N_1}, \ldots, 0_{7N\times N})^T \qquad \text{Eqn. (XL)}$$

$$r \equiv \qquad \text{Eqn. (XLI)}$$

$$\left(0_{N\times N}, 0_{N\times N}, 0_{N\times N}, \frac{1}{3}C^{-1}, \frac{1}{3}C^{-1}, \frac{1}{3}C^{-1}, I_{N\times N}\right)^T$$

And $p_0$ is the initial pressure distribution as defined by Eqn. (XIII) with m=0.

In general, the transducer locations $r_l^d$ at which the PA data $\hat{p}$ are recorded may not coincide with the vertices of the Cartesian grid at which the values of the propagated field quantities are computed. The measured PA data may be related to the computed field quantities via an interpolation operation as:

$$\hat{p} = S \begin{bmatrix} v_0 \\ v_1 \\ \vdots \\ v_{M-1} \end{bmatrix} \qquad \text{Eqn. (XLII)}$$

where $$S \equiv \begin{bmatrix} \Theta & 0_{L\times 7N} & \cdots & 0_{L\times 7N} \\ 0_{L\times 7N} & \Theta & \cdots & 0_{L\times 7N} \\ \vdots & \vdots & \ddots & \vdots \\ 0_{L\times 7N} & 0_{L\times 7N} & \cdots & \Theta \end{bmatrix} \qquad \text{Eqn. (XLIII)}$$

Here, $\theta \equiv [s_1, \ldots, s_L]^T$, where $s_l$ (l=1, . . . , L) is a 1×7N row vector in which all elements are zeros except the four corresponding to acoustic pressure at four grid nodes $r_{l,1}$, $r_{l,2}$, $r_{l,3}$, $r_{l,4}$ that are nearest to the transducer location $r_l^d$. In other words, these four entries are interpolation coefficients to compute the acoustic pressure at the lth transducer, and their values are given by the barycentric coordinates of $r_l^d$ with respect to $r_{l,1}$, $r_{l,2}$, $r_{l,3}$, $r_{l,4}$, which may be determined by Delaunay triangulation.

By use of Eqns. (XXXVII), (XXXIX), and (XXLII), one may obtain $$\hat{p} = S T_{M-1} \cdots T_1 T_0 p_0 \qquad \text{Eqn. (XLIV)}$$

Upon comparison of this result to Eqn. (XXXIII), the sought-after explicit form of the system matrix is identified as:

$$H \equiv S T_{M-1} \cdots T_1 T_0 \qquad \text{Eqn. (XLV)}$$

In an aspect, the iterative image reconstruction method may involve use of a backprojection matrix $H^\dagger$ that corresponds to the adjoint of the system matrix H. Since H contains real-valued elements in this aspect, the adjoint matrix $H^\dagger$ is equivalent to the transpose matrix $H^T$. According to Eqn. (XLV), the explicit form of $H^T$ is given by:

$$H^T = T_0^T T_1^T \cdots T_{M-1}^T S^T \qquad \text{Eqn. (XLVI)}$$

In an aspect, the iterative image reconstruction method may be implemented by seeking solutions of an optimization problem to determine $p_o$. In one aspect, the optimization problem may be provided in the form of a penalized least squares (PLS) cost function containing a total variation (TV) penalty term such as:

$$\hat{p}_0 = \underset{p_0 \geq 0}{\operatorname{argmin}} \|\hat{p} - Hp_0\|^2 + \lambda |p_0|_{TV} \qquad \text{Eqn. (XLVIII)}$$

where λ is the regularization parameter, and a non-negativity constraint was further imposed. For the 3D case, the TV-norm may be defined as:

$$|p_0|_{TV} = \sum_{n=1}^{N} \sqrt{([p_0]_n - [p_0]_{n_1-})^2 + ([p_0]_n - [p_0]_{n_2-})^2 + ([p_0]_n - [p_0]_{n_3-})^2} \qquad \text{Eqn. (XLIX)}$$

where $[p_0]_n$ denotes the n-th grid node, $[p_0]_{n_1}$, $[p_0]_{n_2}$, $[p_0]_{n_3}$ are neighboring nodes before the n-th node along the first, second and third dimension, respectively. In an aspect, a fast iterative shrinkage/thresholding algorithm (FISTA) may be employed to solve Eqn. (XLVIII).

When iterative methods, including FISTA, are employed to minimize a PLS cost function, the action of the operators H and its adjoint $H^\dagger$ are computed. The action of H may be computed by use of any suitable computational tool or software known in the art including, but not limited to the MATLAB k-Wave toolbox. In an aspect, $H^\dagger$ may be computed as:

$$v^{M-1} = \Theta^T \hat{p}_{M-1} \qquad \text{Eqn. (L)}$$

$$v^{m-1} = \Theta^T \hat{p}_{m-1} + W^T v^m, m=M-1, \ldots, 1 \qquad \text{Eqn. (LI)}$$

$$p^{bp} = \tau^T v^0 \qquad \text{Eqn. (LII)}$$

D. Differential Imaging Methods

The targets in the PAT brain images obtained using the PAT imaging system as described herein may be distorted and/or dislocated due to the discontinuous acoustic properties between brain tissue and the surrounding skull. In an aspect, the method of image reconstruction may include improving the image quality of the reconstructed PA image using differential imaging methods. As used herein, differential imaging methods refer to the subtraction of two PAT images to improve the quality of one or both of the subtracted images, or to obtain additional information not readily available in one or both images.

In another aspect, differential imaging methods may be used to analyze changes between pairs of images. In one aspect, differential imaging methods may be used to compare images obtained at different times; for example structural changes in the brain in response to a treatment may be monitored using differential imaging methods. In another aspect, differential imaging methods may be used to determine changes in physiological or other aspects of the imaged brain, for example before and after neural stimulation or injection of contrast agents. The differential images may be used to trace or monitor dynamic changes in regions of interest within the brain.

In another additional aspect, the differential data may be subjected to one or more data filters to enhance the contrast and to facilitate the imaging of structures of interest. Non-limiting examples of suitable data filters include low-pass filters, high-pass filters, mid-pass filters, and any other suitable filter known in the art. In one aspect, the differential data may be subjected to a low-pass filter to enhance the contrast and to facilitate the imaging of structures of interest. Without being limited to any particular theory, high frequency signals are known to be more attenuated while passing through skull tissue. In this aspect, subjecting the differential data to a high-pass filter may result in a reconstructed image that includes structural features not identifiable in the unfiltered differential image.

II. System for Transcranial PAT/TAT Image Reconstruction

In various aspects, a system for transcranial PAT/TAT image reconstruction 200 may include, but is not limited to, an adjunct imaging device 202, a PAT imaging device 204, and a computing device 206. The computing device 206 may further include at least one processor 208, a memory 210, and a CRM 212 comprising an image reconstruction application 214.

The image reconstruction application 214 may include, but is not limited to, an acoustic properties modeling module 216, a PAT data post-processing module 218, an acoustic property registration module 220, and an image reconstruction module 222. The image reconstruction application 214 may optionally include an image evaluation module 224 in an aspect.

The PAT system used to acquire the PAT imaging data may include a coherent light source including, but not limited to, a laser having a wavelength in the near infrared range. In one aspect, the laser wavelength may range from about 630 nm to about 1300 nm. In various other aspects, the laser wavelength may range from about 630 nm to about 700 nm, from about 650 nm to about 750 nm, from about 700 nm to about 800 nm, from about 750 nm to about 850 nm, from about 800 nm to about 900 nm, from about 850 nm to about 950 nm, from about 900 nm to about 1000 nm, from about 950 nm to about 1050 nm, from about 1000 nm to about 1200 nm, and from about 1100 nm to about 1300 nm. In yet another aspect, the laser wavelength may be about 730 nm. In an additional aspect, the laser wavelength may be 1064 nm.

In an aspect, the laser may produce laser pulses at a laser pulse rate ranging from about 10 Hz to about 1.2 MHz. In various other aspects, the laser pulse rate may range from about 10 Hz to about 0.5 MHz, from about 250 Hz to about 1 MHz, and from about 0.7 MHz to about 1.2 MHz. Without being limited to any particular theory, the laser pulse rate may influence the data acquisition time of the PAT imaging data. In another aspect, a slower laser pulse rate may be used with the application of a signal enhancer. In an aspect, the signal enhancer may be a photon recycler further described herein below.

In an aspect, the laser of the PA imaging system may produce laser pulses at the pulse width ranging from about 1 ns to about 1 μs. Without being limited to any particular theory, a longer pulse width may enhance the strength of the induced PA signal and a shorter pulse width may reduce the scan time needed to acquire PA imaging data. In one aspect, the pulse width may be about 5 ns.

In an aspect, the laser may produce laser pulses that are directed into the top skull surface at a laser fluence of less than about 40 mJ/cm². In another aspect, the laser fluence at the skull surface may be less than about 20 mJ/cm². Without being limited to any particular theory, the laser fluence used to obtain PA imaging data may be influenced by the laser wavelength; shorter wavelength laser pulses may be delivered at lower fluences than corresponding longer wavelength laser pulses. In one aspect, the laser fluence may be selected to fall below the maximum fluence set out in the laser safety standards of the American National Standards Institute (ANSI). In another aspect, the laser pulses may be delivered at a fluence of above 40 mJ/cm² to provide laser therapy in addition to obtaining PAT imaging data.

In an aspect, the laser pulse width and laser fluence may be selected to deliver an amount of energy sufficient to generate a detectable PA signal at the desired area of interest. Without being limited to any particular theory, the laser pulse width and laser fluence delivered by the laser may be selected to elevate the target tissue within the area of interest at least about 1 millidegrees Celsius, corresponding to a pressure increase of about 800 Pa. This pressure increase is thought to be associated with a minimum detectable PA signal using ultrasonic transducers known in the art.

The PAT system used to acquire the PAT imaging signal may further include one or more ultrasonic transducers. In one aspect, one ultrasonic transducer may be operatively connected to a translation module to translate the ultrasonic transducer in a scanning pattern to obtain the PAT imaging data suitable for reconstruction of a two-dimensional and/or three-dimensional PAT image. In another aspect, the PAT system may include an array of ultrasound transducers to detect the acoustic signals generated by the tissues within the area of interest in response to illumination by the one or more laser pulses. In one aspect, the array of ultrasound transducers may be a ring array. The ring array may then be translated stepwise in the z-direction (i.e. in a cranial-caudal direction) to acquire a 3D PAT image. In another aspect, multiple ultrasonic transducers and/or multiple ultrasonic transducer arrays may be utilized to accelerate data acquisition and to enable real-time PAT imaging.

In an additional aspect, PA imaging data may be obtained using multiple laser wavelengths to compute oxygen saturation of hemoglobin, to observe functional activities of the human cerebral cortex, or to implement other known PAT functional imaging methods known in the art. In these additional aspects, PAT may be used for monitoring the blood-related pathological and physiological status of human brains.

In one additional aspect, a photon recycling device described herein below may be applied to redirect reflected light back into the subject to enhance the illumination provided by the PA imaging system with no associated increase in laser pulse fluence from the laser of the PA imaging system.

III. Device for Photon Recycling

A photon recycling device may be used to increase light transmittance through the skull while obtaining PA imaging data using the PA imaging system. In various aspects, a device for photon recycling may include, but is not limited to, a cylinder body, an opening, and at least one concave lens. The cylinder body may include a first surface and a second surface. The second surface may be a concave curved surface. The opening may extend from about the center of the first surface to the vertex of the curved second surface. The opening may include at least one convex lens to expand light that enters from the first surface of the cylinder, through the opening, and onto the subject. Light reflected from the surface of the subject's head may be redirected down to the subject by the curved surface of the photon recycling device.

The cylinder body may be made of a solid material. In an aspect, the cylinder body may be made from plastic polyvinyl. In various aspects, the size of the cylinder body may depend on the size of the skull to be imaged using the device. In an aspect the cylinder body may range from about 5 cm to about 15 cm in diameter and from about 2 cm to about 8 cm in height. In other aspects, the cylinder body diameter may range from about 5 cm to about 9 cm, from about 7 cm to about 12 cm, and from about 10 cm to about 15 cm. In additional aspects, the cylinder body height may range from about 2 cm to about 4 cm, from about 3 cm to about 5 cm, from about 4 cm to about 6 cm, from about 5 cm to about 7 cm, and from about 6 cm to about 8 cm. In one aspect, the cylinder body may be about 7.6 cm in diameter and about 5.5 cm in height.

The device for photon recycling may include an opening extending from the top surface of the cylinder body to the lower surface of the cylinder body. This opening may be co-axially drilled into the cylinder body of the device. The opening may allow for the transmission of a laser light through the body of the device. The diameter of the opening may be minimized to reduce the amount of light reflecting off the surface of the skull and escaping out through the opening. This arrangement will increase the likelihood that any reflected light from the head of the subject will be redirected back down to the skull from the photon recycling device.

In an aspect, the opening within the photon recycling device may range from about 0.5 cm to about 3 cm in diameter and from about 0.5 cm to about 4 cm in height. In various aspects, the opening diameter may range from about 0.5 cm to about 1.5 cm, from about 1 cm to about 2 cm, from about 1.5 cm to about 2.5 cm, and from about 2 cm to about 3 cm. In various aspects, the opening height may range from about 0.5 cm to about 1.5 cm, from about 1 cm to about 2 cm, from about 1.5 cm to about 2.5 cm, from about 2 cm to about 3 cm, from about 2.5 cm to about 3.5 cm, and from about 3 cm to about 4 cm. In an additional aspect, the opening may be about 2.54 cm in diameter and about 2 cm in height.

The lower surface of the cylinder body may be formed into a concave curved surface. The vertex of the concave curved surface may be connected to the opening. In an aspect, the curved surface may be a parabolic surface. A reflective coating may cover the curved surface in an aspect. Non-limiting examples of suitable reflective coatings include metallic coatings such as silver or aluminum, and white coatings such as titanium white pigment. The reflective coating may be mixed with an epoxy compound for application to the curved surface. The curved surface with the reflective coating may be further smoothed to improve light reflectivity.

Figure 26:
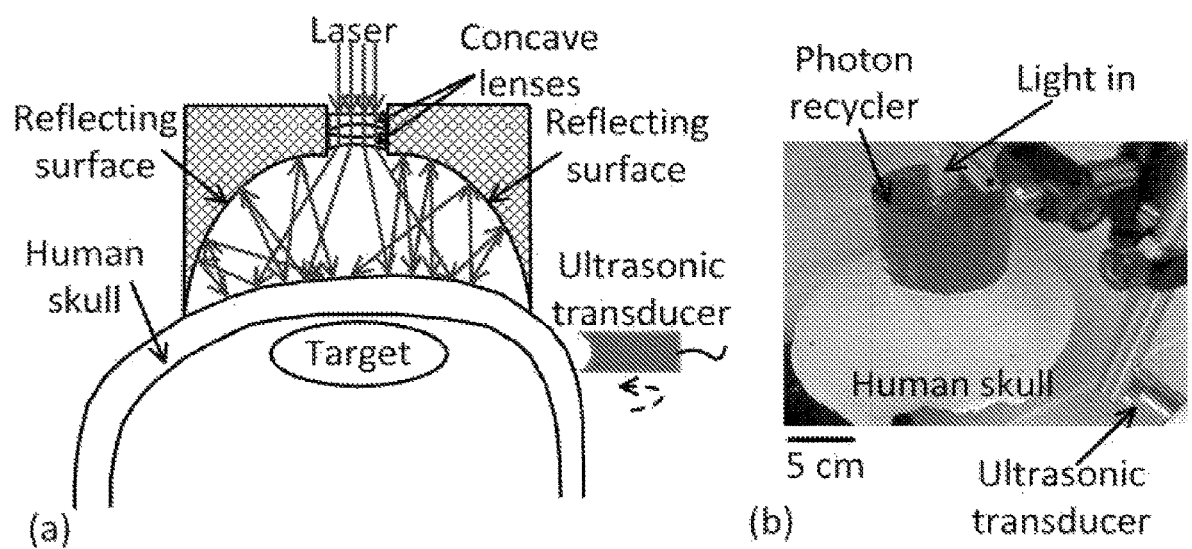
FIG. 26A is a schematic illustration of a photon recycling device reflecting back-scattered photons back to a human skull during the acquisition of PAT imaging data.
FIG. 26B is a photograph of a PAT system with a photon recycling device in one aspect.

A schematic and a photograph of the PAT system with the photon recycling device are shown in FIGS. 26A and 26B, respectively. The photon recycling device may be positioned on top of a human skull to recycle the light scattered off of the skull. The light beam may propagate through the central opening of the photon recycling device, and may then be expanded by passing through at least one concave lens. In an aspect, the opening may include two concave lenses. The opening may include a plano-concave lens (12.7 mm aperture, 0.42 NA) and a bi-concave lens (12.7 mm aperture, 0.5 NA) to illuminate the skull in one aspect.

In an aspect, use of the photon recycling device may improve the photoacoustic signal-to-noise ratio by a factor of about 2.4 or more.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus may be considered to constitute preferred modes for its practice. However, those of skill in the art should, in light of the present disclosure, appreciate that many changes may be made in the specific embodiments which are disclosed and still obtain a like or similar result without departing from the spirit and scope of the invention.

Example 1

Reconstruction of Biological Phantoms

The reconstruction methodology is comprised of two primary steps. First, the spatially varying SOS and density distributions of the to-be-imaged subject's skull are determined by use of adjunct X-ray CT data. These distributions are subsequently employed with the time-reversal image reconstruction method described above for estimation of $p_0(r)$ within the brain tissue from knowledge of the measured data $\{\hat{p}(r_m, t)\}_{m=1}^{M}$.

Two biological phantoms that employed a monkey skull were employed in the experimental studies to demonstrate the effectiveness of the present methodology. The first phantom was the head of an 8 month old rhesus monkey that was obtained from the Wisconsin National Primate Research Center. The hair and scalp were removed from the skull. A second, more simple, phantom was constructed by removing the brain of the monkey and replacing it by a pair of iron needles of diameter 1 mm that were embedded in agar. This was accomplished by cutting off the calvaria to gain access to the brain cavity.

The wavefront aberration problem encountered in transcranial PAT is conjugate to one encountered in transcranial focusing of high-intensity ultrasound for therapy applications. Both problems involve a one-way propagation of ultrasound energy through the skull and both require that the wavefront aberrations induced by the skull be corrected. The problems differ in the direction of the propagating acoustic wavefields. The feasibility of utilizing skull information derived from adjunct X-ray CT image data to correct for wavefield aberrations in transcranial focusing applications has been demonstrated. As described above, this method was adopted for determining estimates of $c_0(r)$ and $\rho_0(r)$, and thereby characterizing the acoustic properties of the subject's skull, from adjunct X-ray CT data.

Example 2

Images of Biological Phantoms

To accommodate the 2-D PAT imaging system and 2-D image reconstruction method, imaging phantoms were moved to the image plane, approximately 2 cm below the top of the skull. Note that this was not the plane in which the cortical vessels are normally found; the primate brain was moved to align the cortical vessels with the imaging plane. For in-vivo transcranial PAT applications in which the cortical structure is of interest, the geometry of the skull necessitates a full 3-D treatment of the image reconstruction problem. Additionally, accurate measurement of the transducer's electrical impulse response (EIR) and subsequent deconvolution of its effect on the measured data may further improve image reconstruction accuracy. Alternative reconstruction methods to the time-reversal image reconstruction method employed in this study may yield additional improvements in image quality.

Virtual point detectors were developed and applied for transcranial PAT of the monkey brain. Compared to flat ultrasonic transducers, virtual point ultrasonic transducers greatly improved the tangential resolution, radial resolution, and SNR at the periphery. The virtual point transducer provided a 10 times greater field-of-view (FOV) than finite aperture unfocused transducers, which enabled large primate imaging. The increase in the acceptance angle of the detectors enable imaging of a larger FOV, and thus the object shapes in the reconstructed images may be well preserved, even when the target may be far from the scanning center. Compared to the negative-lens ultrasonic transducers, the virtual point ultrasonic detectors provide an improved SNR (about 15% improvement) and avoid reverberation artifacts in the reconstructed images.

The incorporation of the virtual point ultrasonic detector allowed PAT imaging of a monkey brain cortex. A reconstruction methodology for transcranial PAT to mitigate skull-induced aberration in the reconstructed image was also demonstrated. The reconstruction methodology may reduce artifact levels as compared to use of existing back-projection reconstruction methods. The cerebral cortex of a monkey brain was accurately imaged transcranially through up to two skulls ranging from 4 to 8 mm in thickness. The mass density and speed of sound distributions of the skull were estimated from adjunct X-ray CT image data and utilized with a time-reversal method to mitigate artifacts in the reconstructed image due to acoustic aberration. The oxygenation saturation ($sO_2$) in blood phantoms through a monkey skull was also imaged and quantified, with results consistent with measurements by a gas analyzer. The oxygenation saturation ($sO_2$) in blood phantoms through a monkey skull was also imaged and quantified, with results consistent with measurements by a gas analyzer.

The results suggested that PAT imaging may overcome the optical and ultrasound attenuation effects of a relatively thick skull. Further, the imaging aberrations caused by skull acoustic discontinuities may be ameliorated to a great extent, and that PAT brain cortex imaging of large animals may be feasible. Therefore, PAT imaging methods may be potentially used for monitoring the blood-related pathological and physiological status of human brains, especially for neonatal brains before the closure of fontanelles.

Example 3

Images of Needle Phantom

Figure 6:
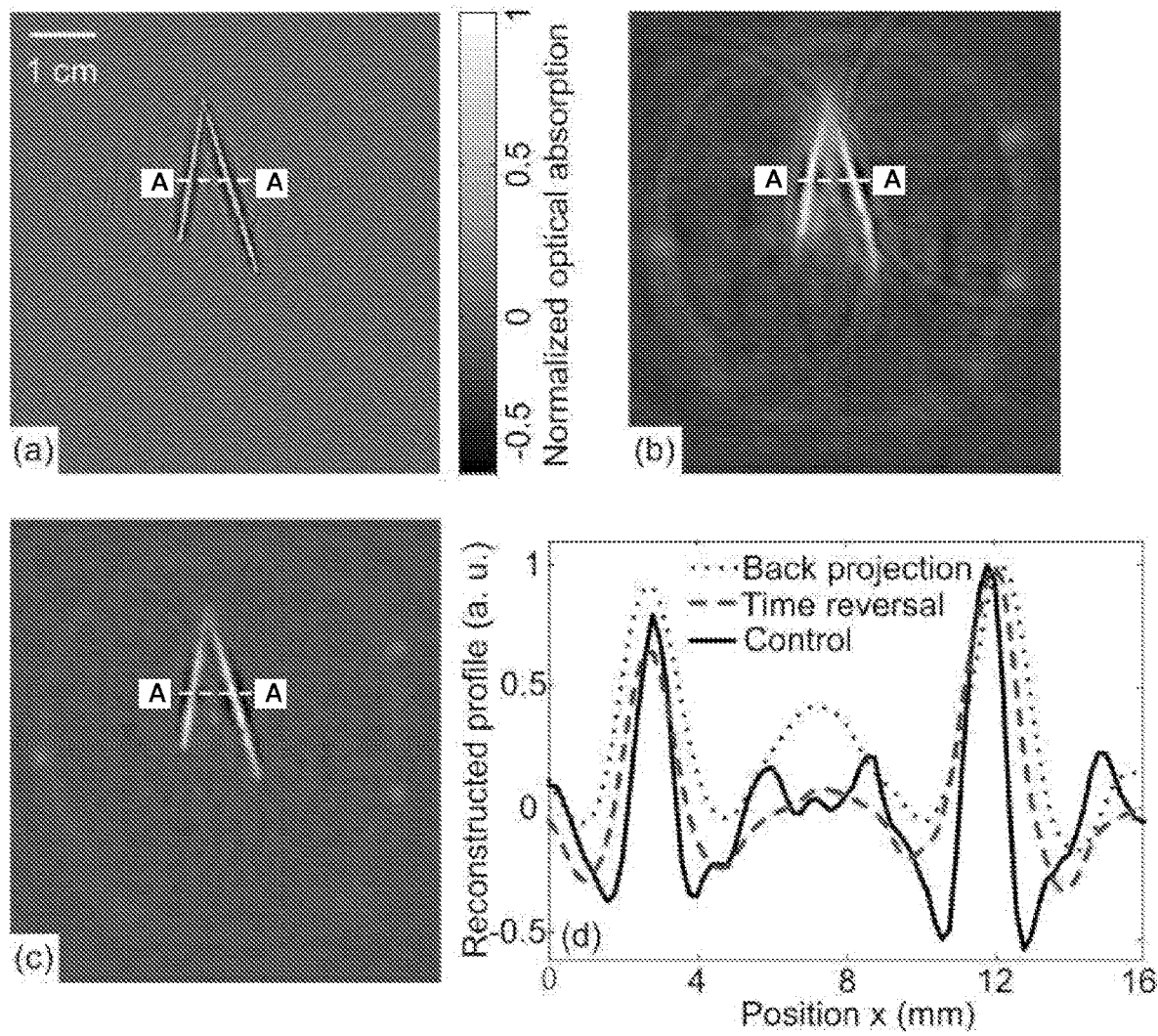
FIGS. 6A-6C are two-dimensional PA images of a reference object consisting of crossed pins in an agar matrix in which the reference object is exposed to the imaging system or situated within a skull.
FIG. 6D is a graph summarizing the optical absorption profiles taken along line A-A superimposed on each of the images of FIGS. 6A-C.

The reconstructed images corresponding to the head phantom containing the needles are displayed in FIG. 6. FIG. 6A displays the control image of the needles, without the skull present, reconstructed by use of a back-projection method. FIGS. 6B and 6C display reconstructed images of the phantom when the skull was present, corresponding to use of back-projection and the time-reversal reconstruction method utilized to estimate the SOS and density maps, respectively. All images were normalized to their maximum pixel value, and were displayed in the same grey-scale window. Due to the skull-induced attenuation of the high-frequency components of the PA signals, which was not compensated for in the reconstruction process, the spatial resolution of the control image in FIG. 6A appears higher than the images in FIGS. 6B and 6C. However, the image reconstructed by use of the time-reversal method in FIG. 6C contains lower artifact levels and has an appearance closer to the control image than the image reconstructed by use of the back-projection method in FIG. 6B. This is expected, since the time-reversal method compensates for variations in the SOS and density of the skull while the back-projection method does not.

These observations were corroborated by examination of profiles through the three images shown in FIG. 6D, which correspond to the rows indicated by the superimposed dashed lines on the images. The solid, dotted, and dashed lines correspond to the reconstructed control image, and images reconstructed by use of the back-projection and time-reversal methods, respectively. The average full-width-at-half-maximum of the two needles in the images reconstructed by use of the time-reversal method was reduced by 8% compared to the corresponding value computed from the images obtained via the back-projection method.

Example 4

Images of Monkey Brain Phantom

Figure 7:
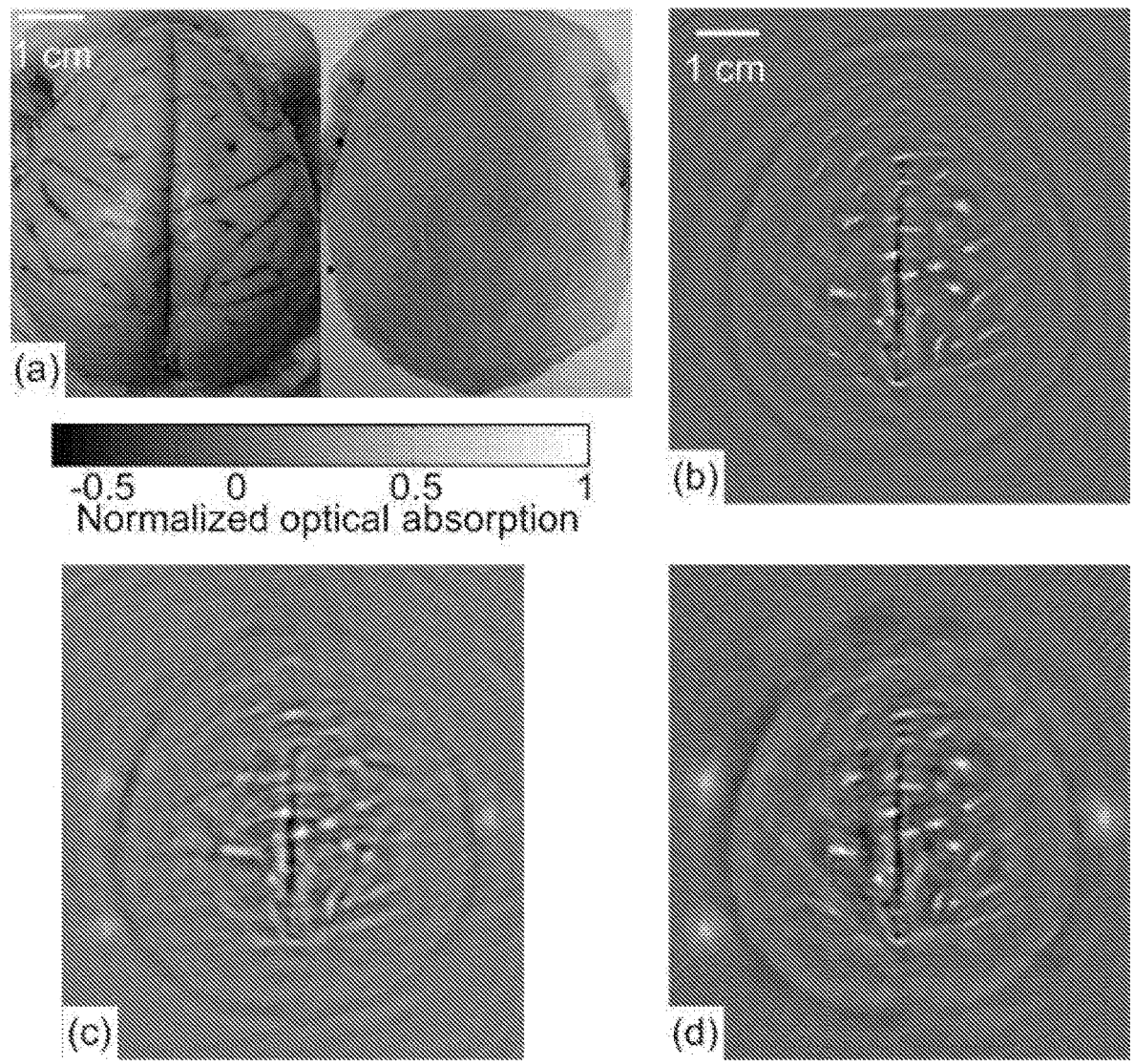
FIG. 7A is a photograph of a brain specimen and skull.
FIG. 7B is a two-dimensional PA image of the brain specimen with the skull cap removed that was reconstructed using a back-projection method.
FIG. 7C is a two-dimensional PA image of the brain specimen inside the skull that was reconstructed using a back-projection method.
FIG. 7D is a two-dimensional PA image of the brain specimen inside the skull that was reconstructed using a back time-reversal method.

The reconstructed images corresponding to the head phantom containing the brain are displayed in FIG. 7. FIG. 7A displays photographs of the cortex and outer surface of the skull. FIG. 7B displays the control image (skull absent) reconstructed by use of the back-projection method. The images of the complete phantom (skull present) reconstructed by use of the back-projection and time-reversal methods are shown in FIGS. 7C and 7D, respectively. All images have been normalized to their maximum pixel value, and are displayed in the same grey-scale window. As observed above for the needle phantom, the brain image reconstructed by use of the time-reversal method in FIG. 7D contains lower artifact levels and has an appearance closer to the control image than the image reconstructed by use of the back-projection method in FIG. 7C.

Figure 8:
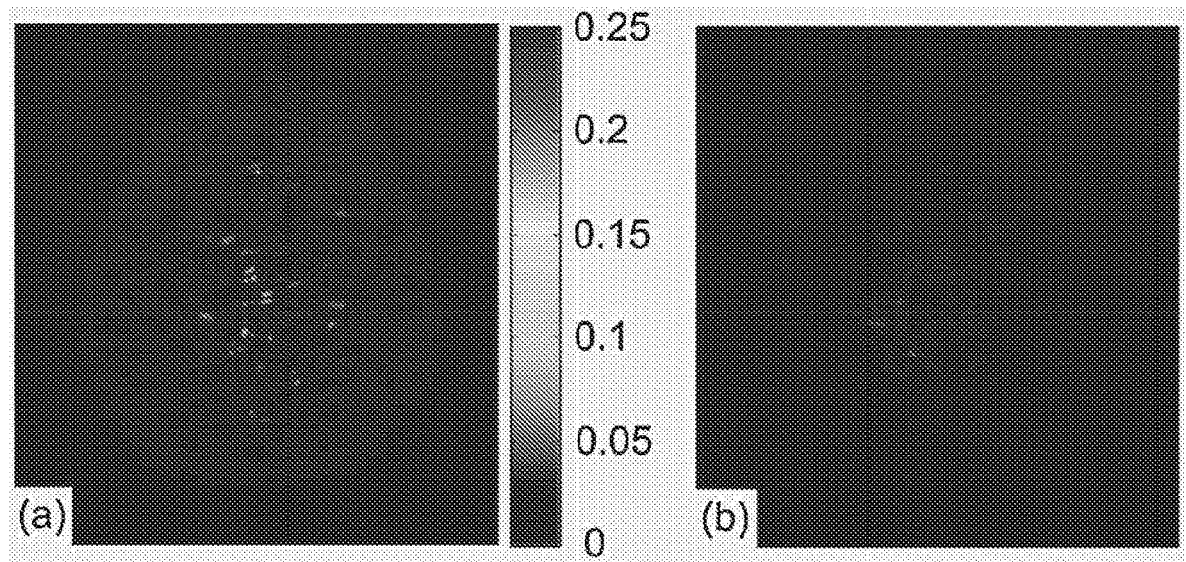
FIG. 8A is a difference image of the brain specimen obtained by subtracting the image of FIG. 7B from the image of FIG. 7C.
FIG. 8B is a difference image of the brain specimen obtained by subtracting the image of FIG. 7B from the image of FIG. 7D. In both cases, the reference image is the back-projection PAT reconstruction of the brain specimen with the skull removed.

This observation was quantified by computing error maps that represented the pixel-wise squared difference between the control and reconstructed images with the skull present. FIGS. 8A and 8B displays the error maps between the control image and the images reconstructed by use of the back-projection and time-reversal methods, respectively. The error maps were computed within the region interior to the skull, which is depicted by the red contours superimposed on FIG. 5B-5D. Additionally, the root mean-squared difference (RMSD) was computed by computing the average values of the difference images. The RMSD corresponding to the back-projection and time-reversal results were 0.085 and 0.038. These results confirm that the image reconstructed by use of the time-reversal method, which compensated for the acoustic properties of the skull, was closer to the control image than the image produced by use of the back-projection method.

Figure 9:
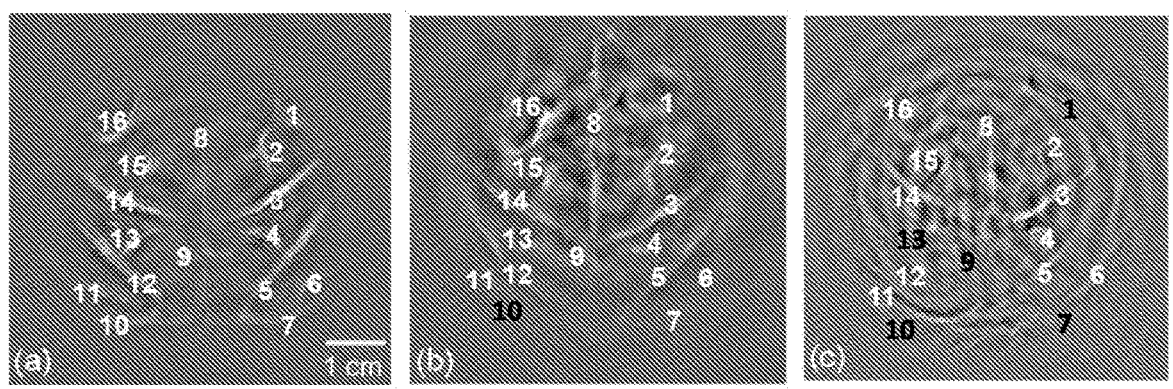
FIGS. 9A-9C are PAT images of an exposed monkey brain (FIG. 9A), the monkey brain situated beneath one skull thickness (FIG. 9B), and the monkey brain situated beneath two skull thicknesses (FIG. 9C). The visible and invisible blood vessels are marked with white and black numbers, respectively.

FIG. 9 shows PAT images of the monkey brain reconstructed by use of a back-projection method with and without the cranium and dura mater. FIG. 9A shows the PAT image of the monkey brain without the skull, which serves as a reference image. FIG. 9B shows the PAT image of monkey brain with one skull, whose thickness ranged from 2-4 mm. The skull thickness was increased by covering a second thicker skull on the first skull, where the second skull thickness ranged from 2.5-4.5 mm. FIG. 9C shows the PAT image of monkey brain with the two skull thicknesses. Blood vessels are associated in the different images by labeling them with the same numbers. The visible blood vessels are marked with white bold numbers, while the invisible blood vessels are marked with green numbers. In FIG. 9B, all of the blood vessels except #10 are visible in the reconstructed image with one skull present. In the images corresponding to two skulls present, half of the blood vessels (#2, 3, 4, 5, 6, 8, 11, 12, 14, 15, and 16) may still be clearly imaged in FIG. 9C. The mean full width at half maximum (FWHM) diameter of the reconstructed blood vessels, with two skull thicknesses and without any skull, is 0.83 mm and 0.41 mm respectively.

Figure 10:
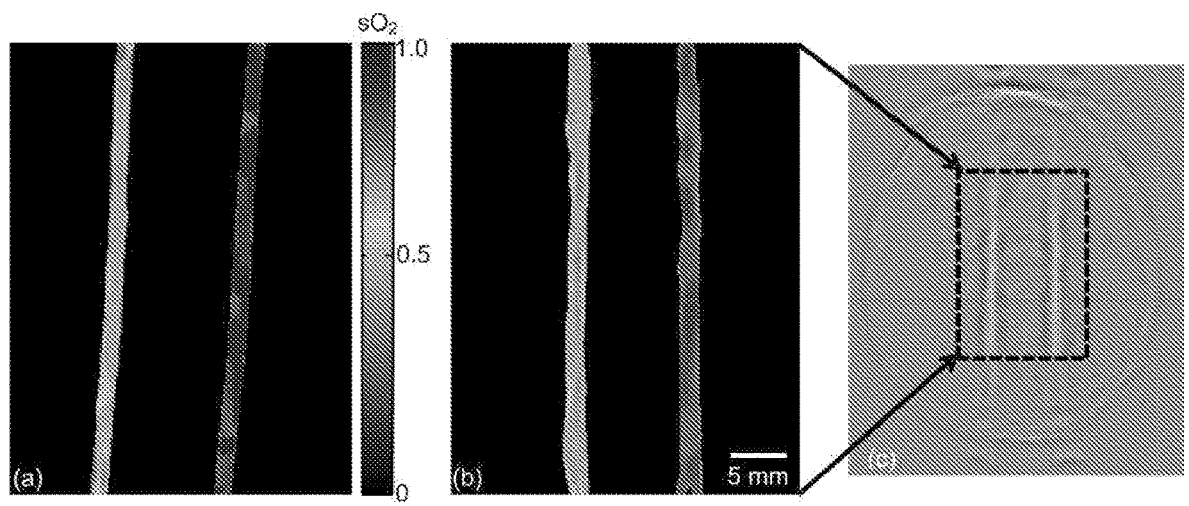
FIGS. 10A-10B are PAT image of the $sO_2$ variation within two tubes filled with bovine blood obtained using PA illumination wavelengths of 630 nm and 640 nm.
FIG. 10C is a structural PAT image of the two tubes reflecting the total hemoglobin concentration that was acquired at an optical wavelength of 630 nm.

The PAT image of the two tubes under the skull is shown in FIG. 10C, corresponding to use of laser light of wavelength 630 nm. The $sO_2$ maps of the two tubes without and with the skull are shown in FIGS. 10A and 10B. By comparing this result with the result measured from a gas analyzer, the computed $sO_2$ accuracy was determined to be about 8% in the PAT image corresponding to the skull present case. This suggests that transcranial PAT imaging of $sO_2$ values is feasible, and PAT may potentially be employed for functional primate brain imaging.

Figure 11:
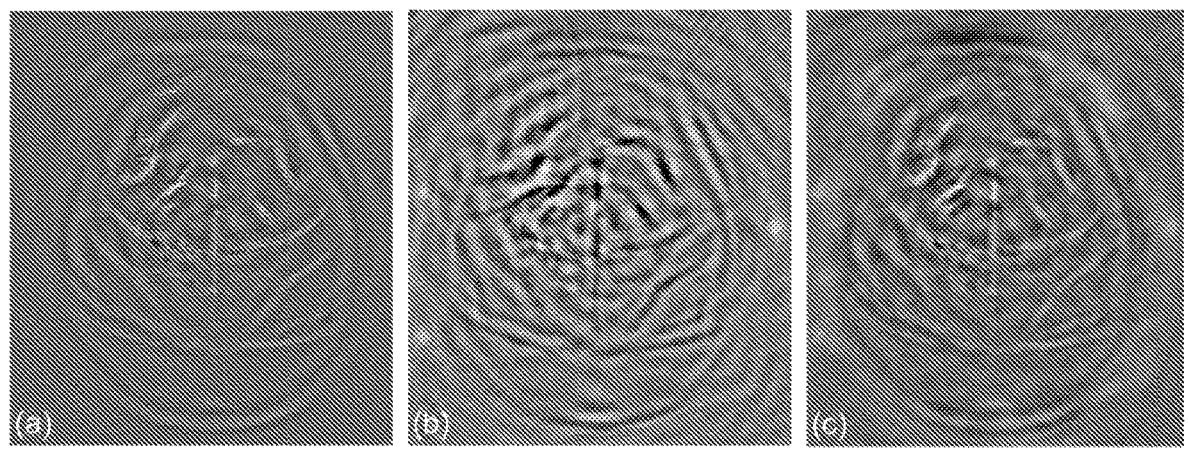
FIG. 11 is a reconstructed image of the monkey brain without skull using back-projection (FIG. 11A), with skull present using the back-projection method (FIG. 11B), with skull present using a time reversal method (FIG. 11C).

FIG. 11 shows the effectiveness the reconstructed methodology to mitigate image artifacts due to acoustic aberration caused by the skull. FIG. 11A is the PAT image without a skull present (the reference image) reconstructed by the back-projection method. PAT images of the monkey brain with a skull present reconstructed by use of the back-projection and time-reversal methods are shown in FIGS. 11B and 11C, respectively. All images have been normalized to their maximum pixel value, and are displayed in the same grey-scale window. As may be seen, the image reconstructed by use of the time-reversal method in FIG. 11C contains reduced artifact levels as compared to FIG. 11B and is much closer in appearance to the reference image. Note that the blood vessels near the skull boundary in FIG. 11C are well compensated for and much clearer than in the image without aberration compensation (FIG. 11B).

Example 5

Adjunct Imaging of Biological Phantoms

The monkey skull that was part of both phantoms described in Example 1 was imaged using an X-ray CT scanner (Philips Healthcare, Eindhoven, The Netherlands) located at Washington University in St. Louis. Prior to imaging, three fiducial markers were attached to the skull to facilitate co-registration of the determined SOS and density maps with the reference frame of the PAT imaging system. The three fiducial markers [see FIG. 4A] were iron balls of diameter of 1.5 mm and were carefully attached to the outer surface of the skull. The fiducial markers were located in a transverse plane that corresponded to the to-be-imaged 2-D slice in the PAT imaging studies described below. In the X-ray CT studies, the tube voltage was set at 130 kV, and a tube current of 60 µA was employed. Images were reconstructed on a grid of 700 by 700 pixels of dimension d=0.1 mm. This pixel size is much less than the smallest wavelength (0.5 mm) detected by the ultrasound transducer used in the PAT imaging studies described below. This precision is sufficient to accurately model acoustic wave propagation in the skull by using the k-space pseudospectral methods. The reconstructed CT image is displayed in FIG. 4A.

From knowledge of the CT image, the porosity map $\phi_k$ was computed according to Eqn. (VI). Subsequently, the density and SOS maps $\rho_k$ and $c_k$ were computed according to Eqns. (VII) and (VIII). Images of the estimated $c_k$ and $\rho_k$ maps are displayed in FIGS. 4B and 4C. To corroborate the accuracy of the adopted method for estimating the skull's SOS and density distributions from X-ray CT data, i.e., Eqns. (VII) and (VIII), direct measurements of the skull's average SOS along ray-paths perpendicular to the skull surface at five locations were acquired. This was accomplished by use of a photoacoustic measurement technique depicted in FIG. 5A. Additionally, the average density of the skull was computed and compared to the average computed from the values estimated from the X-ray CT data. The results show that the directly measured average SOS and density are very close (about 1 to 6%) to the estimated values from CT data. These results corroborate the adopted method for estimating the skull's SOS and density distributions from adjunct X-ray CT data.

Example 6

PAT Imaging Studies

Data Acquisition

After the skull's SOS and density distributions were estimated from the adjunct X-ray CT data, the two phantoms (that included the skulls) were imaged by use of the PAT imaging system shown in FIG. 5B. Images of the two phantoms with the skull removed, i.e., images of the extracted monkey brain and crossed needles embedded in agar, were also acquired, which will serve as control images. The imaging system employed a 2-D scanning geometry and has been employed in previous studies of PAT imaging of monkey brains. The imaging plane and fiducial markers were chosen to be approximately 2 cm below the top of the skull, such that the imaging plane was approximately normal to the skull surface at that plane. The phantoms (crossed needles and the primate cortex) were moved to the imaging plane, so that the amount of acoustic energy refracted out of the imaging plane was minimized. Additionally, the system was aligned to ensure the scanning plane and the imaging plane coincided.

Figure 5:
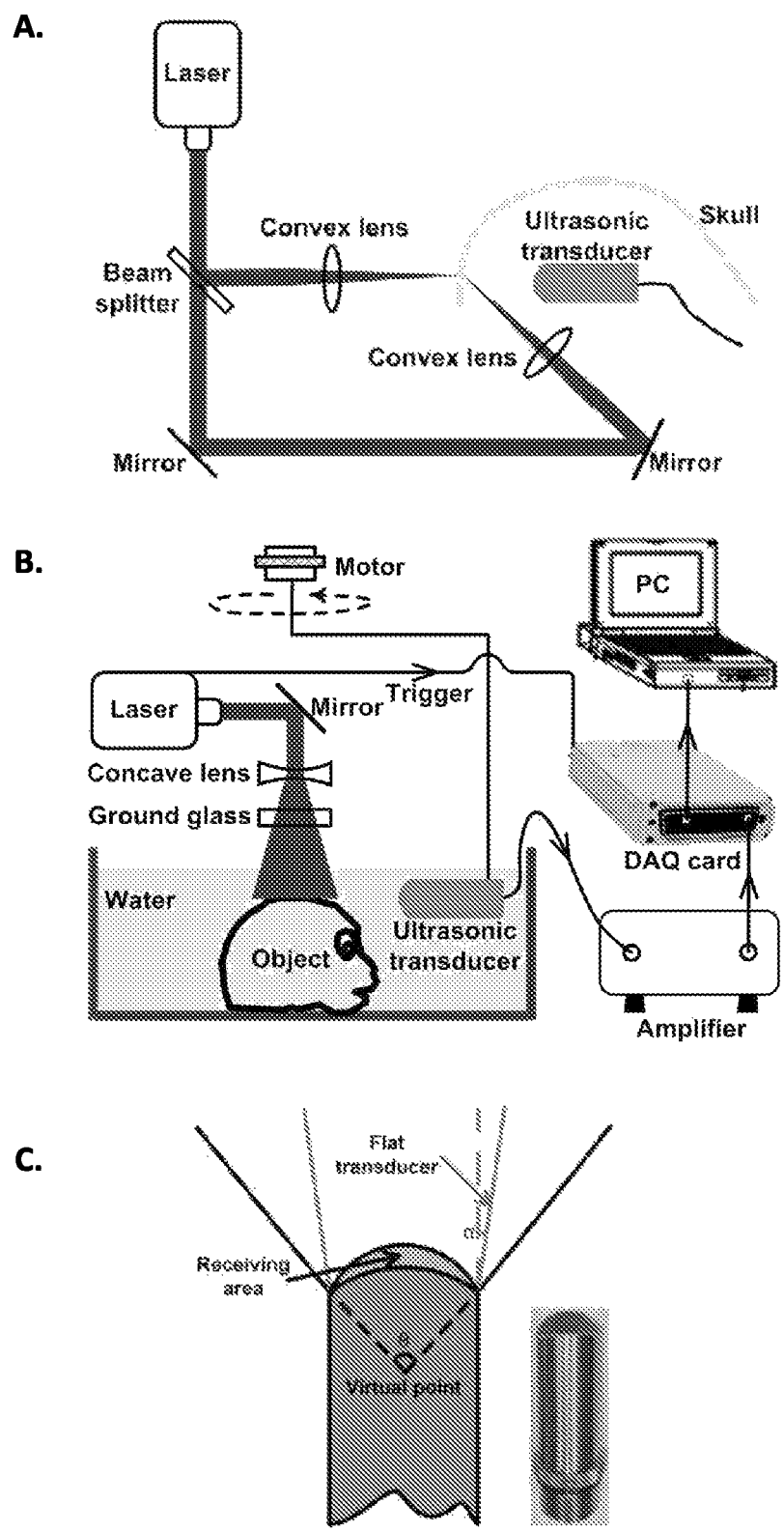
FIG. 5A is a schematic diagram showing the arrangement of measurement devices of a transcranial PAT system in one aspect.
FIG. 5B is a schematic diagram showing the arrangement of devices of a transcranial PAT system in another aspect.
FIG. 5C is a cross-sectional view of a virtual point ultrasonic detector in an aspect.

The phantoms were immersed in a water bath and irradiated by use of a tunable dye laser from the top (through the skull for the cases when it was present) to generate PA signals. The laser (NS, Sirah), which was pumped by a Q-switched Nd:YAG laser (PRO-35010, Newport) operating at a wavelength of 630 nm with a pulse repetition rate of 10 Hz, was employed as the energy source. The laser beam was expanded by use of a piece of concave lens and homogenized by a piece of ground glass before illuminating the target. The energy density of the laser beam on the skull was limited to 8 mJ/cm$^2$ (within the ANSI standard), which was further attenuated and homogenized by the skull before the laser beam reached the object. As shown in FIG. 5, a circular scanning geometry with a radius of 9 cm was employed to record the PA signals. A custom-built, virtual point ultrasonic transducer was employed that had a central frequency of 2.25 MHz and a one-way bandwidth of 70% at −6 dB. Additional details regarding this transducer have been published elsewhere. The position of the transducer was varied on the circular scan trajectory by use of a computer-controlled step motor. The angular step size was 0.9 degrees, resulting in measurement of $\hat{p}(r_m, t)$ at m=1, . . . , M=400 locations on the scanning circle. The total acquisition time was approximately 45 min.

The PA signals received by the transducer were amplified by a 50-dB amplifier (5072 PR, Panametrics, Waltham, Mass.), then directed to a data-acquisition (DAQ) card (Compuscope 14200; Gage Applied, Lockport, Ill.). The DAQ card was triggered by the Q-switch signal from the laser to acquire the photoacoustic signals simultaneously. The DAQ card features a high-speed 14-bit analog-to-digital converter with a sampling rate of 50 MS/s. The raw data transferred by the DAQ card was then stored in the PC for imaging reconstruction.

Example 7

PAT Imaging Studies

Image Reconstruction

Image reconstruction was accomplished in two steps: (1) registration of the SOS and density maps of the skull to the PAT coordinate system and (2) utilization of a time-reversal method for PAT image reconstruction in the corresponding acoustically heterogeneous medium.

Figure 4:
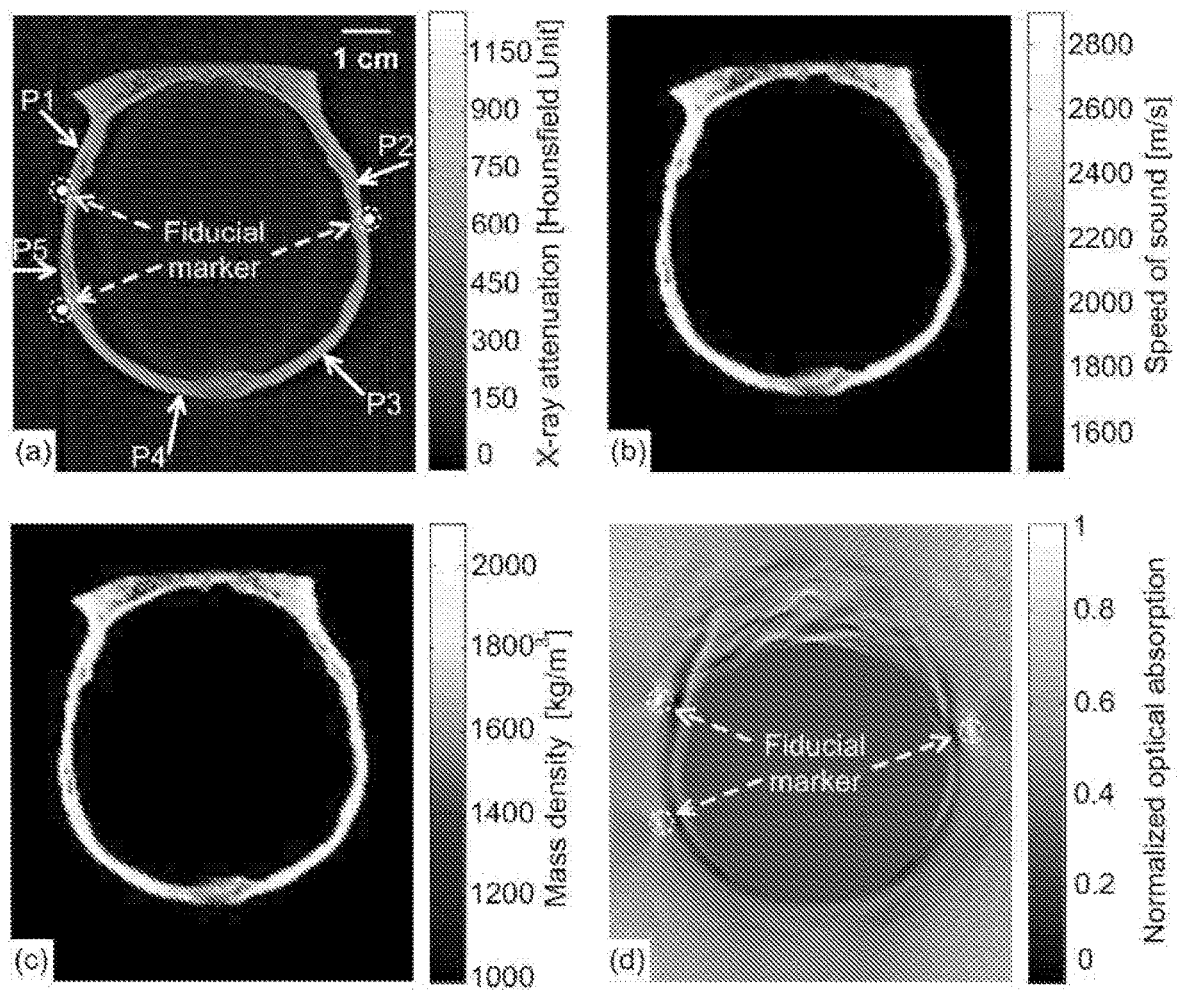
FIG. 4A is a two dimensional CT image coincident with the PA imaging plane of the skull with fiducial markers labeled.
FIG. 4B is a speed of sound (SOS) map derived from the CT data of FIG. 4A using Eqn. (III).
FIG. 4C is a density map derived from the CT data of FIG. 4A using Eqn. (II).
FIG. 4D is a PAT image of monkey head phantom reconstructed using of a half-time method.

The estimated SOS and density maps $c_k$ and $\rho_k$ were registered to the frame-of-reference of the PAT imaging as follows. From knowledge of the PAT measurement data, a scout image was reconstructed by use of a half-time reconstruction method. This reconstruction method may mitigate certain image artifacts due to acoustic aberrations, but the resulting images will, in general, still contain significant distortions. The PAT image of monkey head phantom (with brain present) reconstructed by use of the half-time method is displayed in FIG. 4D. Although the image contains distortions, the three fiducial markers are clearly visible. As shown in FIG. 4A, the fiducial markers were also clearly visible in the X-ray CT image that was employed to estimate the SOS and density maps of the skull. The centers of the fiducial markers in the X-ray CT and PAT images were determined manually. From this information, the angular offset of the X-ray CT image relative to the PAT image was computed. The SOS and density maps were downsampled by a factor of two, to match the pixel size of the PAT images, and rotated by this angle to register them with the PAT images.

The re-orientated SOS and density maps were employed with the k-space time-reversal PAT image reconstruction method. The numerical implementation of this method provided in the Matlab k-Wave Toolbox was employed. The measured PA signals were pre-processed by a curvelet denoising technique prior to application of the image reconstruction method. The initial pressure signal, $p_0(r)$, was reconstructed on a grid of 1000×1000 pixels of dimension 0.2 mm. For comparison, images were also reconstructed on the same grid by use of a back-projection reconstruction method. This procedure was repeated to reconstruct images of both phantoms and the corresponding control phantoms (phantoms with skulls removed).

Example 8

Validation of Speed-of-Sound and Density Maps

The density and speed-of-sound of the skull were directly measured to corroborate the accuracy of the adopted method for estimating the skull's SOS and density distributions from X-ray CT data. By using the water displacement method, the measured average density of the monkey skull $\bar{\rho}_{wd}$ is 1890 kg/m$^3$. The average density of the skull $\bar{\rho}^{ct}$ may also be estimated from CT data:

$$\bar{\rho}_{ct} = \frac{\sum_k \Phi_k \rho^w + (w - \Phi_k)\rho^s}{N}, \qquad \text{Eqn. (LIII)}$$

where $\rho^w=1000$ kg/m$^3$ is the density of water, $\rho^s=2100$ kg/m$^3$ is the density of skull, $\phi_k$ is the porosity of the $k^{th}$ pixel of the skull, and N is the total number of pixels of the skull in the CT image. The estimated average density of the skull, $\bar{\rho}_{ct}=1910$ kg/m$^3$ is very close (about 1%) to the measured value $\bar{\rho}_{wd}=1890$ kg/m$^3$.

The SOS in the skull was measured using a photoacoustic approach, as shown in FIG. 5B. A laser beam was split by use of a beam splitter and directed by mirrors to two convex lenses. The two convex lenses (NA≈0.04, depth of focus about 300 mm) focused the laser beam on the inner and outer surface of the skull, and the line connecting the two focused beam spots (about 80 microns) was perpendicular to the skull surface. The ultrasonic transducer was placed coaxially with the laser spots; therefore, the average SOS $\bar{c}_{pa}$ between the two laser spots was calculated by:

$$\bar{c}_{pa} = \frac{h}{\frac{h}{c^w} - t_d},\qquad \text{Eqn. (LIV)}$$

where $t_d$ is the time delay between the PA signals from the inner and outer surfaces of the skull, $c^w=1480$ ms is the speed-of-sound in water, and h is the thickness of the skull at the laser spots. $\bar{c}_{pa}$ was measured at the five locations on the skull that are indicated in FIG. 4A. The measured SOS values are displayed in the second column of Table 1. Table 1 shows the measured average SOS ($c_{pa}$) via the PA experiment (column 2) and the estimated average SOS ($c_{ct}$) from the CT measurements (column 3) for the five measurement locations [see FIG. 4A].

TABLE 1

| Position | SOS (PA) in m/s | SOS (CT) in m/s |
|---|---|---|
| 1 | 2790 ± 90 | 2720 |
| 2 | 2740 ± 80 | 2830 |
| 3 | 2780 ± 60 | 2860 |
| 4 | 2620 ± 100 | 2720 |
| 5 | 2590 ± 160 | 2430 |

The corresponding average SOS values were also computed by use of the X-ray CT image data and compared to the measured values. In order to determine the five locations on the CT image that correspond to the measurement locations described above, the arc lengths were measured between the fiducial markers and the measured locations. Then the average SOS $\bar{c}_{ct}$ at these locations may be estimated from CT data [derived from Eqn. (XII)]:

$$\bar{c}_{ct} = \frac{h}{\sum_i \frac{d}{\Phi_i c^w + (1-\Phi_i)c^s}},\qquad \text{Eqn. (LV)}$$

where $\phi_i$ is the porosity of the $i^{th}$ pixels on the line connecting the two laser spots, and is calculated from bilinear interpolation of the neighbor pixel values in the CT image; $c^s=2900$ m/s is the speed-of-sound of skull bone, and d=0.1 mm is the resolution of the CT image. The estimated SOS at these locations are shown in the last column of Table 1. The root mean square difference between the SOS inferred from the PA experiment and the SOS inferred from the CT data is 105 m/s.

Example 9

PAT System for Brain Imaging

A PAT system was employed for monkey brain imaging, as shown in FIG. 5B. A Q-switched Nd:YAG laser (PRO-350-10, Newport) with a 6.5 ns pulse duration and a 10 Hz pulse repetition rate was used as an energy source. The laser beam was expanded by use of a piece of concave lens and homogenized by a piece of ground glass before illuminating the target. The energy density of the laser beam on the skull was controlled to 8 mJcm$^2$ (i.e. within the ANSI standard). The target sample was immersed in water and irradiated by a laser beam from the top, and an ultrasound detector scanned the sample circularly with a scanning radius of 9 cm on the plane orthogonal to the irradiation direction over 400 angles. The PA signals received by the transducer were amplified by a 50-dB amplifier (5072 PR, Panametrics, Waltham, Mass.), then directed to a data-acquisition (DAQ) card (Compuscope 14200; Gage Applied, Lockport, Ill.). The DAQ card was triggered by the Q-switch signal from the laser to acquire the PA signals simultaneously. The DAQ card features a high-speed 14-bit analog-to-digital converter with a sampling rate of 50 MSs. The raw data transferred by the DAQ card was then stored in the PC for imaging reconstruction.

The custom-built virtual point ultrasonic detector (from GE Healthcare) employed had a 2.25-MHz central frequency with 70% bandwidth. The virtual detector is equivalent to point detector in their receiving angle and FOV; however, it possesses a much greater receiving surface and sensitivity. As shown in FIG. 5C, the virtual point of the convex transducer is located behind the receiving surface. The focus is 9.7 mm behind the most protruding point on the transducer surface. The acceptance angle is defined as the angle at which the radiation power decreases more than 6 dB. The convex part of the curved surface is 2.5 mm in depth, and its cross sectional diameter is 13 mm. Thus the receiving angle is 87.8°, compared to 8.6° for a flat transducer.

Rhesus monkey heads, obtained from the Wisconsin National Primate Research Center, were immediately immersed in 10% formalin solution after harvest. The blood vessels were well maintained for PAT experiments, and the hair and scalp were removed. The dimensions of the head in the axial plane were about 8 cm×6 cm, and the laser irradiation area was approximately 5 cm×5 cm. Imaging hemoglobin oxygen saturation (sO$_2$) is significant to understand brain pathological information and hemodynamics. It is also invaluable for numerous medical applications, such as evaluating the effects of chemotherapy and radiotherapy, monitoring the healing process of wounds. As the first demonstration, two tubes with different sO$_2$ were placed directly below the skull to simulate blood vessels in the brain. The plastic tubes are transparent for light to penetrate, and one tube was filled with 98% sO$_2$ bovine blood simulating 'artery'. The other tube was filled with 67% sO$_2$ bovine blood simulating 'vein'. 630 nm and 640 nm wavelengths were used to compute the sO$_2$.

To determine the SOS and density maps of the skull for use with the time-reversal image reconstruction method, X-ray CT image data were employed. The monkey skull was attached with three fiducial markers and imaged using an X-ray CT scanner (Philips Healthcare, Eindhoven, The Netherlands) located at Washington University in St. Louis. Details regarding this system may be found in reference. From knowledge of the CT image, the porosity map $\phi_k$ was computed according to Eqn. (IX). Subsequently, the density and SOS maps $\rho_k$ and $c_k$ were computed according to Eqns. (X) and (XI). The SOS and density maps of the skull were subsequently registered to the PAT coordinate system through three fiducial markers visible in both CT image and PAT image, which was reconstructed by a half-time method. The registered SOS and density maps were employed with the k-space time-reversal PAT image reconstruction method.

Example 10

Implementation of the Forward and Backprojection Operators

Numerical studies were conducted to demonstrate the effectiveness and robustness of the proposed discretized imaging model in studies of iterative image reconstruction from incomplete data sets in 2-D and 3-D PACT. Specifically, the system matrix and its adjoint, as formulated in Section III, were employed with an iterative image reconstruction method that was designed to minimize a PLS cost function that contained a total variation (TV) penalty term. The performance of the reconstruction method was compared to an existing TR-based reconstruction method.

The k-space pseudospectral method for numerically solving the photoacoustic wave equation was implemented in the MATLAB k-Wave toolbox. This toolbox was employed to compute the action of H. To prevent acoustic waves from leaving one side of the grid and re-entering on the opposite side, an anisotropic absorbing boundary condition called a perfectly matched layer (PML) was employed to enclose the computational grids. The performance of the PML was dependent on both the size and attenuation of the layer. A PML thickness of 10 grid points, together with a PML absorption coefficient of 2 nepers per meter, were found to be sufficient to reduce boundary reflection and transmission for normally incident waves. To accurately and stably model wave propagation, the temporal and spatial steps were related by the CourantFriedrichsLewy (CFL) number as:

$$\Delta t \leq \frac{CFL \Delta r_{min}}{c_{max}} \qquad \text{Eqn. (LVI)}$$

where $\Delta r_{min}$ is the minimum grid spacing, and a CFL number of 0.3 typically provides a good compromise between computation accuracy and speed.

The action of the backprojection matrix on the measured pressure data $\hat{p}$ was implemented according to Eqn. (LII). It may be verified that $p^{bp} = H^t \hat{p}$ may be computed as:

$$v^{M-1} = \theta^T \hat{p}_{M-1} \qquad \text{Eqn. (LVII)}$$

$$v^{m-1} = \theta^T \hat{p}_{m-1} + W^T v^m \quad m = M-1, \ldots, 1 \qquad \text{Eqn. (LVIII)}$$

$$p^{bp} = \tau^T v^0 \qquad \text{Eqn. (LIX)}$$

Since $\theta$ and $\tau$ are both sparse matrices that may be stored and transposed, $\theta^T \hat{p}_m$ and $\tau^T v^1$ may be readily computed. Most of block matrices in the propagator matrix W are zero or identity matrices. Therefore, to compute $W^T v^m$, we only need to compute the actions of transposed nontrivial block matrices in W.

Example 11

Reconstruction Methods

By use of the proposed discretized imaging model and methods for implementing H and $H^T$, a wide variety of iterative image reconstruction methods may be employed for determining estimates of $p_0$. In this work, we utilized a method that sought solutions of the optimization problem:

$$\hat{p}_0 = \underset{p_0 \geq 0}{\operatorname{argmin}} \|\hat{p} - H p_0\|^2 + \lambda |p_0|_{TV} \qquad \text{Eqn. (LX)}$$

where $\lambda$ is the regularization parameter, and a non-negativity constraint was employed. For the 3-D case, the TV-norm is defined as:

$$|p_0|_{TV} = \qquad \text{Eqn. (LXI)}$$

$$\sum_{n=1}^{N} \left\{ ([p_0]_n - [p_0]_{n_1-})^2 + ([p_0]_n - [p_0]_{n_2-})^2 + ([p_0]_n - [p_0]_{n_3-})^2 \right\}^{\frac{1}{2}}$$

where $[p_0]_n$ denotes the nth grid node, and $[p_0]_{n_1}$, $[p_0]_{n_2}$, $[p_0]_{n_3-}$ are neighboring nodes before the nth node along the first, second and third dimension, respectively. The fast iterative shrinkagethresholding algorithm (FISTA) was employed to solve Eqn. (LXI). The regularization parameter was empirically selected to have a value of 0.001 and was fixed for all studies.

A TR image reconstruction method based on the k-space pseudospectral method was also utilized. The TR reconstruction method solves the discretized acoustic Eqns. (XXV)-(XXVII) backward in time subject to initial and boundary conditions. The parameters of the PML boundary condition were the same with the ones employed in the system matrix construction.

For both methods, images were reconstructed on a uniform grid of 512×512 pixels with a pitch of 0.2 mm for the 2-D simulation studies and on a 256×256×128 grid with a pitch of 0.4 mm for the 3-D studies. All simulations were computed in the MATLAB environment on a workstation that contained dual hexa-core Intel Xeon E5645 CPUs and a NVIDIA Tesla C2075 GPU. The GPU was equipped with 448 1.15 GHz CUDA Cores and 5 GB global memory. The Jacket toolbox was employed to perform the computation of Eqns. (XXV)-(XXVII) and (XLVII)-(XLIX) on the GPU.

Example 12

Computer-Simulation Studies of 2-D PACT

Scanning Geometries:

Three different 2-D scanning geometries were considered to investigate the robustness of the reconstruction methods to different types and degrees of data incompleteness. A "full-view" scanning geometry utilized 180 transducers that were evenly distributed on a circle of radius 40 mm. A "full-view" scanning geometry utilized 60 transducers that were equally distributed on the circle. Finally, a "limited-view" scanning geometry utilized 90 transducers that were evenly located on a semi-circle of radius 40 mm.

Figure 12:
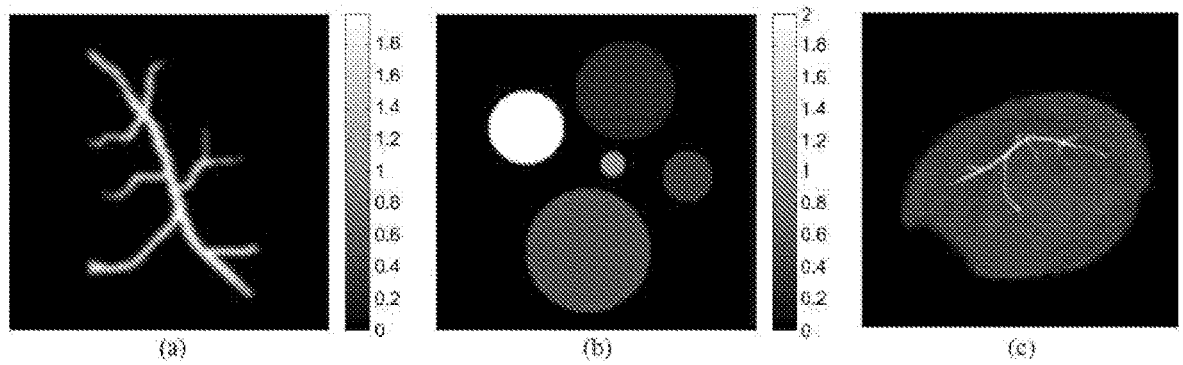
FIG. 12 is a blood vessel (FIG. 12A), disc numerical phantoms (FIG. 12B), and the overlapped image with a 3-D vessel phantom and skull to show the relative position of the phantom to the skull (FIG. 12C).

Numerical Phantoms:

The two numerical phantoms shown in FIGS. 12A and 12B were chosen to represent the initial pressure distributions in the 2-D computer-simulation studies. The blood vessel phantom shown in FIG. 12A was employed to investigate the robustness of the reconstruction methods with respect to different types and degrees of data incompleteness mentioned above. The low contrast disc phantom displayed in FIG. 12B was employed to investigate the robustness of the reconstruction methods with respect to errors in the SOS and density maps.

Measurement Data:

Assuming ideal point-like transducer and neglecting the transducer EIR and acoustic attenuation, simulated pressure data corresponding to the numerical phantoms were computed at the transducer locations by use of the k-space pseudospectral method for the three measurement geometries. To avoid committing an "inverse crime", a 1024× 1024 grid with a pitch of 0.1 mm was employed in this computation. A total of 20 000 temporal samples were computed at each transducer location with time step $\Delta t=30$ ns, all of which were employed by the TR image reconstruction method. However, only the first 1500 temporal samples were employed by the iterative reconstruction method. The same procedure was repeated for noisy pressure data, where 3% (with respect to maximum value of noiseless data) additive white Gaussian noise (AWGN) was added to the simulated pressure data.

Figure 13:
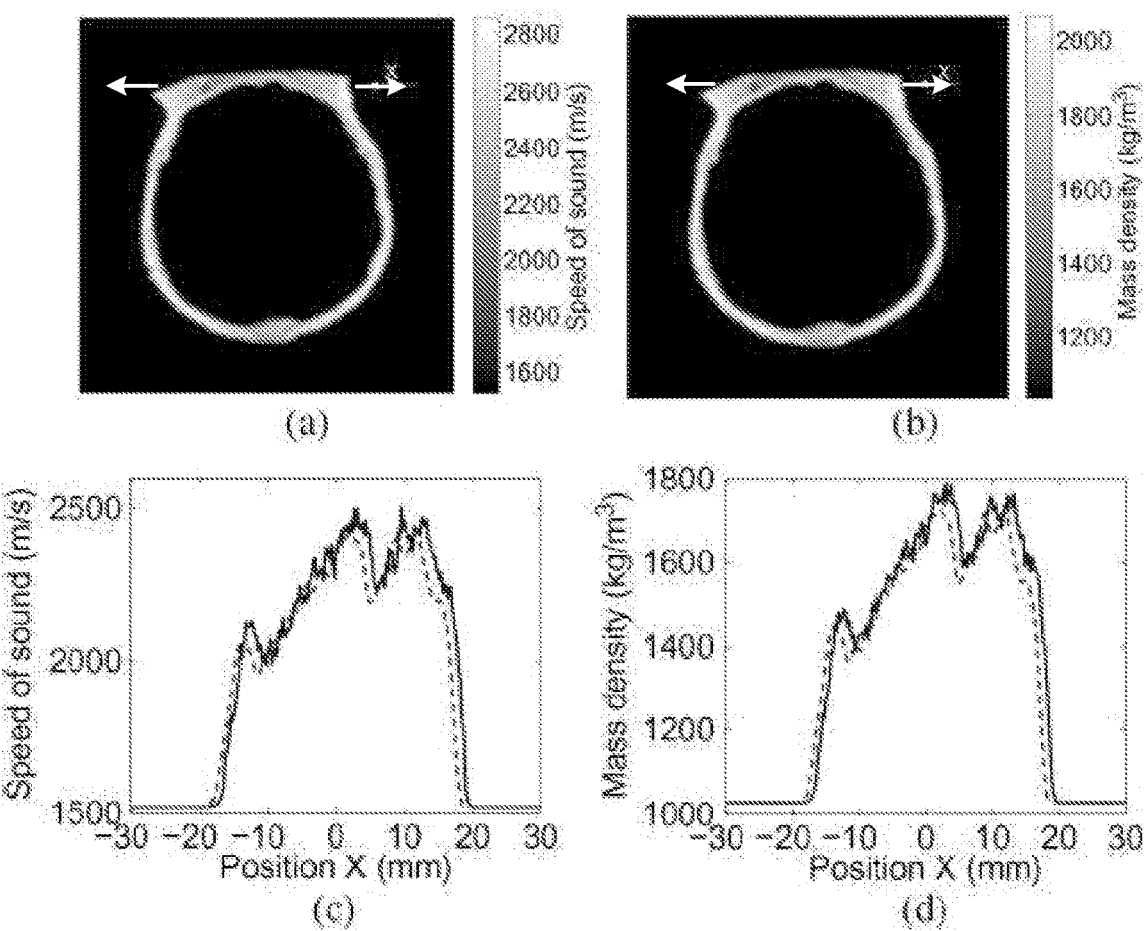
FIG. 13A is a slice of the speed of sound (SOS) map and FIG. 13B is a slice of the density map derived from the X-ray CT data of a monkey skull.
FIGS. 13C and 13D display profiles of the SOS and density maps along the x-axis indicated on FIGS. 13A and 13B, respectively.

Investigation of Systematic Errors:

The SOS and density maps employed in the simulation studies were representative of a monkey skull. The dimensions of the skull were approximately 7 cm×6 cm, and its thickness ranges from 2 to 4 mm. FIGS. 13A and 13B shows a transverse slice of the SOS and density maps, which were used in the 2-D simulations.

Since errors in the estimated SOS and density maps are inevitable regardless in how they are determined, the robustness of the reconstruction methods was investigated with respect to the SOS and density map errors, which were generated in two steps. First, 1.3% (with respect to maximum value) uncorrelated Gaussian noise with mean value of 1.7% of the maximum value was added to the SOS and density maps to simulate inaccuracy of the SOS and density values. Subsequently, the maps were shifted by 7 pixels (1.4 mm) to simulate a registration error. FIGS. 13C and 13D show profiles of the SOS and density maps with those errors along the "X"-axis indicated by the arrows in FIGS. 13A and 13B, respectively.

Example 13

Computer-Simulation Studies of 3-D PACT

Because PACT is inherently a 3-D method, we also conducted 3-D simulation studies to evaluate and compare the iterative reconstruction method and the TR method. As in the 2-D studies described above, the 3-D SOS and density maps were representative of a monkey skull. A 3-D blood vessel phantom was positioned underneath the skull to mimic the blood vessels on the cortex surface. To demonstrate this configuration, FIG. 12C shows the overlapped images of the 3-D phantom and the skull. The assumed scanning geometry was a hemispherical cap with radius of 46 mm, and 484 transducers were evenly distributed on the hemispherical cap by use of the golden section spiral method. The pressure data were computed on a 512×512× 256 grid with a pitch of 0.2 mm and a time step $\Delta t=30$ ns. The simulated pressure data were then contaminated with 3% AWGN. The TR reconstruction method employed 2000 temporal samples at each transducer location, whereas the iterative method employed 1000 samples.

Example 14

Studies Utilizing Experimental Data

Figure 14:
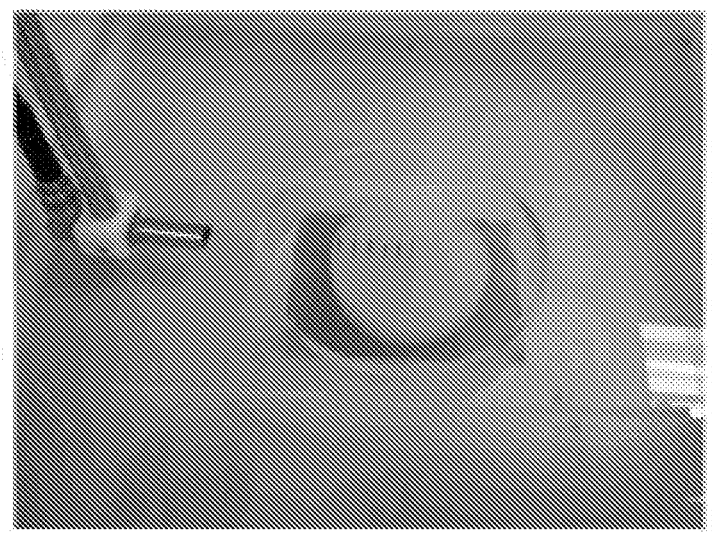
FIG. 14 is a photograph of a calibration body consisting of pencil leads held fixed within an agar matrix and surrounded by a removable cylindrical acrylic shell.
Figure 15:
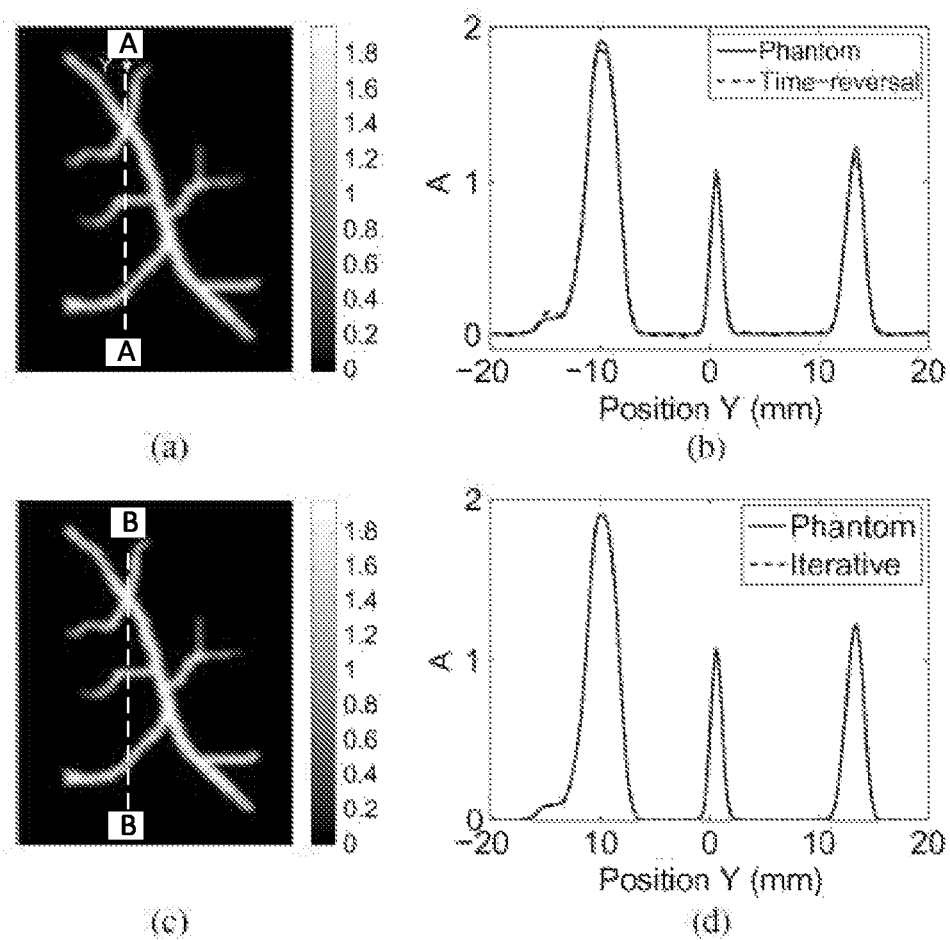
FIGS. 15A and 15C are PA images reconstructed from simulated noiseless data corresponding to full-view scanning geometry using a time-reversal and an iterative reconstruction method, respectively.
FIGS. 15B and 15D are the image profiles corresponding to line A-A on FIG. 15A and line B-B on FIG. 15C, respectively.
Figure 16:
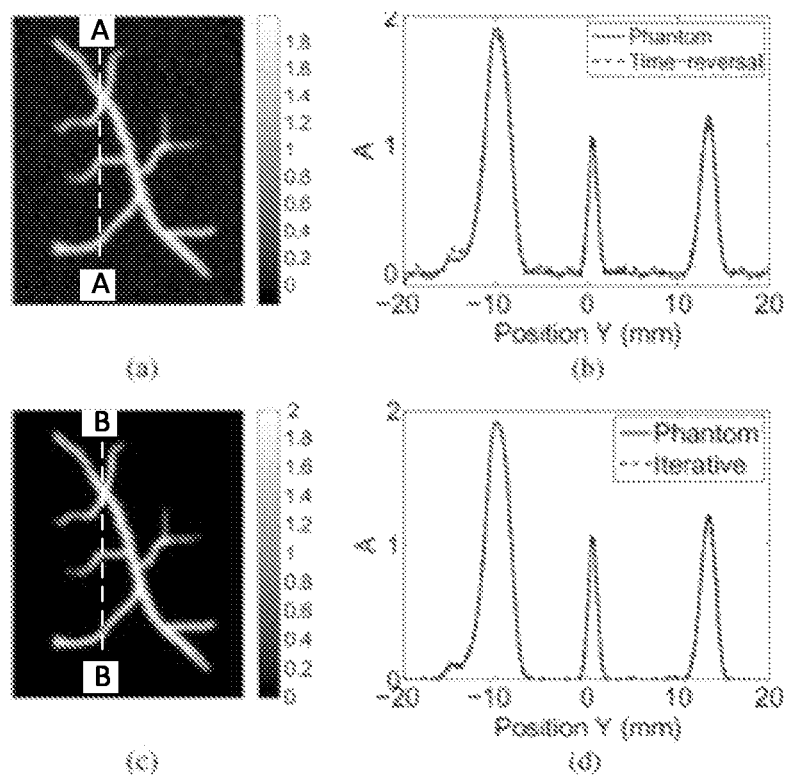
FIGS. 16A and 16C are PA images reconstructed from simulated noisy pressure data with 3% AWGN corresponding to full-view scanning geometry using a time-reversal and an iterative reconstruction method, respectively.
FIGS. 16B and 16D are the image profiles corresponding to line A-A on FIG. 16A and line B-B on FIG. 16C, respectively.
Figure 17:
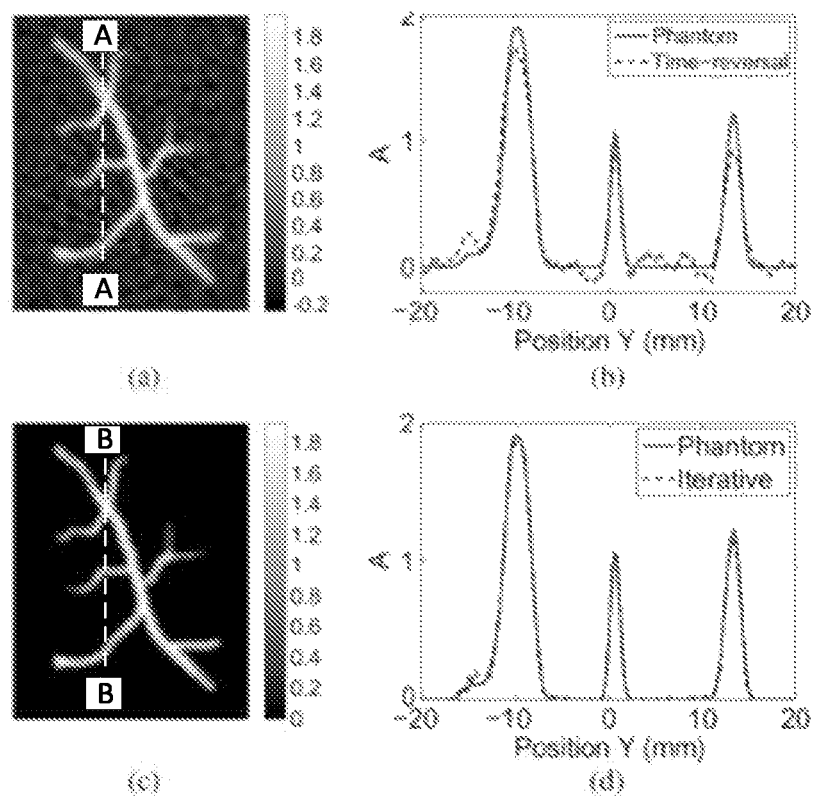
FIGS. 17A and 17C are PA images reconstructed from simulated noisy pressure data with 3% AWGN corresponding to few-view scanning geometry using a time-reversal and an iterative reconstruction method, respectively.
FIGS. 17B and 17D are the image profiles corresponding to line A-A on FIG. 17A and line B-B on FIG. 17C, respectively.
Figure 18:
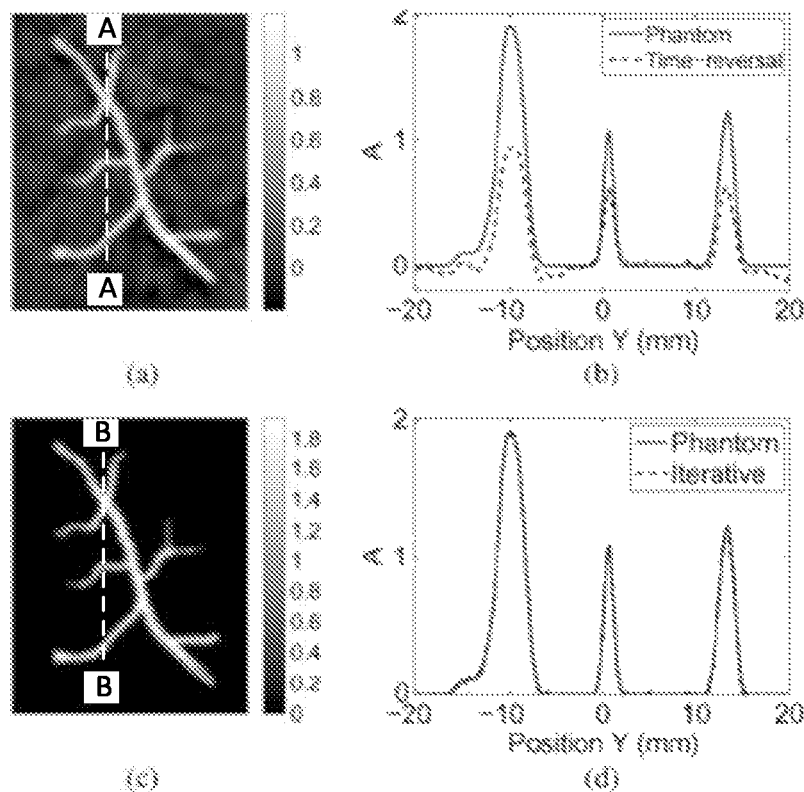
FIGS. 18A and 18C are PA images reconstructed from simulated noisy pressure data with 3% AWGN corresponding to limited-view scanning geometry using a time-reversal and an iterative reconstruction method, respectively.
FIGS. 18B and 18D are the image profiles corresponding to line A-A on FIG. 18A and line B-B on FIG. 18C, respectively.

Since the acoustic absorption and dispersion were modeled by the system matrix, the iterative method may naturally compensate for absorption and dispersion effects during reconstruction. To demonstrate the compensation for those effects, images were reconstructed by use of the iterative method with experimental data obtained from a well-characterized phantom object that is displayed in FIG. 14. The phantom contained six optically absorbing structures (pencil leads with diameter 1 mm) embedded in agar. These structures were surrounded by an acrylic cylinder, which represents the acoustic heterogeneities and absorption in the experiments. The cylinder had inner and outer radii of 7.1 and 7.6 cm, respectively, and a height of 3 cm. The density and SOS of the acrylic were measured and found to be 1200 kg·m$^{-3}$ and 3100 m·s$^{-1}$, and the estimated acoustic absorption parameters were found to be $\alpha_0=1.3$ dB MHz$^{-y}$·cm$^{-1}$ and y=0.9. These values were assigned to the annular region occupied by the acrylic in the 2-D SOS maps $c_0(r)$, density map $\rho_0(r)$ and attenuation coefficient $\alpha_0(r)$, respectively. The SOS value 1480 m·s$^{-1}$ and density value 1000 kg·m$^{-3}$ of water were assigned elsewhere. Since we neglected the relatively weak acoustic attenuation due to the water bath and agar, $\alpha_0(r)$ was also set to zero elsewhere.

The experimental data were acquired from a cylindrically focused ultrasound transducer that had a central frequency of 2.25 MHz with a bandwidth of 70%. The transducer was scanned along a circular trajectory of radius 95 mm, and 20 000 temporal samples were measured at each transducer location at a sampling rate of 20 MHz. Images were reconstructed by use of PA signals recorded at 200, 100 (over) 180°, and 50 transducer locations, which correspond to the full-view, limited-view, and few-view scanning geometry, respectively. The TR reconstruction method employed 20 000 temporal samples at each transducer location, while the iterative method employed 2000 samples. The reference images were also reconstructed by use of the data obtained at 200 transducer locations when the acrylic cylinder was absent. Since the pencil lead phantom is expected to generate quasi-cylindrical waves and the morphology of the acoustic heterogeneity (the acrylic shell) was a cylinder, the cylindrical wave propagation may be approximated by the 2-D PA wave equation. Accordingly, a 2-D imaging model was used, and all the reconstructions were performed on a grid of 512×512 pixels with a pitch of 0.5 mm. The effects of shear wave propagation in the acrylic cylinder were neglected, which were expected to be of second-order importance compared to wavefield perturbations that arise from inhomogeneities in the SOS and density distributions.

Example 15

Computer-Simulations Corresponding to Different Scanning Geometries

The reconstructed images corresponding to the three scanning geometries are displayed in FIGS. 15-18. In each figure, the results in the top row correspond to use of the TR reconstruction method, while the bottom row shows the corresponding results obtained by use of the iterative method. The profiles shown in each figure are along the "Y"-axis indicated by the arrow in FIG. 15A. The red solid lines and blue dashed lines correspond to profiles through the phantom and reconstructed images, respectively. With the full-view scanning geometry, the TR method and the iterative method both produce accurate reconstructed images. However, with the few-view and the limited-view scanning geometries, the images reconstructed from the iterative method contain fewer artifacts and less noise than the TR results. Also, the values of the images reconstructed from the iterative method are much closer to the values of the phantom than those produced by the TR method. The root mean square error (RMSE) between the phantom and the reconstructed images were also computed. The RMSE of images reconstructed by use of the TR method and the iterative method corresponding to noisy pressure data with the full-view, few-view, and limited view scanning geometries are 0.011, 0.042, 0.081 and 0.003, 0.007, 0.008, respectively. The computational time of the TR method was 1.7 min, while the iterative method took approximately 10 min to finish 20 iterations.

Example 16

Simulation Results with Errors in SOS and Density Maps

Figure 19:
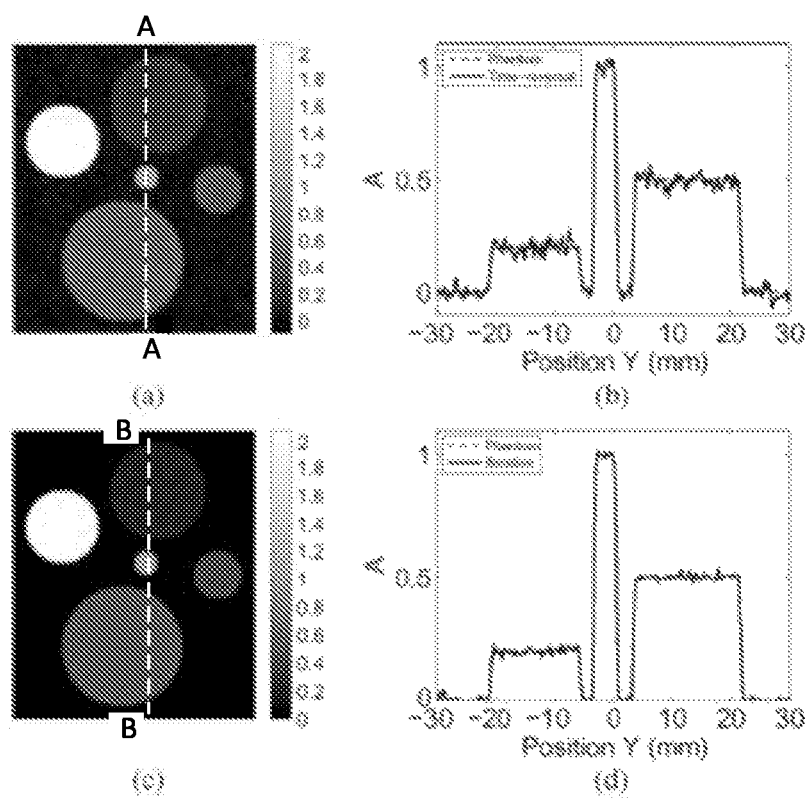
FIGS. 19A and 19C are PA images reconstructed from simulated noisy pressure data with 3% AWGN and actual SOS and density maps using a time-reversal and an iterative reconstruction method, respectively.
FIGS. 19B and 19D are the image profiles corresponding to line A-A on FIG. 19A and line B-B on FIG. 19C, respectively.

FIG. 19 shows the images reconstructed from noisy pressure data corresponding to the low contrast disc phantom in the case where SOS and density maps have no error. The results corresponding to TR and iterative image reconstruction methods are shown in the top and bottom row, respectively. The RMSE corresponding to the time-reversal and the iterative results are 0.026 and 0.007, respectively. These results suggest that the iterative method may more effectively reduce the noise level in the reconstructed images than the time-reversal method.

Figure 20:
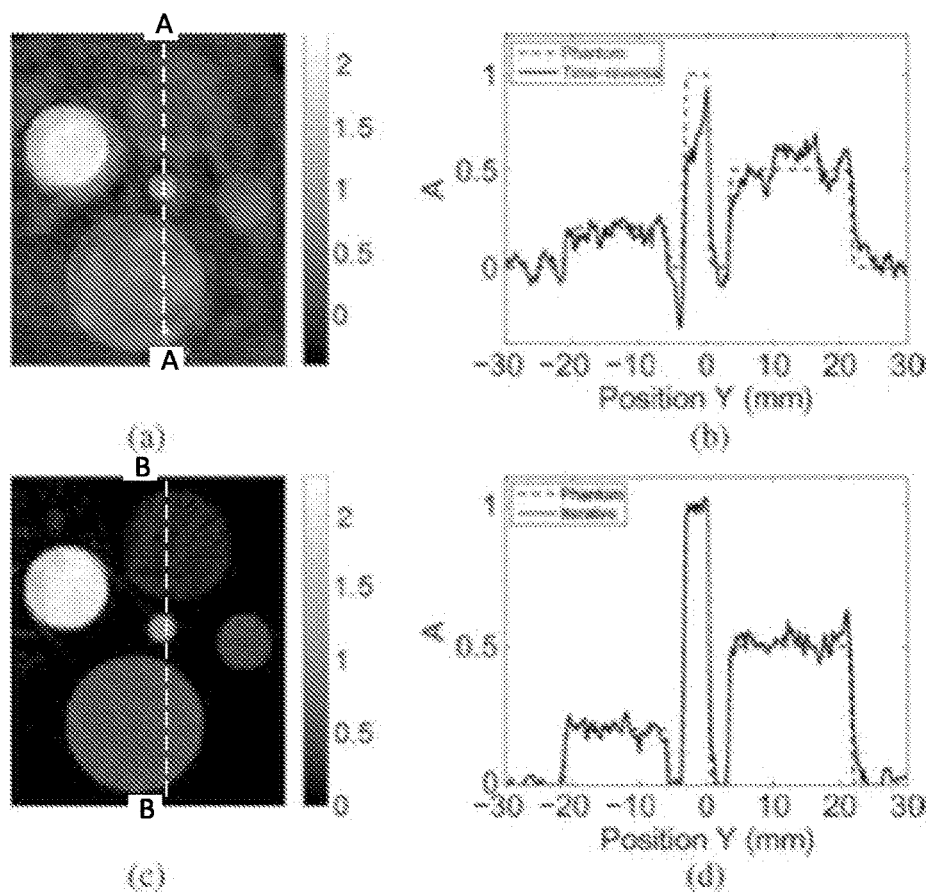
FIGS. 20A and 20C are PA images reconstructed from simulated noisy pressure data with 3% AWGN and SOS and density maps with errors using a time-reversal and an iterative reconstruction method, respectively.
FIGS. 20B and 20D are the image profiles corresponding to line A-A on FIG. 20A and line B-B on FIG. 20C, respectively.

The images reconstructed by use of the SOS and density maps with errors are shown in FIG. 20. The image produced by the iterative method has cleaner background than the TR result, and the RMSE corresponding to the TR and the iterative results are 0.086 and 0.034, respectively. The boundaries of the disc phantoms also appear sharper in the image reconstructed by the iterative method as compared to the TR result. This may be attributed to the TV regularization employed in the iterative method. These results suggest that appropriately regularized iterative reconstruction methods may be more robust to the errors in the SOS and density maps than the TR method.

Example 17

3-D Simulation

Figure 21:
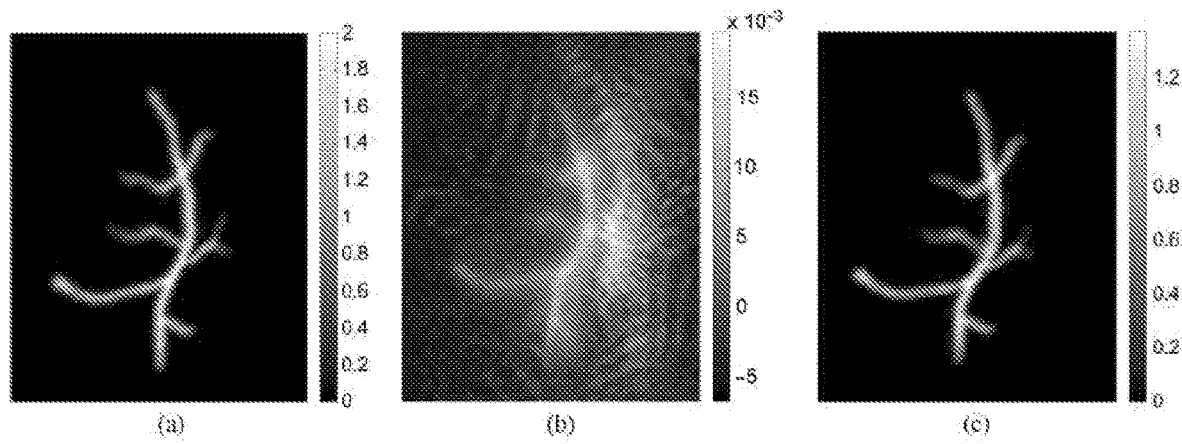
FIG. 21A is a maximum intensity projection rendering of a 3-D phantom vessel.
FIG. 21B is a 3-D PA image of the phantom vessel reconstructed using a time-reversal reconstruction method.
FIG. 21C is a 3-D PA image of the phantom vessel reconstructed using an iterative reconstruction method.

The 3-D blood vessel phantom and the reconstructed images were visualized by the maximum intensity projection (MIP) method. FIG. 21A shows the phantom image, and FIGS. 21B and 21C display the images reconstructed by use of the TR method and the iterative method, respectively. They are all displayed in the same grey scale window. The RMSE corresponding to the TR and the iterative results are 0.018 and 0.003, respectively. These results suggest that the iterative method is robust to the data incompleteness and the noise in the pressure data. The computational time of the TR method was approximately 6 min, while the iterative method with 10 iterations required 110 min.

Example 18

Experimental Results

Figure 22:
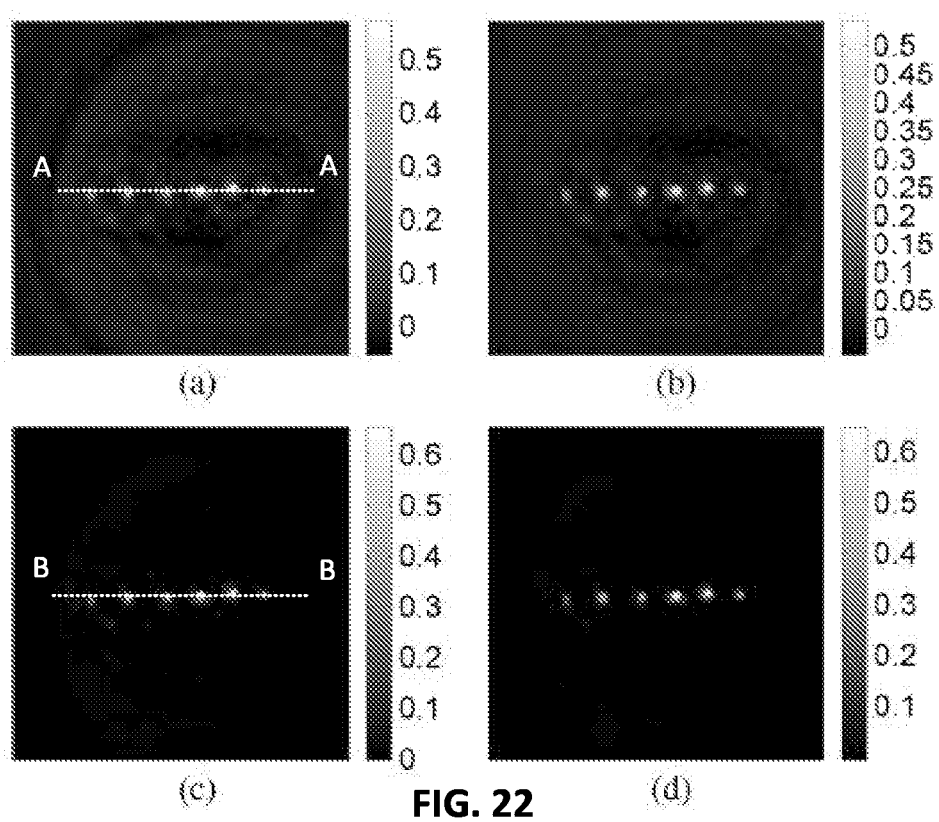
FIGS. 22A and 22B are PA images of the calibration body of FIG. 14 reconstructed with PA data from 200 view angles over a 360° range using a time-reversal reconstruction method from data from 200 views with the acrylic shell absent and present, respectively.
FIGS. 22C and 22D are PA images of the calibration body of FIG. 14 reconstructed with PA data from 200 view angles over a 360° range using an iterative reconstruction method with the acrylic shell absent and present, respectively.
Figure 23:
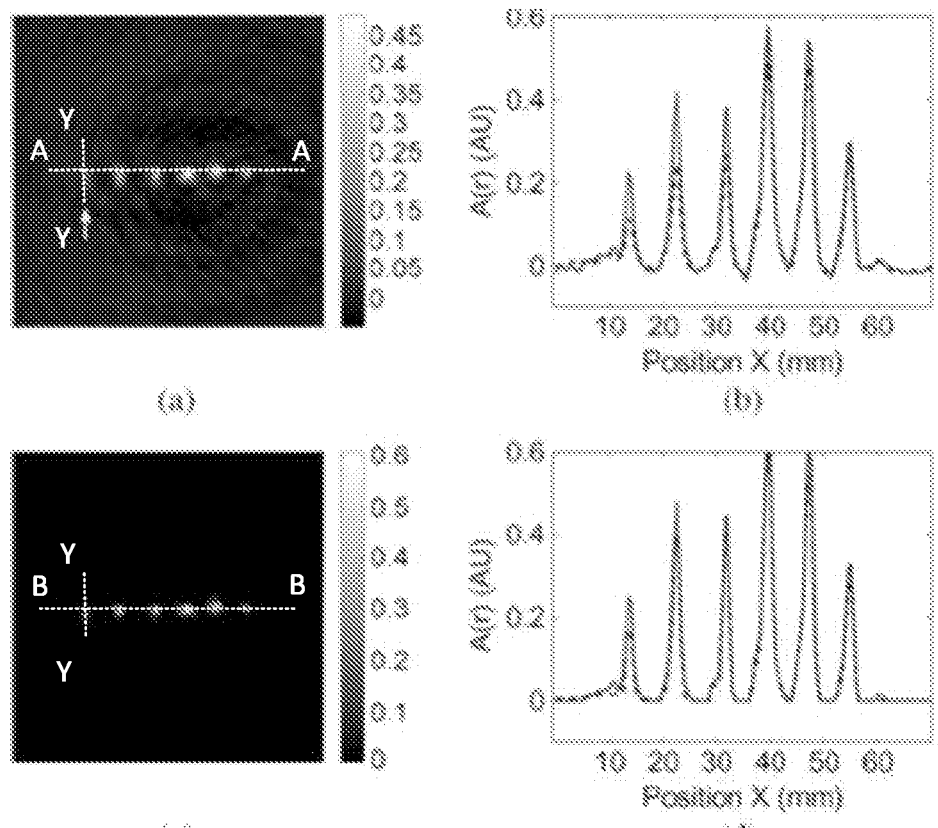
FIGS. 23A and 23C are PA images of the calibration body with acrylic shell of FIG. 14 reconstructed with PA data from 50 view angles over a 360° range using a time-reversal reconstruction method and an iterative reconstruction method, respectively.
FIG. 23B is a graph comparing image profiles taken along sector line A-A of FIG. 22A (solid line) and FIG. 23A (dashed line).
FIG. 23D is a graph comparing image profiles taken along sector line A-A of FIG. 22C (solid line) and FIG. 23C (dashed line).
Figure 24:
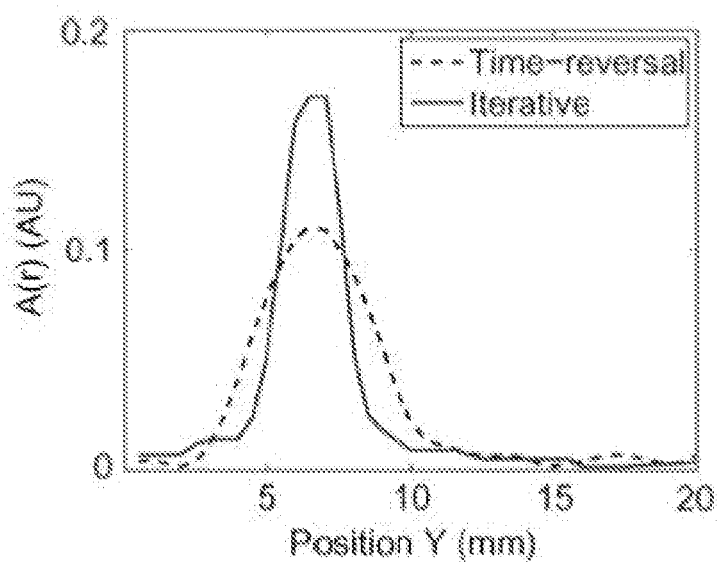
FIG. 24 compares the image profiles of the reconstructed images of FIG. 23A (dashed line) and FIG. 23C (solid line) taken along sector line Y-Y.
Figure 25:
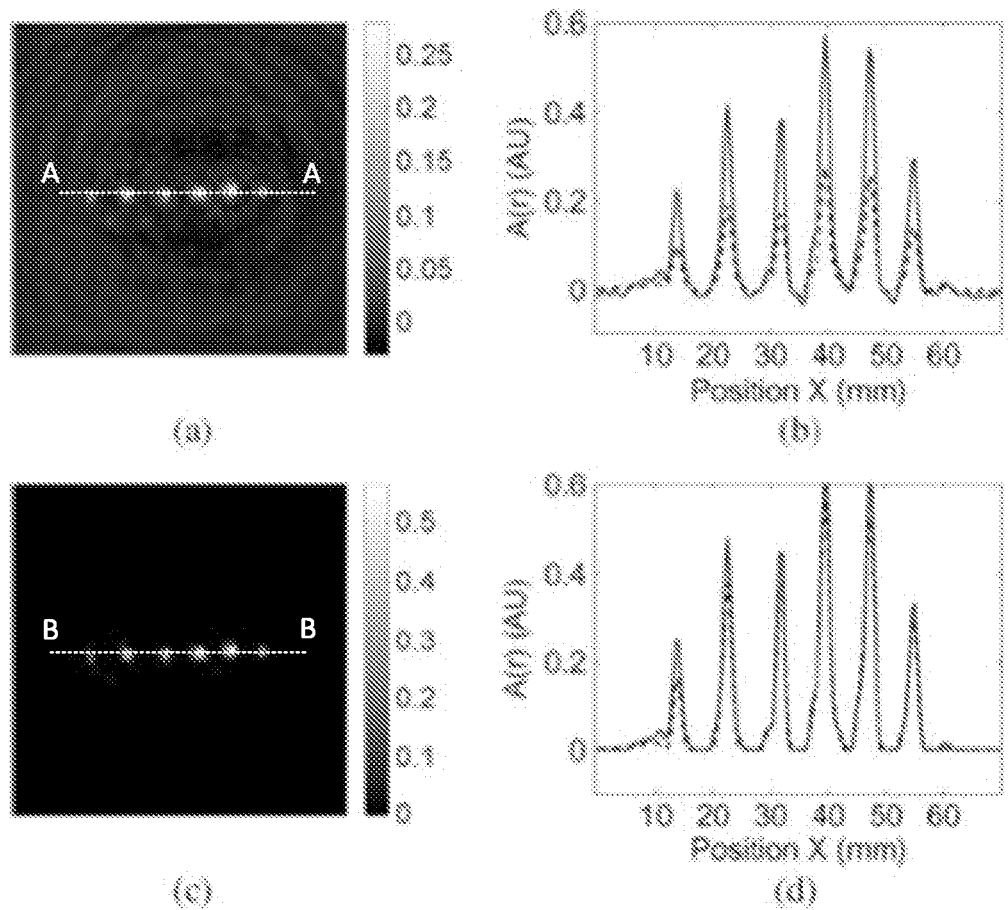
FIGS. 25A and 25C are PA images of the calibration body with acrylic shell of FIG. 14 reconstructed with PA data from 100 view angles over a 180° range view angles over a 360° range using a time-reversal reconstruction method and an iterative reconstruction method, respectively.
FIG. 25B is a graph comparing image profiles taken along sector line A-A of FIG. 22A (solid line) and FIG. 25A (dashed line).
FIG. 25D is a graph comparing image profiles taken along sector line A-A of FIG. 22C (solid line) and FIG. 25C (dashed line).

The images reconstructed from the experimental data are shown in FIGS. 22-25. FIG. 22 shows the image reconstructed with the full-view scanning geometry by use of the TR method (top row) and the iterative method (bottom row). FIGS. 22A and 22C display the reference images produced by each of the methods when the acrylic shell was absent. FIGS. 22B and 22E show the reconstructed images for the case when the acrylic shell was present. The RMSE between FIGS. 22B and 22D and the reference images FIGS. 22A and 22C are 0.003 and 0.002, respectively. FIGS. 23A and 23C shows the images reconstructed with the few-view scanning geometry when the acrylic shell was present. The corresponding image profiles are displayed in FIGS. 23B and 23D. The profiles of FIGS. 23A and 23C along the "Y"-axis were shown in FIG. 24, which shows that the iterative method produced higher resolution images than the TR method. This may be attributed to the TV regularization that mitigates model errors that arise, for example, by neglecting the shear wave and finite transducer aperture effects. The RMSE between FIGS. 23B and 23D and their reference images are 0.005 and 0.002, respectively. FIG. 25 displays the images reconstructed with the limited-view scanning geometry when the acrylic shell was present. The RMSE between FIGS. 25A and 25C and their reference images are 0.007 and 0.003, respectively. These results show that the iterative method may effectively compensate for the acoustic attenuation and mitigate artifacts and distortions due to incomplete measurement data.

Example 19

Modeling Transducer Impulse Responses

An important feature of the proposed discretized PACT imaging model is that the transducer's impulse responses, including the spatial impulse response (SIR) and the acousto-electrical impulse response (EIR), may be readily incorporated into the system matrix.

The SIR accounts for the averaging effect over the transducer surface, which may be described as:

$$\hat{p}^{SIR}(r_l^d, m\Delta t) = \frac{\int_{S(r_l^d)} dS(r_t') p(r_t', m\Delta t)}{S(r_l^d)} \qquad \text{Eqn. (LXII)}$$

where $\hat{p}_{SIR}(r_l^d, m\Delta t)$ is the averaged pressure at time $t=m\Delta t$ over the surface of the ith transducer, $S(r_l^d)$ is the surface area of the lth transducer centered at $r_l^d$.

In order to incorporate the SIR into the system matrix, the transducer surface may be divided into small patches with equal area that is much less than the acoustic wavelength, so the integral in (45) may be approximated by:

$$\hat{p}^{SIR}(r_l^d, m\Delta t) \approx \gamma^{SIR} \hat{p}_m^l \qquad \text{Eqn. (LXIII)}$$

where $\hat{p}_m^l = (p(r_l^1, m\Delta t), \ldots, p(r_l^K, m\Delta t))^T$ denotes the acoustic pressure at patches of lth transducer at time $m\Delta t$. Here for simplicity, all the transducers are assumed to be divided into K patches with equal area $\Delta S$, and it is readily to extend to general cases where lth transducer is divided into $K_l$ patches with area of $\Delta S_{lk}$.

Recalling the measured pressure data $\hat{p}_m$ and $\hat{p}$ defined for point-like transducer, we may redefine $\hat{p}_m$ as a KL×1 vector that represents the acoustic pressure at patches of transducers with finite area at time $t=m\Delta t$ as:

$$\hat{p}_m \equiv \begin{bmatrix} \hat{p}_m^1 \\ \vdots \\ \hat{p}_m^L \end{bmatrix} \quad \text{Eqn. (LXIV)}$$

The corresponding $\hat{p}$ may be redefined as a KLM×1 vector denoting the measured pressure data corresponding to all transducer and temporal samples as:

$$\hat{p} \equiv \begin{bmatrix} \hat{p}_0 \\ \vdots \\ \hat{p}_{M-1} \end{bmatrix} \quad \text{Eqn. (LXV)}$$

The averaged pressure measured by all transducer and temporal samples may be defined as the LM×1 vector:

$$\hat{p}^{SIR} \equiv \begin{bmatrix} \hat{p}_0^{SIR} \\ \vdots \\ \hat{p}_{M-1}^{SIR} \end{bmatrix} \quad \text{Eqn. (LXVI)}$$

where the L×1 vector is $$\hat{p}_m^{SIR} \equiv \begin{bmatrix} \hat{p}^{SIR}(r_1^d, m\Delta t) \\ \vdots \\ \hat{p}^{SIR}(r_L^d, m\Delta t) \end{bmatrix} \quad \text{Eqn. (LXVII)}$$

$\hat{p}$ and $\hat{p}^{SIR}$ and may be related as:

$$\hat{p}^{SIR} = \Gamma^{SIR}\hat{p} \quad \text{Eqn. (LXVIII)}$$

where the KLM×LM matrix is:

$$\Gamma^{SIR} \equiv \begin{bmatrix} \gamma^{SIR} & 0_{1\times K} & \cdots & 0_{1\times K} \\ 0_{1\times K} & \gamma^{SIR} & \cdots & 0_{1\times K} \\ \vdots & \vdots & \ddots & \vdots \\ 0_{1\times K} & 0_{1\times K} & \cdots & \gamma^{SIR} \end{bmatrix} \quad \text{Eqn. (LXIX)}$$

The EIR models the electrical response of the piezoelectric transducer. With the assumption that the transducer is a linear shift invariant system with respect to the input averaged pressure time sequence, the output voltage signal is the convolution result of the input and the EIR.

For simplicity, the transducers are assumed to process identical EIR, and let $h^e = (h_1^e, \ldots, h_J^e)^T$ be the discrete samples of the EIR. The input averaged pressure time sequence of the lth transducer may be defined as an L×1 vector $\hat{p}_{SIR}^l \equiv (\hat{p}^{SIR}(r_l^d, 0), \ldots, \hat{p}^{SIR}(r_l^d, (M-1)\Delta t))^T$. Then the output voltage signal $\hat{p}_l^{IR}$ of the lth transducer may be expressed as a (J+M−1)×1 vector:

$$\hat{p}_l^{IR} = h^e * \hat{p}_{SIR}^l \quad \text{Eqn. (LXX)}$$

where denotes discrete linear convolution operation, which may be constructed as a matrix multiplication by converting one of the operands into the corresponding Toeplitz matrix.

The output voltage signals of all transducers may then be computed as:

$$\hat{p}^{IR} = \Gamma^{EIR}\hat{p}^{SIR} \quad \text{Eqn. (LXXI)}$$

where the L(J+M−1)×LM matrix $$\Gamma^{EIR} \equiv \begin{bmatrix} \gamma^{EIR} \\ \vdots \\ \gamma^{EIR} \end{bmatrix} \quad \text{Eqn. (LXXII)}$$

and $\gamma^{EIR}$ is a (J+M−1)×LM Toeplitz-like matrix defined as:

$$\gamma^{EIR} \equiv \begin{bmatrix} h_1^e & 0_{1\times(L-1)} & 0 & \cdots & 0 & 0_{1\times(L-1)} & 0 \\ \vdots & \vdots & h_1^e & \vdots & \vdots & \vdots & \vdots \\ h_J^e & \vdots & \vdots & \vdots & 0 & 0_{1\times(L-1)} & 0 \\ 0 & 0_{1\times(L-1)} & h_J^e & \cdots & h_1^e & 0_{1\times(L-1)} & 0 \\ 0 & 0_{1\times(L-1)} & 0 & \cdots & \vdots & \vdots & h_1^e \\ \vdots & \vdots & \vdots & \vdots & h_J^e & \vdots & \vdots \\ 0 & 0_{1\times(L-1)} & 0 & \cdots & 0 & 0_{1\times(L-1)} & h_J^e \end{bmatrix} \quad \text{Eqn. (LXXIII)}$$

It is then found that $$\hat{p}^{IR} = \Gamma^{EIR}\Gamma^{SIR}ST_{M-1}\cdots T_1 T_0 p_0 \quad \text{Eqn. (LXXIV)}$$

and the corresponding system matrix that incorporates the transducer impulse responses is found to be:

$$H^{IR} = \Gamma^{EIR}\Gamma^{SIR}ST_{M-1}\cdots T_1 T_0 \quad \text{Eqn. (LXXV)}$$

Example 20

Imaging of a Graphite Phantom Through a Human Skull

A graphite phantom and the cerebral cortex of a canine brain were successfully imaged through the skull in the differential images. The photon recycling device was positioned on top of human skull to recycle the light scattered off of the skull. The light beam propagated through the central hole of the photon recycling device, and then was expanded by passing through a plano-concave lens (12.7 mm aperture, 0.42 NA) and a bi-concave lens (12.7 mm aperture, 0.5 NA) to illuminate the skull. The illumination source was a laser operating at 1064 nm wavelength (Vibrant HE 315I, Opotek, Inc., CA). The laser pulse had a repetition rate of 10 Hz and a pulse width of 5 ns. The fluence of each laser pulse on the top skull surface was well below 40 mJ/cm$^2$ The intact human skull was purchased (Skull Unlimited International Inc. Oklahoma City, Okla.) and was donated by an 83-year-old Caucasian male. The natural skull was fixed with the aid of dermestid carrion beetles. The skull was subsequently cleaned by use of hydrogen peroxide and a degreaser. The length, width, and height of the fixed skull were 22 cm, 15 cm and 15 cm, respectively. We expanded the foramen magnum to place samples inside the skull. The thickness of the skull is inhomogeneous, ranging from ~7 mm temporal area) to ~11 mm (frontal area). The measured light transmittance through a fixed human skull was reported to be similar to previously computed light transmittance of a fresh skull. Also the effects of fixation on the acoustic properties of skull have been demonstrated to be minor. Because of this, fixed skulls have long been used for transcranial ultrasound research. Therefore, a fixed skull may be employed as a study model for transcranial PAT.

A 1-MHz spherically focused transducer (V314, Panametrics, Olympus) circularly scanned the skull to receive PA signals at 200 positions. The received PA signals were amplified by a 50-dB amplifier (5072 PR, Panametrics, Waltham, Mass.), then directed to a data-acquisition (DAQ) card (CS 14200; Gage Applied, Lockport, Ill.). The DAQ card was simultaneously triggered by the Q-switch signal from the laser to record the PA data in computer for back-projection reconstruction. To compensate the PA amplitude for laser fluence fluctuation, the laser pulses were sampled by a photodiode (SM05PD1A, Thorlabs).

Figure 27:
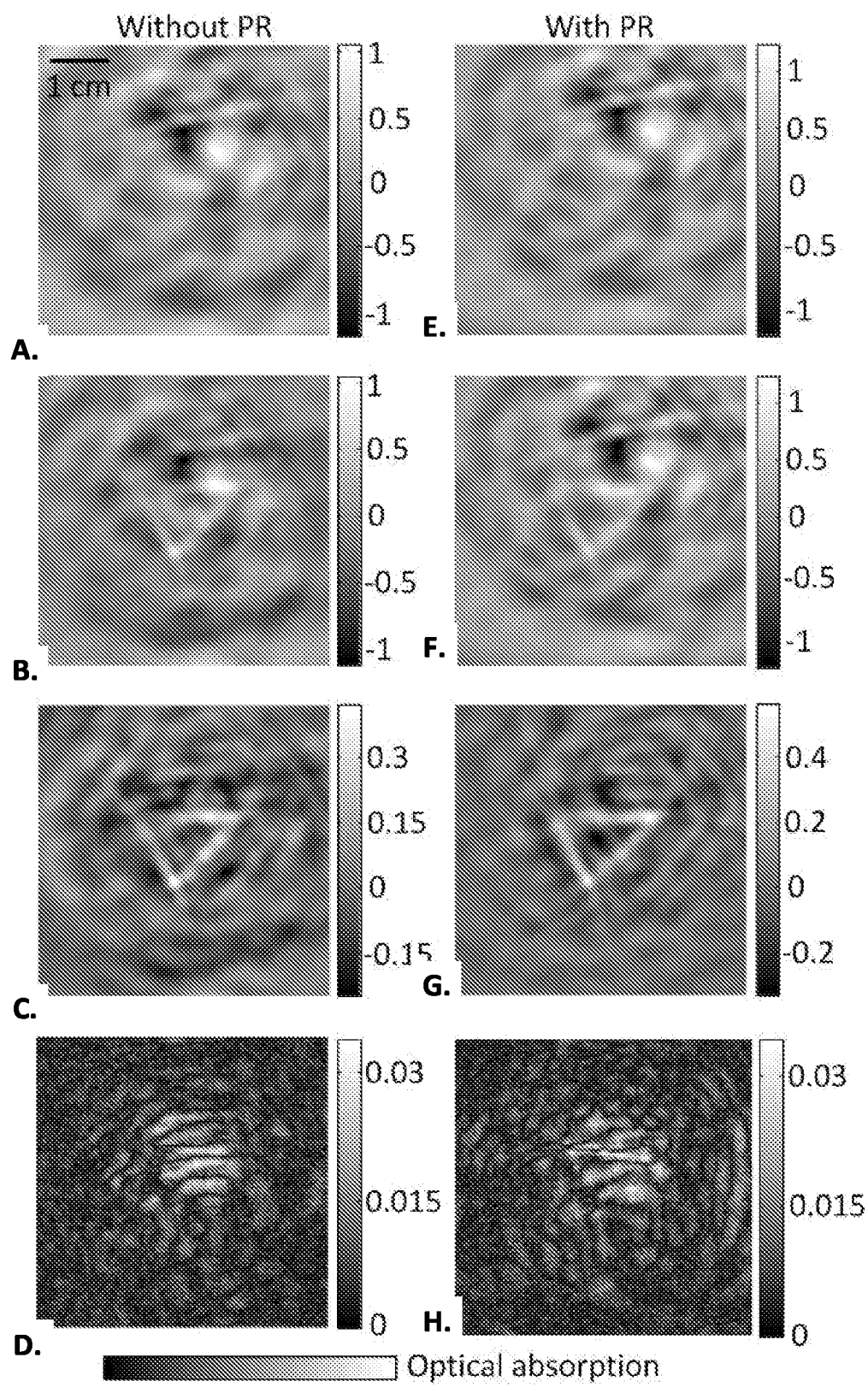

A triangular target composed of three graphite bars with a diameter of 0.7 mm was embedded in agar as the test phantom. Initially, the phantom was moved inside the empty skull, but out of the light illumination area for PAT with PR, as shown in FIG. 27A (skull only). Then the phantom was moved to the cortical area inside the skull without changing other experimental conditions, and the corresponding PAT image is shown in FIG. 27B. The PA signals in FIG. 27B are slightly greater than signals in FIG. 27A due to the absorption contribution of the graphite. The triangular shape may be found in FIG. 27B despite the strong background signals from the skull. The differential image in FIG. 27C [FIG. 27B subtracted by FIG. 27A] reveals the triangle more clearly with a high signal to background contrast than that in FIG. 27B. Each image was acquired five times to calculate the signal-to-noise ratio (SNR, defined as an amplitude ratio here), and the average images are shown. The standard deviation image of the five differential images is shown in FIG. 27D. The difference between the PAT images acquired without the photon recycling device (left column marked with 'Without PR') and with the photon recycling device (right column marked with 'With PR') is that the latter have stronger signals than the former while the noise in standard derivation did not change significantly. That is because diffusely reflected light from the skull was recycled back toward the skull by the photon recycling device to generate more PA signals. Based on the respective five differential images acquired with and without the photon recycling device, the SNR was found to be enhanced by the photon recycling device 2.4 times from 6.3 to 15.

Example 21

Imaging of a Canine Brain Through a Human Skull

Figure 28:
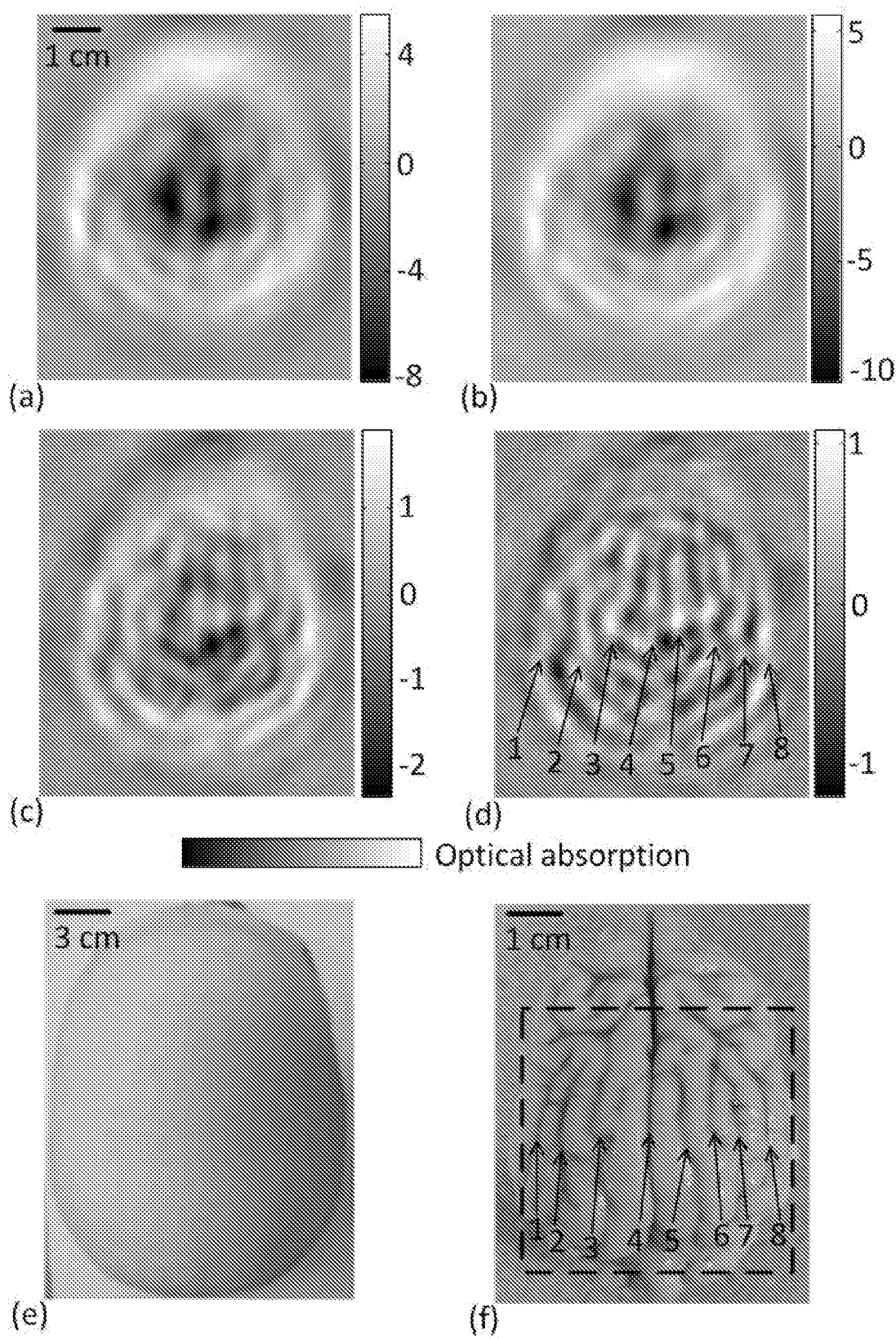
FIG. 28A is a PAT image of a human skull obtained using a photon recycling device.
FIG. 28B is a PAT image of a canine brain obtained through the whole adult human skull using a photon recycling device.
FIG. 28C is a differential image obtained from FIG. 28A and FIG. 28B.
FIG. 28D is a PAT image obtained by applying a high-pass filter to the image of FIG. 28C.
FIGS. 28E 28F are photographs of the human skull and canine brain, respectively that were imaged in FIGS. 28A-28B.

After craniotomy on a 3-month-old canine, the brain was obtained and immediately immersed in 10% formalin solution to maintain the vasculature. All procedures in the animal experiments followed the protocols approved by the Institutional Animal Care and Use Committee at Washington University in St. Louis. PAT imaging of the canine brain cortex through the human skull with the photon recycling device was conducted with the same procedure as employed in the aforementioned phantom experiment in Example 20. The PAT image with only the skull present is shown in FIG. 28A. After the canine brain cortex was positioned in the cortical area of the skull, a similarly distorted PAT image was obtained as displayed in FIG. 28B. However, the differential PAT image shown in FIG. 28C [FIG. 28A subtracted from FIG. 28B] reveals brain features that are readily identifiable. Since high-frequency signals were more attenuated by the thick skull [shown as a top-view photograph in FIG. 28E], the surviving PA signals were low-pass filtered. As a result, the reconstructed images possess a slowly varying background and a lack of sharp features as shown in FIG. 28C. After applying a high-pass filter on the image in FIG. 28C, many more features are clearly revealed as shown in FIG. 28D. The background was suppressed at the expense of reducing the peak signal amplitude about 1.8 times. Eight main blood vessels were marked by numbered arrows, which have good correlation with the features in the photograph of the canine brain in FIG. 28F.

What is claimed is:

1. A method of imaging a brain situated within a skull of a subject, comprising:
   obtaining an adjunct image dataset corresponding to the skull of the subject being imaged;
   analyzing the adjunct image dataset to specify one or more parameters of a spatial model of the skull;
   obtaining one or more photoacoustic imaging signals corresponding to the brain of the subject through the skull of the subject at a photoacoustic tomography (PAT) coordinate system, wherein obtaining the one or more photoacoustic imaging signals comprises directing, with at least one laser pulse, illumination of the skull of the subject, wherein a first fraction of the at least one laser pulse passes through the skull to illuminate the brain, wherein a second fraction of the at least one laser pulse reflects off a surface of the subject, wherein a photon recycling device reflects at least a portion of the second fraction of the at least one laser pulse back towards the brain as recycled laser light to further illuminate the brain, and wherein the one or more photoacoustic imaging signals include (a) acoustic signals generated by the brain of the subject in response to illumination by the first fraction of the at least one laser pulse and (b) acoustic signals generated by the brain of the subject in response to illumination of the brain by the recycled laser light from the photon recycling device;
   determining the PAT coordinate system using the one or more photoacoustic imaging signals;
   registering the spatial model to the PAT coordinate system to establish an imaging model; and
   reconstructing a photoacoustic image from the one or more photoacoustic imaging signals of the brain of the subject by implementing an image reconstruction method configured to mitigate aberrations of the one or more photoacoustic imaging signals induced by the skull of the subject using the imaging model and the one or more imaging photoacoustic signals.

2. The method of claim 1, wherein the adjunct image dataset is obtained using an X-ray computed tomography scanning device or a magnetic resonance imaging device.

3. The method of claim 2, wherein the adjunct image dataset comprises a spatial map of porosity and acoustic properties comprising a speed of sound and an ambient density.

4. The method of claim 3, wherein the image reconstruction method is chosen from a time-reversal reconstruction method and an iterative reconstruction method.

5. The method of claim 4, wherein the image reconstruction method is the time-reversal reconstruction method, and wherein the time-reversal reconstruction method comprises solving discretized forms of acoustic equations describing a propagation of an acoustic wavefield though a heterogeneous medium subject to one or more initial conditions corresponding to an initial photoacoustically generated wavefield within the medium and an initial acoustic particle velocity of zero throughout the medium to obtain the photoacoustic image corresponding to a spatial distribution of an initial acoustic wavefield, wherein the initial acoustic wavefield is proportional to an absorbed optical energy density.

6. The method of claim 5, wherein the discretized forms of the acoustic equations are solved using a numerical algorithm comprising one or more of a real-space finite-element method, a real-space finite-difference method, and a k-space pseudospectral method.

7. The method of claim 6, wherein the numerical algorithm is the k-space pseudospectral method.

8. The method of claim 4, wherein the image reconstruction method is the iterative reconstruction method comprising iteratively solving a discretized imaging model comprising a system matrix to obtain the photoacoustic image corresponding to a spatial distribution of an initial acoustic wavefield, wherein the initial acoustic wavefield is proportional to an absorbed optical energy density.

9. The method of claim 8, wherein the iterative reconstruction method solves the discretized imaging model using an optimization relation.

10. The method of claim 9, wherein the optimization relation is a total variation-regularized penalized least-squares cost function.

11. The method of claim 1, further comprising generating a second photoacoustic image and subjecting the photoacoustic image and the second photoacoustic image to a differential imaging method comprising subtracting the second photoacoustic image from the photoacoustic image to obtain a differential image.

12. The method of claim 11, wherein the differential image is subjected to a high-pass filter.

13. The method of claim 11, wherein the photoacoustic image corresponds to the brain and the skull of the subject at a first condition and the second photoacoustic image corresponds to the brain and the skull of the subject at a second condition.

14. The method of claim 13, wherein the first condition comprises an untreated baseline condition and the second condition comprises a condition after a treatment, wherein the treatment is chosen from: a change in an endogenous contrast agent, an introduction of an exogenous contrast agent, a therapeutic treatment, and a performance of a cognitive task.

15. The method of claim 1, wherein illuminating of the skull of the subject with the at least one laser pulse comprises directing the at least one laser pulse through a concave lens of the photon recycling device.

16. The method of claim 1, wherein reflecting at least the portion of the second fraction of the at least one laser pulse back towards the brain of the subject as recycled laser light comprises reflecting laser light off of a concave surface of the photon recycling device.

17. The method of claim 16, wherein the concave surface of the photon recycling device has an elliptical parabaloid curvature.

18. The method of claim 1, wherein the second fraction of the at least one laser pulse reflects off a surface of the skull of the subject.

19. The method of claim 1, wherein the image reconstruction method is configured to account for shear wave mode conversion.

20. The method of claim 1, wherein obtaining the one or more photoacoustic imaging signals corresponding to the brain of the subject through the skull of the subject further comprises receiving, using at least one ultrasonic transducer, (a) the acoustic signals generated by the brain of the subject in response to illumination by the first fraction of the at least one laser pulse and (b) the acoustic signals generated by the brain of the subject in response to illumination of the brain by the recycled laser light from the photon recycling device.

* * * * *